United States Patent
Tessier et al.

(10) Patent No.: US 11,208,477 B2
(45) Date of Patent: Dec. 28, 2021

(54) ANTIBODIES AND USE THEREOF

(71) Applicants: Novo Nordisk A/S, Bagsvaerd (DK); Regents of the University of Michigan, Ann Arbor, MI (US)

(72) Inventors: Peter Matthew Tessier, Saline, MI (US); Samuel D. Stimple, Boston, MA (US); Arne Staby, Bagsvaerd (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 16/836,064

(22) Filed: Mar. 31, 2020

(65) Prior Publication Data

US 2020/0308274 A1 Oct. 1, 2020

Related U.S. Application Data

(60) Provisional application No. 62/827,444, filed on Apr. 1, 2019.

(51) Int. Cl.
*C07K 16/00* (2006.01)
*G01N 33/53* (2006.01)
*C07K 16/26* (2006.01)

(52) U.S. Cl.
CPC ............ *C07K 16/26* (2013.01); *G01N 33/53* (2013.01); *C07K 2317/565* (2013.01); *C07K 2317/622* (2013.01)

(58) Field of Classification Search
CPC ... C07K 16/26; C07K 2317/565; G01N 33/53
See application file for complete search history.

(56) References Cited

U.S. PATENT DOCUMENTS

| 8,329,419 B2 | 12/2012 | Nicolaou et al. |
| 9,200,306 B2 | 12/2015 | Lin et al. |

FOREIGN PATENT DOCUMENTS

| CN | 103884846 A | 6/2014 |
| CN | 104267194 A | 1/2015 |
| WO | 9636883 A1 | 11/1996 |
| WO | 2006036834 A2 | 4/2006 |
| WO | 2007076319 A2 | 7/2007 |
| WO | 2010108153 A2 | 9/2010 |
| WO | 2012100267 A1 | 7/2012 |
| WO | 2015073727 A1 | 5/2015 |
| WO | 2015094876 A1 | 6/2015 |
| WO | 2016046753 A1 | 3/2016 |
| WO | 2019038412 A1 | 2/2019 |

OTHER PUBLICATIONS

Paul, Fundamental Immunology, 3rd Edition, 1993, pp. 292-295.*
Rudikoff et al, Proc. Natl. Acad. Sci. USA, 79(6):1979-1983, Mar. 1982.*
Colman P. M., Research in Immunology, 145:33-36, 1994.*
MacCallum et al, J. Mol. Biol., 262, 732-745, 1996.*
Casset et al, Biochemical and Biophysical Research Communications, 2003, vol. 307, pp. 198-205.*
Holm et al., Molecular Immunology, 2007, vol. 44, pp. 1075-1084.*
Vilsboll et al., "Liraglutide, a Long-Acting Human Glucagon-Like Peptide-1 Analog, Given as Monotherapy Significantly Improves Glycemic Control and Lowers Body Weight Without Risk of Hypoglycemia in Patients with Type 2 Diabetes.", Jun. 2007, Diabetes Care, vol. 30, No. 6, pp. 1608-1610.
Pridal et al., "Comparison of sandwich enzyme-linked immunoadsorbent assay and radioimmunoassay for determination of exogenous glucagon-like peptide-1(7-36)amide in plasma," Journal of Pharmaceutical and Biomedical Analysis, vol. 13, Issue 7, Jun. 1995, pp. 841-850.
Van Delft et al., "Identification of amidated forms of GLP-1 in rat tissues using a highly sensitive radioimmunoassay," Regulatory Peptides, vol. 70, Issues 2-3, Jun. 18, 1997, pp. 191-198.
Balagopal et al., "Incretin analogue, liraglutide a newer treatment approach for type-2 diabetes mellitus," International Journal of Pharma and Bio Sciences, vol. 4, Issue 3, 2013, p. P890-P896.
Buse et al., Liraglutide Treatment Is Associated with a Low Frequency and Magnitude of Antibody Formation with No Apparent Impacton Glycemic Response or Increased Frequency of Adverse Events: Results from the Liraglutide Effect and Action in Diabetes (LEAD) Trials, The Journal of Clinical Endocrinology & Metabolism, vol. 96, Issue 6, Jun. 1, 2011, pp. 1695-1702.
Thomsen et al., "A surface plasmon resonance assay for characterisation and epitope mapping of anti-GLP-1 antibodies," Journal of Molecular Recognition, vol. 31, Issue 8, Aug. 2018, Article No. e2711.
Kauth et al., "Immunohistochemical localization of glucagon-like peptide 1 Use of poly- and monoclonal antibodies," Histochemistry (1987) 86:509-515.
Shima et al., "Effect of glucagon-like peptide 1 (GLP-1) antibodies on glucose-induced insulin secretion in rats," Biomedical Research, 10 (5) 417-422, 1989.
Ghiglione et al., "Monoclonal antibodies to glucagon-like peptide 1," Digestion, vol. 54, Issue 6, 1993, pp. 396-397.
Hasegawa et al., "Solid-phase extraction treatment is required for measurement of active glucagon-like peptide-1 by enzyme-linked immunosorbent assay kit affected by heterophilic antibodies," JDI, Mar. 2019, vol. 10, Issue 2, pp. 302-308.

* cited by examiner

*Primary Examiner* — Mark Halvorson
(74) *Attorney, Agent, or Firm* — Rosemarie R. Wilk-Orescan

(57) ABSTRACT

The present invention relates to specific antibodies and use thereof, such as for identifying and/or quantifying liraglutide fibrils and/or semaglutide fibrils.

8 Claims, 1 Drawing Sheet
Specification includes a Sequence Listing.

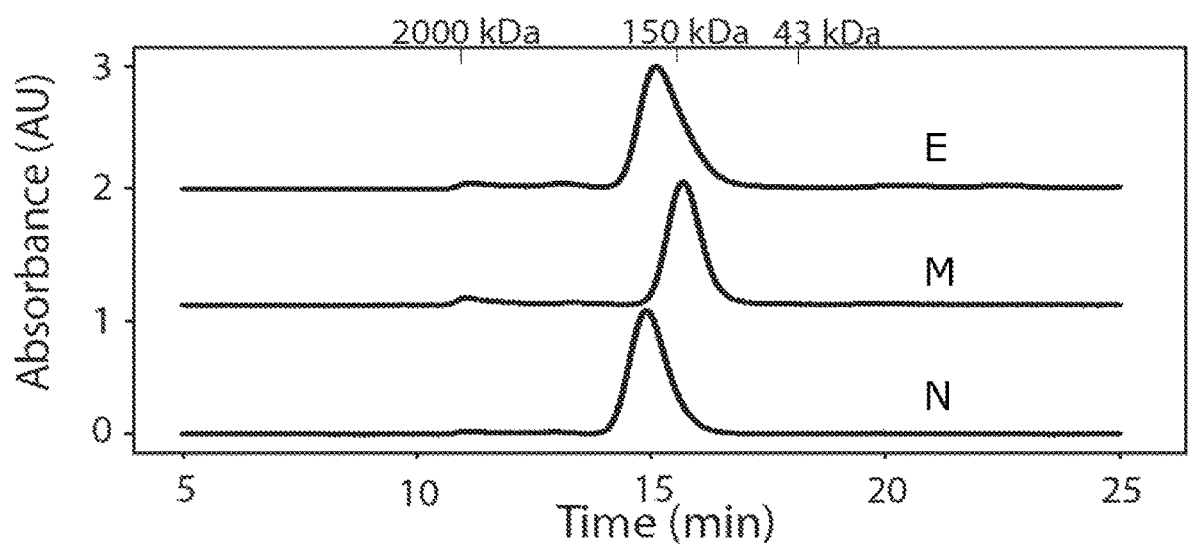

SEQUENCE LISTING

<160> NUMBER OF SEQ ID NOS: 126

<210> SEQ ID NO 1
<211> LENGTH: 520
<212> TYPE: PRT
<213> ORGANISM: ARTIFICIAL
<220> FEATURE:
<223> OTHER INFORMATION: Synthetic

<400> SEQUENCE: 1

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Val Ser Asp Ala
            20                  25                  30

Val Ser Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Asp Thr Thr Pro Pro
                85                  90                  95

Thr Phe Gly Gln Gly Thr Lys Val Glu Ile Lys Arg Thr Ser Pro Asn
            100                 105                 110

Ser Ala Ser His Ser Gly Ser Ala Pro Gln Thr Ser Ser Ala Pro Gly
        115                 120                 125

Ser Gln Glu Val Gln Leu Val Glu Ser Gly Gly Gly Leu Val Gln Pro
    130                 135                 140

Gly Gly Ser Leu Arg Leu Ser Cys Ala Ala Ser Gly Phe Asn Ile Lys
145                 150                 155                 160

Asp Thr Tyr Ile His Trp Val Arg Gln Ala Pro Gly Lys Gly Leu Glu
                165                 170                 175

Trp Val Ala Arg Ile Ser Pro Thr Gly Gly Tyr Thr Arg Tyr Ala Ala
            180                 185                 190

Ser Val Lys Gly Arg Phe Thr Ile Ser Ala Asp Thr Ser Lys Asn Thr
        195                 200                 205

Ala Tyr Leu Gln Met Asn Ser Leu Arg Ala Glu Asp Thr Ala Val Tyr
    210                 215                 220

Tyr Cys Ala Arg Asp Trp Phe Asp Ala Ala Ser Phe Ala Trp Phe Asp
225                 230                 235                 240

Phe Tyr Asp Tyr Ser Asp Tyr Trp Gly Gln Gly Thr Leu Val Thr Val
                245                 250                 255

Ser Ser Ala Ala Ala His Lys Thr His Thr Cys Pro Pro Cys Pro Ala
            260                 265                 270

Pro Glu Leu Leu Gly Gly Pro Ser Val Phe Leu Phe Pro Pro Lys Pro
        275                 280                 285

Lys Asp Thr Leu Met Ile Ser Arg Thr Pro Glu Val Thr Cys Val Val
    290                 295                 300

Val Asp Val Ser His Glu Asp Pro Glu Val Lys Phe Asn Trp Tyr Val
305                 310                 315                 320

Asp Gly Val Glu Val His Asn Ala Lys Thr Lys Pro Arg Glu Glu Gln
                325                 330                 335

Tyr Asn Ser Thr Tyr Arg Val Val Ser Val Leu Thr Val Leu His Gln
            340                 345                 350

Asp Trp Leu Asn Gly Lys Glu Tyr Lys Cys Lys Val Ser Asn Lys Ala
        355                 360                 365

Leu Pro Ala Pro Ile Glu Lys Thr Ile Ser Lys Ala Lys Gly Gln Pro
    370                 375                 380

Arg Glu Pro Gln Val Tyr Thr Leu Pro Pro Ser Arg Asp Glu Leu Thr
385                 390                 395                 400

Lys Asn Gln Val Ser Leu Thr Cys Leu Val Lys Gly Phe Tyr Pro Ser
                405                 410                 415

Asp Ile Ala Val Glu Trp Glu Ser Asn Gly Gln Pro Glu Asn Asn Tyr
            420                 425                 430

Lys Thr Thr Pro Pro Val Leu Asp Ser Asp Gly Ser Phe Phe Leu Tyr
        435                 440                 445

Ser Lys Leu Thr Val Asp Lys Ser Arg Trp Gln Gln Gly Asn Val Phe
    450                 455                 460

Ser Cys Ser Val Met His Glu Ala Leu His Asn His Tyr Thr Gln Lys
465                 470                 475                 480

Ser Leu Ser Leu Ser Pro Gly Lys Gly Ser His His His His His His
                485                 490                 495

Lys Leu Asp Tyr Lys Asp His Asp Gly Asp Tyr Lys Asp His Asp Ile
            500                 505                 510

Asp Tyr Lys Asp Asp Asp Lys
        515                 520

<210> SEQ ID NO 2
<211> LENGTH: 520
<212> TYPE: PRT
<213> ORGANISM: ARTIFICIAL
<220> FEATURE:
<223> OTHER INFORMATION: Synthetic

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asp Ser Ala
            20                  25                  30

Val Asn Trp Tyr Gln Gln Lys Pro Gly Lys Ala Pro Lys Leu Leu Ile
        35                  40                  45

```
Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Cys Thr Tyr Pro Pro
                85                  90                  95

Thr Phe Gly Gln Gly Thr Lys Val Glu Ile Lys Arg Thr Ser Pro Asn
                100                 105                 110

Ser Ala Ser His Ser Gly Ser Ala Pro Gln Thr Ser Ser Ala Pro Gly
            115                 120                 125

Ser Gln Glu Val Gln Leu Val Glu Ser Gly Gly Gly Leu Val Gln Pro
130                 135                 140

Gly Gly Ser Leu Arg Leu Ser Cys Ala Ala Ser Gly Phe Asn Ile Lys
145                 150                 155                 160

Asp Thr Tyr Ile His Trp Val Arg Gln Ala Pro Gly Lys Gly Leu Glu
                165                 170                 175

Trp Val Ala Arg Ile Ser Pro Tyr Asp Gly Asn Thr Arg Tyr Ala Ala
                180                 185                 190

Ser Val Lys Gly Arg Phe Thr Ile Ser Ala Asp Thr Ser Lys Asn Thr
            195                 200                 205

Ala Tyr Leu Gln Met Asn Ser Leu Arg Ala Glu Asp Thr Ala Val Tyr
    210                 215                 220

Tyr Cys Ala Arg Asp Trp Phe Asp Ala Ala Ser Phe Ala Trp Phe Asp
225                 230                 235                 240

Phe Tyr Asp Tyr Ser Asp Tyr Trp Gly Gln Gly Thr Leu Val Thr Val
                245                 250                 255

Ser Ser Ala Ala Ala His Lys Thr His Thr Cys Pro Pro Cys Pro Ala
            260                 265                 270

Pro Glu Leu Leu Gly Gly Pro Ser Val Phe Leu Phe Pro Pro Lys Pro
    275                 280                 285

Lys Asp Thr Leu Met Ile Ser Arg Thr Pro Glu Val Thr Cys Val Val
    290                 295                 300

Val Asp Val Ser His Glu Asp Pro Glu Val Lys Phe Asn Trp Tyr Val
305                 310                 315                 320

Asp Gly Val Glu Val His Asn Ala Lys Thr Lys Pro Arg Glu Glu Gln
                325                 330                 335

Tyr Asn Ser Thr Tyr Arg Val Val Ser Val Leu Thr Val Leu His Gln
                340                 345                 350

Asp Trp Leu Asn Gly Lys Glu Tyr Lys Cys Lys Val Ser Asn Lys Ala
            355                 360                 365

Leu Pro Ala Pro Ile Glu Lys Thr Ile Ser Lys Ala Lys Gly Gln Pro
    370                 375                 380

Arg Glu Pro Gln Val Tyr Thr Leu Pro Pro Ser Arg Asp Glu Leu Thr
385                 390                 395                 400

Lys Asn Gln Val Ser Leu Thr Cys Leu Val Lys Gly Phe Tyr Pro Ser
                405                 410                 415

Asp Ile Ala Val Glu Trp Glu Ser Asn Gly Gln Pro Glu Asn Asn Tyr
            420                 425                 430

Lys Thr Thr Pro Pro Val Leu Asp Ser Asp Gly Ser Phe Phe Leu Tyr
        435                 440                 445

Ser Lys Leu Thr Val Asp Lys Ser Arg Trp Gln Gln Gly Asn Val Phe
    450                 455                 460
```

```
Ser Cys Ser Val Met His Glu Ala Leu His Asn His Tyr Thr Gln Lys
465                 470                 475                 480

Ser Leu Ser Leu Ser Pro Gly Lys Gly Ser His His His His His
            485                 490                 495

Lys Leu Asp Tyr Lys Asp His Asp Gly Asp Tyr Lys Asp His Asp Ile
            500                 505                 510

Asp Tyr Lys Asp Asp Asp Lys
            515             520

<210> SEQ ID NO 3
<211> LENGTH: 520
<212> TYPE: PRT
<213> ORGANISM: ARTIFICIAL
<220> FEATURE:
<223> OTHER INFORMATION: Synthetic

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Thr Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Ser Tyr Pro Pro
                85                  90                  95

Thr Phe Gly Gln Gly Thr Lys Val Glu Ile Lys Arg Thr Ser Pro Asn
            100                 105                 110

Ser Ala Ser His Ser Gly Ser Ala Pro Gln Thr Ser Ser Ala Pro Gly
            115                 120                 125

Ser Gln Glu Val Gln Leu Val Glu Ser Gly Gly Gly Leu Val Gln Pro
130                 135                 140

Gly Gly Ser Leu Arg Leu Ser Cys Ala Ala Ser Gly Phe Asn Ile Lys
145                 150                 155                 160

Asp Thr Tyr Ile His Trp Val Arg Gln Ala Pro Gly Lys Gly Leu Glu
            165                 170                 175

Trp Val Ala Arg Ile Ser Pro Ala Gly Gly Thr Thr Arg Tyr Ala Ala
            180                 185                 190

Ser Val Lys Gly Arg Phe Thr Ile Ser Ala Asp Thr Ser Lys Asn Thr
            195                 200                 205

Ala Tyr Leu Gln Met Asn Ser Leu Arg Ala Glu Asp Thr Ala Val Tyr
210                 215                 220

Tyr Cys Ala Arg Asp Trp Phe Asp Ala Ala Ser Phe Ala Trp Phe Asp
225                 230                 235                 240

Phe Tyr Asp Tyr Ser Asp Tyr Trp Gly Gln Gly Thr Leu Val Thr Val
            245                 250                 255

Ser Ser Ala Ala Ala His Lys Thr His Thr Cys Pro Pro Cys Pro Ala
            260                 265                 270

Pro Glu Leu Leu Gly Gly Pro Ser Val Phe Leu Phe Pro Pro Lys Pro
            275                 280                 285

Lys Asp Thr Leu Met Ile Ser Arg Thr Pro Glu Val Thr Cys Val Val
            290                 295                 300
```

Val Asp Val Ser His Glu Asp Pro Glu Val Lys Phe Asn Trp Tyr Val
305                 310                 315                 320

Asp Gly Val Glu Val His Asn Ala Lys Thr Lys Pro Arg Glu Gln
            325                 330                 335

Tyr Asn Ser Thr Tyr Arg Val Val Ser Val Leu Thr Val Leu His Gln
                340                 345                 350

Asp Trp Leu Asn Gly Lys Glu Tyr Lys Cys Lys Val Ser Asn Lys Ala
            355                 360                 365

Leu Pro Ala Pro Ile Glu Lys Thr Ile Ser Lys Ala Lys Gly Gln Pro
370                 375                 380

Arg Glu Pro Gln Val Tyr Thr Leu Pro Pro Ser Arg Asp Glu Leu Thr
385                 390                 395                 400

Lys Asn Gln Val Ser Leu Thr Cys Leu Val Lys Gly Phe Tyr Pro Ser
                405                 410                 415

Asp Ile Ala Val Glu Trp Glu Ser Asn Gly Gln Pro Glu Asn Asn Tyr
            420                 425                 430

Lys Thr Thr Pro Pro Val Leu Asp Ser Asp Gly Ser Phe Phe Leu Tyr
                435                 440                 445

Ser Lys Leu Thr Val Asp Lys Ser Arg Trp Gln Gln Gly Asn Val Phe
450                 455                 460

Ser Cys Ser Val Met His Glu Ala Leu His Asn His Tyr Thr Gln Lys
465                 470                 475                 480

Ser Leu Ser Leu Ser Pro Gly Lys Gly Ser His His His His His His
                485                 490                 495

Lys Leu Asp Tyr Lys Asp His Asp Gly Asp Tyr Lys Asp His Asp Ile
                500                 505                 510

Asp Tyr Lys Asp Asp Asp Asp Lys
            515                 520

<210> SEQ ID NO 4
<211> LENGTH: 520
<212> TYPE: PRT
<213> ORGANISM: ARTIFICIAL
<220> FEATURE:
<223> OTHER INFORMATION: Synthetic

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ile Val Ser Asn Ala
            20                  25                  30

Val Thr Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Cys Thr Thr Pro Pro
                85                  90                  95

Thr Phe Gly Gln Gly Thr Lys Val Glu Ile Lys Arg Thr Ser Pro Asn
            100                 105                 110

Ser Ala Ser His Ser Gly Ser Ala Pro Gln Thr Ser Ser Ala Pro Gly
        115                 120                 125

Ser Gln Glu Val Gln Leu Val Glu Ser Gly Gly Gly Leu Val Gln Pro
    130                 135                 140

Gly Gly Ser Leu Arg Leu Ser Cys Ala Ala Ser Gly Phe Asn Ile Lys
145                 150                 155                 160

Asp Thr Tyr Ile His Trp Val Arg Gln Ala Pro Gly Lys Gly Leu Glu
            165                 170                 175

Trp Val Ala Arg Ile Tyr Pro Asp Gly Gly Asn Thr Arg Tyr Ala Gly
        180                 185                 190

Ser Val Lys Gly Arg Phe Thr Ile Ser Ala Asp Thr Ser Lys Asn Thr
    195                 200                 205

Ala Tyr Leu Gln Met Asn Ser Leu Arg Ala Glu Asp Thr Ala Val Tyr
210                 215                 220

Tyr Cys Val Arg Asp Trp Phe Asp Ala Ala Ser Phe Ala Trp Phe Asp
225                 230                 235                 240

Phe Tyr Asp Tyr Ser Asp Tyr Trp Gly Gln Gly Thr Leu Val Thr Val
                245                 250                 255

Ser Ser Ala Ala Ala His Lys Thr His Thr Cys Pro Pro Cys Pro Ala
            260                 265                 270

Pro Glu Leu Leu Gly Gly Pro Ser Val Phe Leu Phe Pro Pro Lys Pro
        275                 280                 285

Lys Asp Thr Leu Met Ile Ser Arg Thr Pro Glu Val Thr Cys Val Val
290                 295                 300

Val Asp Val Ser His Glu Asp Pro Glu Val Lys Phe Asn Trp Tyr Val
305                 310                 315                 320

Asp Gly Val Glu Val His Asn Ala Lys Thr Lys Pro Arg Glu Glu Gln
                325                 330                 335

Tyr Asn Ser Thr Tyr Arg Val Val Ser Val Leu Thr Val Leu His Gln
            340                 345                 350

Asp Trp Leu Asn Gly Lys Glu Tyr Lys Cys Lys Val Ser Asn Lys Ala
        355                 360                 365

Leu Pro Ala Pro Ile Glu Lys Thr Ile Ser Lys Ala Lys Gly Gln Pro
370                 375                 380

Arg Glu Pro Gln Val Tyr Thr Leu Pro Pro Ser Arg Asp Glu Leu Thr
385                 390                 395                 400

Lys Asn Gln Val Ser Leu Thr Cys Leu Val Lys Gly Phe Tyr Pro Ser
                405                 410                 415

Asp Ile Ala Val Glu Trp Glu Ser Asn Gly Gln Pro Glu Asn Asn Tyr
            420                 425                 430

Lys Thr Thr Pro Pro Val Leu Asp Ser Asp Gly Ser Phe Phe Leu Tyr
        435                 440                 445

Ser Lys Leu Thr Val Asp Lys Ser Arg Trp Gln Gln Gly Asn Val Phe
450                 455                 460

Ser Cys Ser Val Met His Glu Ala Leu His Asn His Tyr Thr Gln Lys
465                 470                 475                 480

Ser Leu Ser Leu Ser Pro Gly Lys Gly Ser His His His His His His
                485                 490                 495

Lys Leu Asp Tyr Lys Asp His Asp Gly Asp Tyr Lys Asp His Asp Ile
            500                 505                 510

Asp Tyr Lys Asp Asp Asp Asp Lys
        515                 520

<210> SEQ ID NO 5
<211> LENGTH: 520
<212> TYPE: PRT
<213> ORGANISM: ARTIFICIAL
<220> FEATURE:
<223> OTHER INFORMATION: Synthetic

<400> SEQUENCE: 5

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Val Ser Asp Ala
            20                  25                  30

Val Asn Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Asn Pro Pro
                85                  90                  95

Thr Phe Gly Gln Gly Thr Lys Val Glu Ile Lys Arg Thr Ser Pro Asn
            100                 105                 110

Ser Ala Ser His Ser Gly Ser Ala Pro Gln Thr Ser Ser Ala Pro Gly
        115                 120                 125

Ser Gln Glu Val Gln Leu Val Glu Ser Gly Gly Leu Val Gln Pro
130                 135                 140

Gly Gly Ser Leu Arg Leu Ser Cys Ala Ala Ser Gly Phe Asn Ile Lys
145                 150                 155                 160

Asp Thr Tyr Ile His Trp Val Arg Gln Ala Pro Gly Lys Gly Leu Glu
                165                 170                 175

Trp Val Ala Arg Ile Thr Pro Thr Asp Gly Thr Thr Arg Tyr Ala Val
            180                 185                 190

Ser Val Lys Gly Arg Phe Thr Ile Ser Ala Asp Thr Ser Lys Asn Thr
        195                 200                 205

Ala Tyr Leu Gln Met Asn Ser Leu Arg Ala Glu Asp Thr Ala Val Tyr
    210                 215                 220

Tyr Cys Ala Arg Glu Trp Tyr Glu Ala Ser Tyr Tyr Asp Trp Phe Asp
225                 230                 235                 240

Tyr Phe Asp Phe Ser Asp Tyr Trp Gly Gln Gly Thr Leu Val Thr Val
                245                 250                 255

Ser Ser Ala Ala Ala His Lys Thr His Thr Cys Pro Pro Cys Pro Ala
            260                 265                 270

Pro Glu Leu Leu Gly Gly Pro Ser Val Phe Leu Phe Pro Pro Lys Pro
        275                 280                 285

Lys Asp Thr Leu Met Ile Ser Arg Thr Pro Glu Val Thr Cys Val Val
    290                 295                 300

Val Asp Val Ser His Glu Asp Pro Glu Val Lys Phe Asn Trp Tyr Val
305                 310                 315                 320

Asp Gly Val Glu Val His Asn Ala Lys Thr Lys Pro Arg Glu Glu Gln
                325                 330                 335

Tyr Asn Ser Thr Tyr Arg Val Val Ser Val Leu Thr Val Leu His Gln
            340                 345                 350

Asp Trp Leu Asn Gly Lys Glu Tyr Lys Cys Lys Val Ser Asn Lys Ala
        355                 360                 365

Leu Pro Ala Pro Ile Glu Lys Thr Ile Ser Lys Ala Lys Gly Gln Pro
    370                 375                 380

Arg Glu Pro Gln Val Tyr Thr Leu Pro Pro Ser Arg Asp Glu Leu Thr
385                 390                 395                 400

Lys Asn Gln Val Ser Leu Thr Cys Leu Val Lys Gly Phe Tyr Pro Ser
```

```
                    405                 410                 415
Asp Ile Ala Val Glu Trp Glu Ser Asn Gly Gln Pro Glu Asn Asn Tyr
                420                 425                 430

Lys Thr Thr Pro Pro Val Leu Asp Ser Asp Gly Ser Phe Phe Leu Tyr
            435                 440                 445

Ser Lys Leu Thr Val Asp Lys Ser Arg Trp Gln Gln Gly Asn Val Phe
        450                 455                 460

Ser Cys Ser Val Met His Glu Ala Leu His Asn His Tyr Thr Gln Lys
465                 470                 475                 480

Ser Leu Ser Leu Ser Pro Gly Lys Gly Ser His His His His His His
                485                 490                 495

Lys Leu Asp Tyr Lys Asp His Asp Gly Asp Tyr Lys Asp His Asp Ile
                500                 505                 510

Asp Tyr Lys Asp Asp Asp Asp Lys
                515                 520

<210> SEQ ID NO 6
<211> LENGTH: 520
<212> TYPE: PRT
<213> ORGANISM: ARTIFICIAL
<220> FEATURE:
<223> OTHER INFORMATION: Synthetic

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ile Val Asn Tyr Ala
            20                  25                  30

Val Tyr Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Val Thr Tyr Tyr Cys Gln Gln His Tyr Thr Thr Pro Pro
                85                  90                  95

Thr Phe Gly Gln Gly Thr Lys Val Glu Ile Lys Arg Thr Ser Pro Asn
            100                 105                 110

Ser Ala Ser His Ser Gly Ser Ala Pro Gln Thr Ser Ser Ala Pro Gly
        115                 120                 125

Ser Gln Glu Val Gln Leu Val Glu Ser Gly Gly Gly Leu Val Gln Pro
    130                 135                 140

Gly Gly Ser Leu Arg Leu Ser Cys Ala Ala Ser Gly Phe Asn Ile Lys
145                 150                 155                 160

Asp Thr Tyr Ile His Trp Val Arg Gln Ala Pro Gly Lys Gly Leu Glu
                165                 170                 175

Trp Val Ala Arg Ile Ala Pro Thr Asn Gly Thr Thr Arg Tyr Ala Asp
            180                 185                 190

Ser Val Lys Gly Arg Phe Thr Ile Ser Ala Asp Thr Ser Lys Asn Thr
        195                 200                 205

Ala Tyr Leu Gln Met Asn Ser Leu Arg Ala Glu Asp Thr Ala Val Tyr
    210                 215                 220

Tyr Cys Ala Arg Glu Trp Tyr Glu Ala Ser Tyr Tyr Asp Trp Phe Asp
225                 230                 235                 240

Tyr Phe Asp Phe Ser Asp Tyr Trp Gly Gln Gly Thr Leu Val Thr Val
```

```
                    245                 250                 255
Ser Ser Ala Ala Ala His Lys Thr His Thr Cys Pro Pro Cys Pro Ala
            260                 265                 270

Pro Glu Leu Leu Gly Gly Pro Ser Val Phe Leu Phe Pro Pro Lys Pro
        275                 280                 285

Lys Asp Thr Leu Met Ile Ser Arg Thr Pro Glu Val Thr Cys Val Val
    290                 295                 300

Val Asp Val Ser His Glu Asp Pro Glu Val Lys Phe Asn Trp Tyr Val
305                 310                 315                 320

Asp Gly Val Glu Val His Asn Ala Lys Thr Lys Pro Arg Glu Glu Gln
            325                 330                 335

Tyr Asn Ser Thr Tyr Arg Val Val Ser Val Leu Thr Val Leu His Gln
        340                 345                 350

Asp Trp Leu Asn Gly Lys Glu Tyr Lys Cys Lys Val Ser Asn Lys Ala
    355                 360                 365

Leu Pro Ala Pro Ile Glu Lys Thr Ile Ser Lys Ala Lys Gly Gln Pro
370                 375                 380

Arg Glu Pro Gln Val Tyr Thr Leu Pro Pro Ser Arg Asp Glu Leu Thr
385                 390                 395                 400

Lys Asn Gln Val Ser Leu Thr Cys Leu Val Lys Gly Phe Tyr Pro Ser
            405                 410                 415

Asp Ile Ala Val Glu Trp Glu Ser Asn Gly Gln Pro Glu Asn Asn Tyr
        420                 425                 430

Lys Thr Thr Pro Pro Val Leu Asp Ser Asp Gly Ser Phe Phe Leu Tyr
    435                 440                 445

Ser Lys Leu Thr Val Asp Lys Ser Arg Trp Gln Gln Gly Asn Val Phe
450                 455                 460

Ser Cys Ser Val Met His Glu Ala Leu His Asn His Tyr Thr Gln Lys
465                 470                 475                 480

Ser Leu Ser Leu Ser Pro Gly Lys Gly Ser His His His His His His
            485                 490                 495

Lys Leu Asp Tyr Lys Asp His Asp Gly Asp Tyr Lys Asp His Asp Ile
        500                 505                 510

Asp Tyr Lys Asp Asp Asp Asp Lys
    515                 520

<210> SEQ ID NO 7
<211> LENGTH: 520
<212> TYPE: PRT
<213> ORGANISM: ARTIFICIAL
<220> FEATURE:
<223> OTHER INFORMATION: Synthetic

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Val Thr Ala Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Asn Thr Tyr Pro Pro
```

```
            85                  90                  95
Thr Phe Gly Gln Gly Thr Lys Val Glu Ile Lys Arg Thr Ser Pro Asn
            100                 105                 110

Ser Ala Ser His Ser Gly Ser Ala Pro Gln Thr Ser Ser Ala Pro Gly
            115                 120                 125

Ser Gln Glu Val Gln Leu Val Glu Ser Gly Gly Leu Val Gln Pro
            130                 135             140

Gly Gly Ser Leu Arg Leu Ser Cys Ala Ala Ser Gly Phe Asn Ile Lys
145                 150                 155                 160

Asp Thr Tyr Ile His Trp Val Arg Gln Ala Pro Gly Lys Gly Leu Glu
                165                 170                 175

Trp Val Ala Arg Ile Ala Pro Thr Ser Gly Tyr Thr Arg Tyr Ala Val
            180                 185                 190

Ser Val Lys Gly Arg Phe Thr Ile Ser Ala Asp Thr Ser Lys Asn Thr
            195                 200                 205

Ala Tyr Leu Gln Met Asn Ser Leu Arg Ala Glu Asp Thr Ala Val Tyr
            210                 215                 220

Tyr Cys Ala Arg Glu Trp Tyr Glu Ala Ser Tyr Tyr Asp Trp Phe Asp
225                 230                 235                 240

Tyr Phe Asp Phe Ser Asp Tyr Trp Gly Gln Gly Thr Leu Val Thr Val
                245                 250                 255

Ser Ser Ala Ala Ala His Lys Thr His Thr Cys Pro Pro Cys Pro Ala
            260                 265                 270

Pro Glu Leu Leu Gly Gly Pro Ser Val Phe Leu Phe Pro Pro Lys Pro
            275                 280                 285

Lys Asp Thr Leu Met Ile Ser Arg Thr Pro Glu Val Thr Cys Val Val
            290                 295                 300

Val Asp Val Ser His Glu Asp Pro Glu Val Lys Phe Asn Trp Tyr Val
305                 310                 315                 320

Asp Gly Val Glu Val His Asn Ala Lys Thr Lys Pro Arg Glu Glu Gln
                325                 330                 335

Tyr Asn Ser Thr Tyr Arg Val Val Ser Val Leu Thr Val Leu His Gln
            340                 345                 350

Asp Trp Leu Asn Gly Lys Glu Tyr Lys Cys Lys Val Ser Asn Lys Ala
            355                 360                 365

Leu Pro Ala Pro Ile Glu Lys Thr Ile Ser Lys Ala Lys Gly Gln Pro
            370                 375                 380

Arg Glu Pro Gln Val Tyr Thr Leu Pro Pro Ser Arg Asp Glu Leu Thr
385                 390                 395                 400

Lys Asn Gln Val Ser Leu Thr Cys Leu Val Lys Gly Phe Tyr Pro Ser
                405                 410                 415

Asp Ile Ala Val Glu Trp Glu Ser Asn Gly Gln Pro Glu Asn Asn Tyr
            420                 425                 430

Lys Thr Thr Pro Pro Val Leu Asp Ser Asp Gly Ser Phe Phe Leu Tyr
            435                 440                 445

Ser Lys Leu Thr Val Asp Lys Ser Arg Trp Gln Gln Gly Asn Val Phe
            450                 455                 460

Ser Cys Ser Val Met His Glu Ala Leu His Asn His Tyr Thr Gln Lys
465                 470                 475                 480

Ser Leu Ser Leu Ser Pro Gly Lys Gly Ser His His His His His His
                485                 490                 495

Lys Leu Asp Tyr Lys Asp His Asp Gly Asp Tyr Lys Asp His Asp Ile
            500                 505                 510
```

-continued

Asp Tyr Lys Asp Asp Asp Lys
        515                 520

<210> SEQ ID NO 8
<211> LENGTH: 520
<212> TYPE: PRT
<213> ORGANISM: ARTIFICIAL
<220> FEATURE:
<223> OTHER INFORMATION: Synthetic

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Ser Pro Asn
            100                 105                 110

Ser Ala Ser His Ser Gly Ser Ala Pro Gln Thr Ser Ser Ala Pro Gly
        115                 120                 125

Ser Gln Glu Val Gln Leu Val Glu Ser Gly Gly Leu Val Gln Pro
130                 135                 140

Gly Gly Ser Leu Arg Leu Ser Cys Ala Ala Ser Gly Phe Asn Ile Lys
145                 150                 155                 160

Asp Thr Tyr Ile His Trp Val Arg Gln Ala Pro Gly Lys Gly Leu Glu
                165                 170                 175

Trp Val Ala Arg Ile Tyr Pro Thr Asn Gly Tyr Thr Arg Tyr Ala Asp
            180                 185                 190

Ser Val Lys Gly Arg Phe Thr Ile Ser Ala Asp Thr Ser Lys Asn Thr
        195                 200                 205

Ala Tyr Leu Gln Met Asn Ser Leu Arg Ala Glu Asp Thr Ala Val Tyr
    210                 215                 220

Tyr Cys Ala Arg Glu Val Tyr Asp Thr Ser Tyr Phe Phe Trp Phe Asp
225                 230                 235                 240

Tyr Tyr Asp Tyr Tyr Asp Tyr Trp Gly Gln Gly Thr Leu Val Thr Val
                245                 250                 255

Ser Ser Ala Ala Ala His Lys Thr His Thr Cys Pro Pro Cys Pro Ala
            260                 265                 270

Pro Glu Leu Leu Gly Gly Pro Ser Val Phe Leu Phe Pro Pro Lys Pro
        275                 280                 285

Lys Asp Thr Leu Met Ile Ser Arg Thr Pro Glu Val Thr Cys Val Val
    290                 295                 300

Val Asp Val Ser His Glu Asp Pro Glu Val Lys Phe Asn Trp Tyr Val
305                 310                 315                 320

Asp Gly Val Glu Val His Asn Ala Lys Thr Lys Pro Arg Glu Glu Gln
                325                 330                 335

Tyr Asn Ser Thr Tyr Arg Val Val Ser Val Leu Thr Val Leu His Gln
            340                 345                 350

-continued

```
Asp Trp Leu Asn Gly Lys Glu Tyr Lys Cys Lys Val Ser Asn Lys Ala
            355                 360                 365

Leu Pro Ala Pro Ile Glu Lys Thr Ile Ser Lys Ala Lys Gly Gln Pro
    370                 375                 380

Arg Glu Pro Gln Val Tyr Thr Leu Pro Pro Ser Arg Asp Glu Leu Thr
385                 390                 395                 400

Lys Asn Gln Val Ser Leu Thr Cys Leu Val Lys Gly Phe Tyr Pro Ser
                405                 410                 415

Asp Ile Ala Val Glu Trp Glu Ser Asn Gly Gln Pro Glu Asn Asn Tyr
            420                 425                 430

Lys Thr Thr Pro Pro Val Leu Asp Ser Asp Gly Ser Phe Phe Leu Tyr
        435                 440                 445

Ser Lys Leu Thr Val Asp Lys Ser Arg Trp Gln Gln Gly Asn Val Phe
    450                 455                 460

Ser Cys Ser Val Met His Glu Ala Leu His Asn His Tyr Thr Gln Lys
465                 470                 475                 480

Ser Leu Ser Leu Ser Pro Gly Lys Gly Ser His His His His His His
                485                 490                 495

Lys Leu Asp Tyr Lys Asp His Asp Gly Asp Tyr Lys Asp His Asp Ile
            500                 505                 510

Asp Tyr Lys Asp Asp Asp Asp Lys
        515                 520

<210> SEQ ID NO 9
<211> LENGTH: 520
<212> TYPE: PRT
<213> ORGANISM: ARTIFICIAL
<220> FEATURE:
<223> OTHER INFORMATION: Synthetic

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Ser Pro Asn
            100                 105                 110

Ser Ala Ser His Ser Gly Ser Ala Pro Gln Thr Ser Ser Ala Pro Gly
        115                 120                 125

Ser Gln Glu Val Gln Leu Val Glu Ser Gly Gly Leu Val Gln Pro
    130                 135                 140

Gly Gly Ser Leu Arg Leu Ser Cys Ala Ala Ser Gly Phe Asn Ile Lys
145                 150                 155                 160

Asp Thr Tyr Ile His Trp Val Arg Gln Ala Pro Gly Lys Gly Leu Glu
                165                 170                 175

Trp Val Ala Arg Ile Tyr Pro Thr Asn Gly Tyr Thr Arg Tyr Ala Asp
            180                 185                 190
```

Ser Val Lys Gly Arg Phe Thr Ile Ser Ala Asp Thr Ser Lys Asn Thr
        195                    200                    205

Ala Tyr Leu Gln Met Asn Ser Leu Arg Ala Glu Asp Thr Ala Val Tyr
 210                        215                    220

Tyr Cys Ala Arg Asp Trp Phe Asp Ala Ala Ser Phe Ala Trp Phe Asp
225                    230                    235                    240

Phe Tyr Asp Tyr Ser Asp Tyr Trp Gly Gln Gly Thr Leu Val Thr Val
                245                    250                    255

Ser Ser Ala Ala Ala His Lys Thr His Thr Cys Pro Pro Cys Pro Ala
            260                    265                    270

Pro Glu Leu Leu Gly Gly Pro Ser Val Phe Leu Phe Pro Pro Lys Pro
    275                    280                    285

Lys Asp Thr Leu Met Ile Ser Arg Thr Pro Glu Val Thr Cys Val Val
290                    295                    300

Val Asp Val Ser His Glu Asp Pro Glu Val Lys Phe Asn Trp Tyr Val
305                    310                    315                    320

Asp Gly Val Glu Val His Asn Ala Lys Thr Lys Pro Arg Glu Glu Gln
                325                    330                    335

Tyr Asn Ser Thr Tyr Arg Val Val Ser Val Leu Thr Val Leu His Gln
           340                    345                    350

Asp Trp Leu Asn Gly Lys Glu Tyr Lys Cys Lys Val Ser Asn Lys Ala
      355                    360                    365

Leu Pro Ala Pro Ile Glu Lys Thr Ile Ser Lys Ala Lys Gly Gln Pro
   370                    375                    380

Arg Glu Pro Gln Val Tyr Thr Leu Pro Pro Ser Arg Asp Glu Leu Thr
385                    390                    395                    400

Lys Asn Gln Val Ser Leu Thr Cys Leu Val Lys Gly Phe Tyr Pro Ser
           405                    410                    415

Asp Ile Ala Val Glu Trp Glu Ser Asn Gly Gln Pro Glu Asn Asn Tyr
           420                    425                    430

Lys Thr Thr Pro Pro Val Leu Asp Ser Asp Gly Ser Phe Phe Leu Tyr
      435                    440                    445

Ser Lys Leu Thr Val Asp Lys Ser Arg Trp Gln Gln Gly Asn Val Phe
 450                       455                    460

Ser Cys Ser Val Met His Glu Ala Leu His Asn His Tyr Thr Gln Lys
465                    470                    475                    480

Ser Leu Ser Leu Ser Pro Gly Lys Gly Ser His His His His His His
           485                    490                    495

Lys Leu Asp Tyr Lys Asp His Asp Gly Asp Tyr Lys Asp His Asp Ile
           500                    505                    510

Asp Tyr Lys Asp Asp Asp Asp Lys
      515                    520

<210> SEQ ID NO 10
<211> LENGTH: 520
<212> TYPE: PRT
<213> ORGANISM: ARTIFICIAL
<220> FEATURE:
<223> OTHER INFORMATION: Synthetic

<400> SEQUENCE: 10

Asp Ile Gln Met Thr Gln Ser Pro Ser Ser Leu Ser Ala Ser Val Gly
1                  5                    10                    15

Asp Arg Val Thr Ile Thr Cys Arg Ala Ser Gln Asp Val Asn Thr Ala
           20                    25                    30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Ser Pro Asn
            100                 105                 110

Ser Ala Ser His Ser Gly Ser Ala Pro Gln Thr Ser Ser Ala Pro Gly
            115                 120                 125

Ser Gln Glu Val Gln Leu Val Glu Ser Gly Gly Gly Leu Val Gln Pro
        130                 135                 140

Gly Gly Ser Leu Arg Leu Ser Cys Ala Ala Ser Gly Phe Asn Ile Lys
145                 150                 155                 160

Asp Thr Tyr Ile His Trp Val Arg Gln Ala Pro Gly Lys Gly Leu Glu
                165                 170                 175

Trp Val Ala Arg Ile Tyr Pro Thr Asn Gly Tyr Thr Arg Tyr Ala Asp
            180                 185                 190

Ser Val Lys Gly Arg Phe Thr Ile Ser Ala Asp Thr Ser Lys Asn Thr
        195                 200                 205

Ala Tyr Leu Gln Met Asn Ser Leu Arg Ala Glu Asp Thr Ala Val Tyr
    210                 215                 220

Tyr Cys Ala Arg Glu Trp Tyr Glu Ala Ser Tyr Tyr Asp Trp Phe Asp
225                 230                 235                 240

Tyr Phe Asp Phe Ser Asp Tyr Trp Gly Gln Gly Thr Leu Val Thr Val
                245                 250                 255

Ser Ser Ala Ala Ala His Lys Thr His Thr Cys Pro Pro Cys Pro Ala
            260                 265                 270

Pro Glu Leu Leu Gly Gly Pro Ser Val Phe Leu Phe Pro Pro Lys Pro
        275                 280                 285

Lys Asp Thr Leu Met Ile Ser Arg Thr Pro Glu Val Thr Cys Val Val
    290                 295                 300

Val Asp Val Ser His Glu Asp Pro Glu Val Lys Phe Asn Trp Tyr Val
305                 310                 315                 320

Asp Gly Val Glu Val His Asn Ala Lys Thr Lys Pro Arg Glu Glu Gln
                325                 330                 335

Tyr Asn Ser Thr Tyr Arg Val Val Ser Val Leu Thr Val Leu His Gln
            340                 345                 350

Asp Trp Leu Asn Gly Lys Glu Tyr Lys Cys Lys Val Ser Asn Lys Ala
        355                 360                 365

Leu Pro Ala Pro Ile Glu Lys Thr Ile Ser Lys Ala Lys Gly Gln Pro
    370                 375                 380

Arg Glu Pro Gln Val Tyr Thr Leu Pro Pro Ser Arg Asp Glu Leu Thr
385                 390                 395                 400

Lys Asn Gln Val Ser Leu Thr Cys Leu Val Lys Gly Phe Tyr Pro Ser
                405                 410                 415

Asp Ile Ala Val Glu Trp Glu Ser Asn Gly Gln Pro Glu Asn Asn Tyr
            420                 425                 430

Lys Thr Thr Pro Pro Val Leu Asp Ser Asp Gly Ser Phe Phe Leu Tyr
        435                 440                 445

```
Ser Lys Leu Thr Val Asp Lys Ser Arg Trp Gln Gln Gly Asn Val Phe
    450                 455                 460

Ser Cys Ser Val Met His Glu Ala Leu His Asn His Tyr Thr Gln Lys
465                 470                 475                 480

Ser Leu Ser Leu Ser Pro Gly Lys Gly Ser His His His His His His
                485                 490                 495

Lys Leu Asp Tyr Lys Asp His Asp Gly Asp Tyr Lys Asp His Asp Ile
                500                 505                 510

Asp Tyr Lys Asp Asp Asp Lys
            515             520

<210> SEQ ID NO 11
<211> LENGTH: 520
<212> TYPE: PRT
<213> ORGANISM: ARTIFICIAL
<220> FEATURE:
<223> OTHER INFORMATION: Synthetic

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Ser Pro Asn
            100                 105                 110

Ser Ala Ser His Ser Gly Ser Ala Pro Gln Thr Ser Ser Ala Pro Gly
        115                 120                 125

Ser Gln Glu Val Gln Leu Val Glu Ser Gly Gly Gly Leu Val Gln Pro
    130                 135                 140

Gly Gly Ser Leu Arg Leu Ser Cys Ala Ala Ser Gly Phe Asn Ile Lys
145                 150                 155                 160

Asp Thr Tyr Ile His Trp Val Arg Gln Ala Pro Gly Lys Gly Leu Glu
                165                 170                 175

Trp Val Ala Arg Ile Tyr Pro Thr Asn Gly Tyr Thr Arg Tyr Ala Asp
            180                 185                 190

Ser Val Lys Gly Arg Phe Thr Ile Ser Ala Asp Thr Ser Lys Asn Thr
        195                 200                 205

Ala Tyr Leu Gln Met Asn Ser Leu Arg Ala Glu Asp Thr Ala Val Tyr
    210                 215                 220

Tyr Cys Ala Arg Glu Trp Ser Asp Ala Thr Tyr Phe Tyr Trp Phe Asp
225                 230                 235                 240

Phe Tyr Asp Tyr Ser Asp Tyr Trp Gly Gln Gly Thr Leu Val Thr Val
                245                 250                 255

Ser Ser Ala Ala Ala His Lys Thr His Thr Cys Pro Pro Cys Pro Ala
            260                 265                 270

Pro Glu Leu Leu Gly Gly Pro Ser Val Phe Leu Phe Pro Pro Lys Pro
        275                 280                 285
```

```
Lys Asp Thr Leu Met Ile Ser Arg Thr Pro Glu Val Thr Cys Val Val
    290                 295                 300

Val Asp Val Ser His Glu Asp Pro Glu Val Lys Phe Asn Trp Tyr Val
305                 310                 315                 320

Asp Gly Val Glu Val His Asn Ala Lys Thr Lys Pro Arg Glu Glu Gln
                325                 330                 335

Tyr Asn Ser Thr Tyr Arg Val Val Ser Val Leu Thr Val Leu His Gln
            340                 345                 350

Asp Trp Leu Asn Gly Lys Glu Tyr Lys Cys Lys Val Ser Asn Lys Ala
        355                 360                 365

Leu Pro Ala Pro Ile Glu Lys Thr Ile Ser Lys Ala Lys Gly Gln Pro
370                 375                 380

Arg Glu Pro Gln Val Tyr Thr Leu Pro Pro Ser Arg Asp Glu Leu Thr
385                 390                 395                 400

Lys Asn Gln Val Ser Leu Thr Cys Leu Val Lys Gly Phe Tyr Pro Ser
                405                 410                 415

Asp Ile Ala Val Glu Trp Glu Ser Asn Gly Gln Pro Glu Asn Asn Tyr
            420                 425                 430

Lys Thr Thr Pro Pro Val Leu Asp Ser Asp Gly Ser Phe Phe Leu Tyr
        435                 440                 445

Ser Lys Leu Thr Val Asp Lys Ser Arg Trp Gln Gln Gly Asn Val Phe
450                 455                 460

Ser Cys Ser Val Met His Glu Ala Leu His Asn His Tyr Thr Gln Lys
465                 470                 475                 480

Ser Leu Ser Leu Ser Pro Gly Lys Gly Ser His His His His His His
                485                 490                 495

Lys Leu Asp Tyr Lys Asp His Asp Gly Asp Tyr Lys Asp His Asp Ile
            500                 505                 510

Asp Tyr Lys Asp Asp Asp Asp Lys
        515                 520

<210> SEQ ID NO 12
<211> LENGTH: 520
<212> TYPE: PRT
<213> ORGANISM: ARTIFICIAL
<220> FEATURE:
<223> OTHER INFORMATION: Synthetic

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Ser Pro Asn
            100                 105                 110

Ser Ala Ser His Ser Gly Ser Ala Pro Gln Thr Ser Ser Ala Pro Gly
        115                 120                 125
```

Ser Gln Glu Val Gln Leu Val Glu Ser Gly Gly Gly Leu Val Gln Pro
130                 135                 140

Gly Gly Ser Leu Arg Leu Ser Cys Ala Ala Ser Gly Phe Asn Ile Lys
145                 150                 155                 160

Asp Thr Tyr Ile His Trp Val Arg Gln Ala Pro Gly Lys Gly Leu Glu
            165                 170                 175

Trp Val Ala Arg Ile Tyr Pro Thr Asn Gly Tyr Thr Arg Tyr Ala Asp
            180                 185                 190

Ser Val Lys Gly Arg Phe Thr Ile Ser Ala Asp Thr Ser Lys Asn Thr
        195                 200                 205

Ala Tyr Leu Gln Met Asn Ser Leu Arg Ala Glu Asp Thr Ala Val Tyr
210                 215                 220

Tyr Cys Ala Arg Glu Leu Phe Asp Ser Ser Tyr Phe Ser Trp Phe Asp
225                 230                 235                 240

Phe Tyr Asp Tyr Tyr Asp Tyr Trp Gly Gln Gly Thr Leu Val Thr Val
                245                 250                 255

Ser Ser Ala Ala Ala His Lys Thr His Thr Cys Pro Pro Cys Pro Ala
        260                 265                 270

Pro Glu Leu Leu Gly Gly Pro Ser Val Phe Leu Phe Pro Pro Lys Pro
        275                 280                 285

Lys Asp Thr Leu Met Ile Ser Arg Thr Pro Glu Val Thr Cys Val Val
290                 295                 300

Val Asp Val Ser His Glu Asp Pro Glu Val Lys Phe Asn Trp Tyr Val
305                 310                 315                 320

Asp Gly Val Glu Val His Asn Ala Lys Thr Lys Pro Arg Glu Glu Gln
                325                 330                 335

Tyr Asn Ser Thr Tyr Arg Val Val Ser Val Leu Thr Val Leu His Gln
            340                 345                 350

Asp Trp Leu Asn Gly Lys Glu Tyr Lys Cys Lys Val Ser Asn Lys Ala
        355                 360                 365

Leu Pro Ala Pro Ile Glu Lys Thr Ile Ser Lys Ala Lys Gly Gln Pro
370                 375                 380

Arg Glu Pro Gln Val Tyr Thr Leu Pro Pro Ser Arg Asp Glu Leu Thr
385                 390                 395                 400

Lys Asn Gln Val Ser Leu Thr Cys Leu Val Lys Gly Phe Tyr Pro Ser
                405                 410                 415

Asp Ile Ala Val Glu Trp Glu Ser Asn Gly Gln Pro Glu Asn Asn Tyr
            420                 425                 430

Lys Thr Thr Pro Pro Val Leu Asp Ser Asp Gly Ser Phe Phe Leu Tyr
        435                 440                 445

Ser Lys Leu Thr Val Asp Lys Ser Arg Trp Gln Gln Gly Asn Val Phe
450                 455                 460

Ser Cys Ser Val Met His Glu Ala Leu His Asn His Tyr Thr Gln Lys
465                 470                 475                 480

Ser Leu Ser Leu Ser Pro Gly Lys Gly Ser His His His His His His
                485                 490                 495

Lys Leu Asp Tyr Lys Asp His Asp Gly Asp Tyr Lys Asp His Asp Ile
            500                 505                 510

Asp Tyr Lys Asp Asp Asp Lys
            515                 520

<210> SEQ ID NO 13
<211> LENGTH: 107
<212> TYPE: PRT

```
<213> ORGANISM: ARTIFICIAL
<220> FEATURE:
<223> OTHER INFORMATION: Synthetic

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Val Ser Asp Ala
            20                  25                  30

Val Ser Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Asp Thr Pro Pro
                85                  90                  95

Thr Phe Gly Gln Gly Thr Lys Val Glu Ile Lys
            100                 105

<210> SEQ ID NO 14
<211> LENGTH: 107
<212> TYPE: PRT
<213> ORGANISM: ARTIFICIAL
<220> FEATURE:
<223> OTHER INFORMATION: Synthetic

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asp Ser Ala
            20                  25                  30

Val Asn Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Cys Thr Tyr Pro Pro
                85                  90                  95

Thr Phe Gly Gln Gly Thr Lys Val Glu Ile Lys
            100                 105

<210> SEQ ID NO 15
<211> LENGTH: 107
<212> TYPE: PRT
<213> ORGANISM: ARTIFICIAL
<220> FEATURE:
<223> OTHER INFORMATION: Synthetic

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Thr Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60
```

```
Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Ser Thr Tyr Pro Pro
                 85                  90                  95

Thr Phe Gly Gln Gly Thr Lys Val Glu Ile Lys
            100                 105

<210> SEQ ID NO 16
<211> LENGTH: 107
<212> TYPE: PRT
<213> ORGANISM: ARTIFICIAL
<220> FEATURE:
<223> OTHER INFORMATION: Synthetic

<400> SEQUENCE: 16

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ile Val Ser Asn Ala
                 20                  25                  30

Val Thr Trp Tyr Gln Gln Lys Pro Gly Lys Ala Pro Lys Leu Leu Ile
             35                  40                  45

Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Cys Thr Thr Pro Pro
                 85                  90                  95

Thr Phe Gly Gln Gly Thr Lys Val Glu Ile Lys
            100                 105

<210> SEQ ID NO 17
<211> LENGTH: 107
<212> TYPE: PRT
<213> ORGANISM: ARTIFICIAL
<220> FEATURE:
<223> OTHER INFORMATION: Synthetic

<400> SEQUENCE: 17

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asn Val Ser Asp Ala
                 20                  25                  30

Val Asn Trp Tyr Gln Gln Lys Pro Gly Lys Ala Pro Lys Leu Leu Ile
             35                  40                  45

Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Asn Pro Pro
                 85                  90                  95

Thr Phe Gly Gln Gly Thr Lys Val Glu Ile Lys
            100                 105

<210> SEQ ID NO 18
<211> LENGTH: 107
<212> TYPE: PRT
<213> ORGANISM: ARTIFICIAL
<220> FEATURE:
<223> OTHER INFORMATION: Synthetic
```

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ile Val Asn Tyr Ala
            20                  25                  30

Val Tyr Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Val Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 19
<211> LENGTH: 107
<212> TYPE: PRT
<213> ORGANISM: ARTIFICIAL
<220> FEATURE:
<223> OTHER INFORMATION: Synthetic

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Val Thr Ala Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Asn Thr Tyr Pro Pro
                85                  90                  95

Thr Phe Gly Gln Gly Thr Lys Val Glu Ile Lys
            100                 105

<210> SEQ ID NO 20
<211> LENGTH: 107
<212> TYPE: PRT
<213> ORGANISM: ARTIFICIAL
<220> FEATURE:
<223> OTHER INFORMATION: Synthetic

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

```
Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105
```

<210> SEQ ID NO 21
<211> LENGTH: 107
<212> TYPE: PRT
<213> ORGANISM: ARTIFICIAL
<220> FEATURE:
<223> OTHER INFORMATION: Synthetic

<400> SEQUENCE: 21

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105
```

<210> SEQ ID NO 22
<211> LENGTH: 107
<212> TYPE: PRT
<213> ORGANISM: ARTIFICIAL
<220> FEATURE:
<223> OTHER INFORMATION: Synthetic

<400> SEQUENCE: 22

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105
```

<210> SEQ ID NO 23
<211> LENGTH: 107
<212> TYPE: PRT
<213> ORGANISM: ARTIFICIAL
<220> FEATURE:
<223> OTHER INFORMATION: Synthetic

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65              70                  75                  80

Glu Asp Phe Ala Thr Tyr Tyr Cys Gln Gln His Tyr Thr Thr Pro Pro
            85                  90                  95

Thr Phe Gly Gln Gly Thr Lys Val Glu Ile Lys
            100                 105

<210> SEQ ID NO 24
<211> LENGTH: 107
<212> TYPE: PRT
<213> ORGANISM: ARTIFICIAL
<220> FEATURE:
<223> OTHER INFORMATION: Synthetic

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65              70                  75                  80

Glu Asp Phe Ala Thr Tyr Tyr Cys Gln Gln His Tyr Thr Thr Pro Pro
            85                  90                  95

Thr Phe Gly Gln Gly Thr Lys Val Glu Ile Lys
            100                 105

<210> SEQ ID NO 25
<211> LENGTH: 128
<212> TYPE: PRT
<213> ORGANISM: ARTIFICIAL
<220> FEATURE:
<223> OTHER INFORMATION: Synthetic

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Ser Pro Thr Gly Tyr Thr Arg Tyr Ala Ala Ser Val
    50                  55                  60

Lys Gly Arg Phe Thr Ile Ser Ala Asp Thr Ser Lys Asn Thr Ala Tyr
65              70                  75                  80

Leu Gln Met Asn Ser Leu Arg Ala Glu Asp Thr Ala Val Tyr Tyr Cys
            85                  90                  95

Ala Arg Asp Trp Phe Asp Ala Ala Ser Phe Ala Trp Phe Asp Phe Tyr
            100                 105                 110

Asp Tyr Ser Asp Tyr Trp Gly Gln Gly Thr Leu Val Thr Val Ser Ser
            115                 120                 125

<210> SEQ ID NO 26
<211> LENGTH: 128
<212> TYPE: PRT
<213> ORGANISM: ARTIFICIAL
<220> FEATURE:
<223> OTHER INFORMATION: Synthetic

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
            35                  40                  45

Ala Arg Ile Ser Pro Tyr Asp Gly Asn Thr Arg Tyr Ala Ala Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ala Arg Asp Trp Phe Asp Ala Ala Ser Phe Ala Trp Phe Asp Phe Tyr
            100                 105                 110

Asp Tyr Ser Asp Tyr Trp Gly Gln Gly Thr Leu Val Thr Val Ser Ser
            115                 120                 125

<210> SEQ ID NO 27
<211> LENGTH: 128
<212> TYPE: PRT
<213> ORGANISM: ARTIFICIAL
<220> FEATURE:
<223> OTHER INFORMATION: Synthetic

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
            35                  40                  45

Ala Arg Ile Ser Pro Ala Gly Gly Thr Thr Arg Tyr Ala Ala Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ala Arg Asp Trp Phe Asp Ala Ala Ser Phe Ala Trp Phe Asp Phe Tyr
            100                 105                 110

Asp Tyr Ser Asp Tyr Trp Gly Gln Gly Thr Leu Val Thr Val Ser Ser
            115                 120                 125

<210> SEQ ID NO 28
<211> LENGTH: 128
<212> TYPE: PRT

```
<213> ORGANISM: ARTIFICIAL
<220> FEATURE:
<223> OTHER INFORMATION: Synthetic

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Asp Gly Gly Asn Thr Arg Tyr Ala Gly Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Val Arg Asp Trp Phe Asp Ala Ala Ser Phe Ala Trp Phe Asp Phe Tyr
            100                 105                 110

Asp Tyr Ser Asp Tyr Trp Gly Gln Gly Thr Leu Val Thr Val Ser Ser
        115                 120                 125

<210> SEQ ID NO 29
<211> LENGTH: 128
<212> TYPE: PRT
<213> ORGANISM: ARTIFICIAL
<220> FEATURE:
<223> OTHER INFORMATION: Synthetic

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Thr Pro Thr Asp Gly Thr Thr Arg Tyr Ala Val Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Trp Tyr Glu Ala Ser Tyr Tyr Asp Trp Phe Asp Tyr Phe
            100                 105                 110

Asp Phe Ser Asp Tyr Trp Gly Gln Gly Thr Leu Val Thr Val Ser Ser
        115                 120                 125

<210> SEQ ID NO 30
<211> LENGTH: 128
<212> TYPE: PRT
<213> ORGANISM: ARTIFICIAL
<220> FEATURE:
<223> OTHER INFORMATION: Synthetic

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30
```

Tyr Ile His Trp Val Arg Gln Ala Pro Gly Lys Gly Leu Glu Trp Val
        35                  40                  45

Ala Arg Ile Ala Pro Thr Asn Gly Thr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Trp Tyr Glu Ala Ser Tyr Tyr Asp Trp Phe Asp Tyr Phe
            100                 105                 110

Asp Phe Ser Asp Tyr Trp Gly Gln Gly Thr Leu Val Thr Val Ser Ser
        115                 120                 125

<210> SEQ ID NO 31
<211> LENGTH: 128
<212> TYPE: PRT
<213> ORGANISM: ARTIFICIAL
<220> FEATURE:
<223> OTHER INFORMATION: Synthetic

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Ala Pro Thr Ser Gly Tyr Thr Arg Tyr Ala Val Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Trp Tyr Glu Ala Ser Tyr Tyr Asp Trp Phe Asp Tyr Phe
            100                 105                 110

Asp Phe Ser Asp Tyr Trp Gly Gln Gly Thr Leu Val Thr Val Ser Ser
        115                 120                 125

<210> SEQ ID NO 32
<211> LENGTH: 128
<212> TYPE: PRT
<213> ORGANISM: ARTIFICIAL
<220> FEATURE:
<223> OTHER INFORMATION: Synthetic

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys

```
                     85                  90                  95
Ala Arg Glu Val Tyr Asp Thr Ser Tyr Phe Phe Trp Phe Asp Tyr Tyr
                100                 105                 110

Asp Tyr Tyr Asp Tyr Trp Gly Gln Gly Thr Leu Val Thr Val Ser Ser
        115                 120                 125

<210> SEQ ID NO 33
<211> LENGTH: 128
<212> TYPE: PRT
<213> ORGANISM: ARTIFICIAL
<220> FEATURE:
<223> OTHER INFORMATION: Synthetic

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Trp Phe Asp Ala Ala Ser Phe Ala Trp Phe Asp Phe Tyr
                100                 105                 110

Asp Tyr Ser Asp Tyr Trp Gly Gln Gly Thr Leu Val Thr Val Ser Ser
        115                 120                 125

<210> SEQ ID NO 34
<211> LENGTH: 128
<212> TYPE: PRT
<213> ORGANISM: ARTIFICIAL
<220> FEATURE:
<223> OTHER INFORMATION: Synthetic

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Trp Tyr Glu Ala Ser Tyr Tyr Asp Trp Phe Asp Tyr Phe
                100                 105                 110

Asp Phe Ser Asp Tyr Trp Gly Gln Gly Thr Leu Val Thr Val Ser Ser
        115                 120                 125

<210> SEQ ID NO 35
<211> LENGTH: 128
```

<212> TYPE: PRT
<213> ORGANISM: ARTIFICIAL
<220> FEATURE:
<223> OTHER INFORMATION: Synthetic

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Trp Ser Asp Ala Thr Tyr Phe Tyr Trp Phe Asp Phe Tyr
            100                 105                 110

Asp Tyr Ser Asp Tyr Trp Gly Gln Gly Thr Leu Val Thr Val Ser Ser
        115                 120                 125

<210> SEQ ID NO 36
<211> LENGTH: 128
<212> TYPE: PRT
<213> ORGANISM: ARTIFICIAL
<220> FEATURE:
<223> OTHER INFORMATION: Synthetic

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Leu Phe Asp Ser Ser Tyr Phe Ser Trp Phe Asp Phe Tyr
            100                 105                 110

Asp Tyr Tyr Asp Tyr Trp Gly Gln Gly Thr Leu Val Thr Val Ser Ser
        115                 120                 125

<210> SEQ ID NO 37
<211> LENGTH: 19
<212> TYPE: PRT
<213> ORGANISM: ARTIFICIAL
<220> FEATURE:
<223> OTHER INFORMATION: Synthetic

<400> SEQUENCE: 37

Asp Trp Phe Asp Ala Ala Ser Phe Ala Trp Phe Asp Phe Tyr Asp Tyr
1               5                   10                  15

Ser Asp Tyr

```
<210> SEQ ID NO 38
<211> LENGTH: 17
<212> TYPE: PRT
<213> ORGANISM: ARTIFICIAL
<220> FEATURE:
<223> OTHER INFORMATION: Synthetic

<400> SEQUENCE: 38

Arg Ile Ser Pro Thr Gly Gly Tyr Thr Arg Tyr Ala Ala Ser Val Lys
1               5                   10                  15

Gly

<210> SEQ ID NO 39
<211> LENGTH: 5
<212> TYPE: PRT
<213> ORGANISM: ARTIFICIAL
<220> FEATURE:
<223> OTHER INFORMATION: Synthetic

<400> SEQUENCE: 39

Asp Thr Tyr Ile His
1               5

<210> SEQ ID NO 40
<211> LENGTH: 9
<212> TYPE: PRT
<213> ORGANISM: ARTIFICIAL
<220> FEATURE:
<223> OTHER INFORMATION: Synthetic

<400> SEQUENCE: 40

Gln Gln His Asp Thr Thr Pro Pro Thr
1               5

<210> SEQ ID NO 41
<211> LENGTH: 7
<212> TYPE: PRT
<213> ORGANISM: ARTIFICIAL
<220> FEATURE:
<223> OTHER INFORMATION: Synthetic

<400> SEQUENCE: 41

Ser Ala Ser Phe Leu Tyr Ser
1               5

<210> SEQ ID NO 42
<211> LENGTH: 11
<212> TYPE: PRT
<213> ORGANISM: ARTIFICIAL
<220> FEATURE:
<223> OTHER INFORMATION: Synthetic

<400> SEQUENCE: 42

Arg Ala Ser Gln Gly Val Ser Asp Ala Val Ser
1               5                   10

<210> SEQ ID NO 43
<211> LENGTH: 19
<212> TYPE: PRT
<213> ORGANISM: ARTIFICIAL
<220> FEATURE:
<223> OTHER INFORMATION: Synthetic

<400> SEQUENCE: 43

Asp Trp Phe Asp Ala Ala Ser Phe Ala Trp Phe Asp Phe Tyr Asp Tyr
```

```
                     1               5                  10                  15

Ser Asp Tyr

<210> SEQ ID NO 44
<211> LENGTH: 17
<212> TYPE: PRT
<213> ORGANISM: ARTIFICIAL
<220> FEATURE:
<223> OTHER INFORMATION: Synthetic

<400> SEQUENCE: 44

Arg Ile Ser Pro Tyr Asp Gly Asn Thr Arg Tyr Ala Ala Ser Val Lys
1               5                   10                  15

Gly

<210> SEQ ID NO 45
<211> LENGTH: 5
<212> TYPE: PRT
<213> ORGANISM: ARTIFICIAL
<220> FEATURE:
<223> OTHER INFORMATION: Synthetic

<400> SEQUENCE: 45

Asp Thr Tyr Ile His
1               5

<210> SEQ ID NO 46
<211> LENGTH: 9
<212> TYPE: PRT
<213> ORGANISM: ARTIFICIAL
<220> FEATURE:
<223> OTHER INFORMATION: Synthetic

<400> SEQUENCE: 46

Gln Gln His Cys Thr Tyr Pro Pro Thr
1               5

<210> SEQ ID NO 47
<211> LENGTH: 7
<212> TYPE: PRT
<213> ORGANISM: ARTIFICIAL
<220> FEATURE:
<223> OTHER INFORMATION: Synthetic

<400> SEQUENCE: 47

Ser Ala Ser Phe Leu Tyr Ser
1               5

<210> SEQ ID NO 48
<211> LENGTH: 11
<212> TYPE: PRT
<213> ORGANISM: ARTIFICIAL
<220> FEATURE:
<223> OTHER INFORMATION: Synthetic

<400> SEQUENCE: 48

Arg Ala Ser Gln Asp Val Asp Ser Ala Val Asn
1               5                   10

<210> SEQ ID NO 49
<211> LENGTH: 19
<212> TYPE: PRT
<213> ORGANISM: ARTIFICIAL
<220> FEATURE:
<223> OTHER INFORMATION: Synthetic
```

```
<400> SEQUENCE: 49

Asp Trp Phe Asp Ala Ala Ser Phe Ala Trp Phe Asp Phe Tyr Asp Tyr
1               5                   10                  15

Ser Asp Tyr

<210> SEQ ID NO 50
<211> LENGTH: 17
<212> TYPE: PRT
<213> ORGANISM: ARTIFICIAL
<220> FEATURE:
<223> OTHER INFORMATION: Synthetic

<400> SEQUENCE: 50

Arg Ile Ser Pro Ala Gly Gly Thr Thr Arg Tyr Ala Ala Ser Val Lys
1               5                   10                  15

Gly

<210> SEQ ID NO 51
<211> LENGTH: 5
<212> TYPE: PRT
<213> ORGANISM: ARTIFICIAL
<220> FEATURE:
<223> OTHER INFORMATION: Synthetic

<400> SEQUENCE: 51

Asp Thr Tyr Ile His
1               5

<210> SEQ ID NO 52
<211> LENGTH: 9
<212> TYPE: PRT
<213> ORGANISM: ARTIFICIAL
<220> FEATURE:
<223> OTHER INFORMATION: Synthetic

<400> SEQUENCE: 52

Gln Gln His Ser Thr Tyr Pro Pro Thr
1               5

<210> SEQ ID NO 53
<211> LENGTH: 7
<212> TYPE: PRT
<213> ORGANISM: ARTIFICIAL
<220> FEATURE:
<223> OTHER INFORMATION: Synthetic

<400> SEQUENCE: 53

Ser Ala Ser Phe Leu Tyr Ser
1               5

<210> SEQ ID NO 54
<211> LENGTH: 11
<212> TYPE: PRT
<213> ORGANISM: ARTIFICIAL
<220> FEATURE:
<223> OTHER INFORMATION: Synthetic

<400> SEQUENCE: 54

Arg Ala Ser Gln Asp Val Ser Thr Ala Val Thr
1               5                   10

<210> SEQ ID NO 55
<211> LENGTH: 19
<212> TYPE: PRT
<213> ORGANISM: ARTIFICIAL
```

```
<220> FEATURE:
<223> OTHER INFORMATION: Synthetic

<400> SEQUENCE: 55

Asp Trp Phe Asp Ala Ala Ser Phe Ala Trp Phe Asp Phe Tyr Asp Tyr
1               5                   10                  15

Ser Asp Tyr

<210> SEQ ID NO 56
<211> LENGTH: 17
<212> TYPE: PRT
<213> ORGANISM: ARTIFICIAL
<220> FEATURE:
<223> OTHER INFORMATION: Synthetic

<400> SEQUENCE: 56

Arg Ile Tyr Pro Asp Gly Gly Asn Thr Arg Tyr Ala Gly Ser Val Lys
1               5                   10                  15

Gly

<210> SEQ ID NO 57
<211> LENGTH: 5
<212> TYPE: PRT
<213> ORGANISM: ARTIFICIAL
<220> FEATURE:
<223> OTHER INFORMATION: Synthetic

<400> SEQUENCE: 57

Asp Thr Tyr Ile His
1               5

<210> SEQ ID NO 58
<211> LENGTH: 9
<212> TYPE: PRT
<213> ORGANISM: ARTIFICIAL
<220> FEATURE:
<223> OTHER INFORMATION: Synthetic

<400> SEQUENCE: 58

Gln Gln His Cys Thr Thr Pro Pro Thr
1               5

<210> SEQ ID NO 59
<211> LENGTH: 7
<212> TYPE: PRT
<213> ORGANISM: ARTIFICIAL
<220> FEATURE:
<223> OTHER INFORMATION: Synthetic

<400> SEQUENCE: 59

Ser Ala Ser Phe Leu Tyr Ser
1               5

<210> SEQ ID NO 60
<211> LENGTH: 11
<212> TYPE: PRT
<213> ORGANISM: ARTIFICIAL
<220> FEATURE:
<223> OTHER INFORMATION: Synthetic

<400> SEQUENCE: 60

Arg Ala Ser Gln Ile Val Ser Asn Ala Val Thr
1               5                   10

<210> SEQ ID NO 61
```

```
<211> LENGTH: 19
<212> TYPE: PRT
<213> ORGANISM: ARTIFICIAL
<220> FEATURE:
<223> OTHER INFORMATION: Synthetic

<400> SEQUENCE: 61

Glu Trp Tyr Glu Ala Ser Tyr Tyr Asp Trp Phe Asp Tyr Phe Asp Phe
1               5                   10                  15
Ser Asp Tyr

<210> SEQ ID NO 62
<211> LENGTH: 17
<212> TYPE: PRT
<213> ORGANISM: ARTIFICIAL
<220> FEATURE:
<223> OTHER INFORMATION: Synthetic

<400> SEQUENCE: 62

Arg Ile Thr Pro Thr Asp Gly Thr Thr Arg Tyr Ala Val Ser Val Lys
1               5                   10                  15
Gly

<210> SEQ ID NO 63
<211> LENGTH: 5
<212> TYPE: PRT
<213> ORGANISM: ARTIFICIAL
<220> FEATURE:
<223> OTHER INFORMATION: Synthetic

<400> SEQUENCE: 63

Asp Thr Tyr Ile His
1               5

<210> SEQ ID NO 64
<211> LENGTH: 9
<212> TYPE: PRT
<213> ORGANISM: ARTIFICIAL
<220> FEATURE:
<223> OTHER INFORMATION: Synthetic

<400> SEQUENCE: 64

Gln Gln His Tyr Thr Asn Pro Pro Thr
1               5

<210> SEQ ID NO 65
<211> LENGTH: 7
<212> TYPE: PRT
<213> ORGANISM: ARTIFICIAL
<220> FEATURE:
<223> OTHER INFORMATION: Synthetic

<400> SEQUENCE: 65

Ser Ala Ser Phe Leu Tyr Ser
1               5

<210> SEQ ID NO 66
<211> LENGTH: 11
<212> TYPE: PRT
<213> ORGANISM: ARTIFICIAL
<220> FEATURE:
<223> OTHER INFORMATION: Synthetic

<400> SEQUENCE: 66

Arg Ala Ser Gln Asn Val Ser Asp Ala Val Asn
1               5                   10
```

<210> SEQ ID NO 67
<211> LENGTH: 19
<212> TYPE: PRT
<213> ORGANISM: ARTIFICIAL
<220> FEATURE:
<223> OTHER INFORMATION: Synthetic

<400> SEQUENCE: 67

Glu Trp Tyr Glu Ala Ser Tyr Tyr Asp Trp Phe Asp Tyr Phe Asp Phe
1               5                   10                  15

Ser Asp Tyr

<210> SEQ ID NO 68
<211> LENGTH: 17
<212> TYPE: PRT
<213> ORGANISM: ARTIFICIAL
<220> FEATURE:
<223> OTHER INFORMATION: Synthetic

<400> SEQUENCE: 68

Arg Ile Ala Pro Thr Asn Gly Thr Thr Arg Tyr Ala Asp Ser Val Lys
1               5                   10                  15

Gly

<210> SEQ ID NO 69
<211> LENGTH: 5
<212> TYPE: PRT
<213> ORGANISM: ARTIFICIAL
<220> FEATURE:
<223> OTHER INFORMATION: Synthetic

<400> SEQUENCE: 69

Asp Thr Tyr Ile His
1               5

<210> SEQ ID NO 70
<211> LENGTH: 9
<212> TYPE: PRT
<213> ORGANISM: ARTIFICIAL
<220> FEATURE:
<223> OTHER INFORMATION: Synthetic

<400> SEQUENCE: 70

Gln Gln His Tyr Thr Thr Pro Pro Thr
1               5

<210> SEQ ID NO 71
<211> LENGTH: 7
<212> TYPE: PRT
<213> ORGANISM: ARTIFICIAL
<220> FEATURE:
<223> OTHER INFORMATION: Synthetic

<400> SEQUENCE: 71

Ser Ala Ser Phe Leu Tyr Ser
1               5

<210> SEQ ID NO 72
<211> LENGTH: 11
<212> TYPE: PRT
<213> ORGANISM: ARTIFICIAL
<220> FEATURE:
<223> OTHER INFORMATION: Synthetic

<400> SEQUENCE: 72

```
Arg Ala Ser Gln Ile Val Asn Tyr Ala Val Tyr
1               5                   10
```

<210> SEQ ID NO 73
<211> LENGTH: 19
<212> TYPE: PRT
<213> ORGANISM: ARTIFICIAL
<220> FEATURE:
<223> OTHER INFORMATION: Synthetic

<400> SEQUENCE: 73

```
Glu Trp Tyr Glu Ala Ser Tyr Tyr Asp Trp Phe Asp Tyr Phe Asp Phe
1               5                   10                  15

Ser Asp Tyr
```

<210> SEQ ID NO 74
<211> LENGTH: 17
<212> TYPE: PRT
<213> ORGANISM: ARTIFICIAL
<220> FEATURE:
<223> OTHER INFORMATION: Synthetic

<400> SEQUENCE: 74

```
Arg Ile Ala Pro Thr Ser Gly Tyr Thr Arg Tyr Ala Val Ser Val Lys
1               5                   10                  15

Gly
```

<210> SEQ ID NO 75
<211> LENGTH: 5
<212> TYPE: PRT
<213> ORGANISM: ARTIFICIAL
<220> FEATURE:
<223> OTHER INFORMATION: Synthetic

<400> SEQUENCE: 75

```
Asp Thr Tyr Ile His
1               5
```

<210> SEQ ID NO 76
<211> LENGTH: 9
<212> TYPE: PRT
<213> ORGANISM: ARTIFICIAL
<220> FEATURE:
<223> OTHER INFORMATION: Synthetic

<400> SEQUENCE: 76

```
Gln Gln His Asn Thr Tyr Pro Pro Thr
1               5
```

<210> SEQ ID NO 77
<211> LENGTH: 7
<212> TYPE: PRT
<213> ORGANISM: ARTIFICIAL
<220> FEATURE:
<223> OTHER INFORMATION: Synthetic

<400> SEQUENCE: 77

```
Ser Ala Ser Phe Leu Tyr Ser
1               5
```

<210> SEQ ID NO 78
<211> LENGTH: 11
<212> TYPE: PRT
<213> ORGANISM: ARTIFICIAL
<220> FEATURE:

```
<223> OTHER INFORMATION: Synthetic

<400> SEQUENCE: 78

Arg Ala Ser Gln Gly Val Thr Ala Ala Val Ala
1               5                   10

<210> SEQ ID NO 79
<211> LENGTH: 19
<212> TYPE: PRT
<213> ORGANISM: ARTIFICIAL
<220> FEATURE:
<223> OTHER INFORMATION: Synthetic

<400> SEQUENCE: 79

Glu Val Tyr Asp Thr Ser Tyr Phe Phe Trp Phe Asp Tyr Tyr Asp Tyr
1               5                   10                  15

Tyr Asp Tyr

<210> SEQ ID NO 80
<211> LENGTH: 16
<212> TYPE: PRT
<213> ORGANISM: ARTIFICIAL
<220> FEATURE:
<223> OTHER INFORMATION: Synthetic

<400> SEQUENCE: 80

Arg Ile Tyr Pro Thr Asn Gly Tyr Thr Arg Tyr Ala Asp Ser Val Lys
1               5                   10                  15

<210> SEQ ID NO 81
<211> LENGTH: 5
<212> TYPE: PRT
<213> ORGANISM: ARTIFICIAL
<220> FEATURE:
<223> OTHER INFORMATION: Synthetic

<400> SEQUENCE: 81

Asp Thr Tyr Ile His
1               5

<210> SEQ ID NO 82
<211> LENGTH: 9
<212> TYPE: PRT
<213> ORGANISM: ARTIFICIAL
<220> FEATURE:
<223> OTHER INFORMATION: Synthetic

<400> SEQUENCE: 82

Gln Gln His Tyr Thr Thr Pro Pro Thr
1               5

<210> SEQ ID NO 83
<211> LENGTH: 7
<212> TYPE: PRT
<213> ORGANISM: ARTIFICIAL
<220> FEATURE:
<223> OTHER INFORMATION: Synthetic

<400> SEQUENCE: 83

Ser Ala Ser Phe Leu Tyr Ser
1               5

<210> SEQ ID NO 84
<211> LENGTH: 11
<212> TYPE: PRT
<213> ORGANISM: ARTIFICIAL
```

-continued

<220> FEATURE:
<223> OTHER INFORMATION: Synthetic

<400> SEQUENCE: 84

Arg Ala Ser Gln Asp Val Asn Thr Ala Val Ala
1               5                   10

<210> SEQ ID NO 85
<211> LENGTH: 19
<212> TYPE: PRT
<213> ORGANISM: ARTIFICIAL
<220> FEATURE:
<223> OTHER INFORMATION: Synthetic

<400> SEQUENCE: 85

Asp Trp Phe Asp Ala Ala Ser Phe Ala Trp Phe Asp Phe Tyr Asp Tyr
1               5                   10                  15

Ser Asp Tyr

<210> SEQ ID NO 86
<211> LENGTH: 17
<212> TYPE: PRT
<213> ORGANISM: ARTIFICIAL
<220> FEATURE:
<223> OTHER INFORMATION: Synthetic

<400> SEQUENCE: 86

Arg Ile Tyr Pro Thr Asn Gly Tyr Thr Arg Tyr Ala Asp Ser Val Lys
1               5                   10                  15

Gly

<210> SEQ ID NO 87
<211> LENGTH: 5
<212> TYPE: PRT
<213> ORGANISM: ARTIFICIAL
<220> FEATURE:
<223> OTHER INFORMATION: Synthetic

<400> SEQUENCE: 87

Asp Thr Tyr Ile His
1               5

<210> SEQ ID NO 88
<211> LENGTH: 9
<212> TYPE: PRT
<213> ORGANISM: ARTIFICIAL
<220> FEATURE:
<223> OTHER INFORMATION: Synthetic

<400> SEQUENCE: 88

Gln Gln His Tyr Thr Thr Pro Pro Thr
1               5

<210> SEQ ID NO 89
<211> LENGTH: 7
<212> TYPE: PRT
<213> ORGANISM: ARTIFICIAL
<220> FEATURE:
<223> OTHER INFORMATION: Synthetic

<400> SEQUENCE: 89

Ser Ala Ser Phe Leu Tyr Ser
1               5

<210> SEQ ID NO 90

```
<211> LENGTH: 11
<212> TYPE: PRT
<213> ORGANISM: ARTIFICIAL
<220> FEATURE:
<223> OTHER INFORMATION: Synthetic

<400> SEQUENCE: 90

Arg Ala Ser Gln Asp Val Asn Thr Ala Val Ala
1               5                   10

<210> SEQ ID NO 91
<211> LENGTH: 19
<212> TYPE: PRT
<213> ORGANISM: ARTIFICIAL
<220> FEATURE:
<223> OTHER INFORMATION: Synthetic

<400> SEQUENCE: 91

Glu Trp Tyr Glu Ala Ser Tyr Tyr Asp Trp Phe Asp Tyr Phe Asp Phe
1               5                   10                  15

Ser Asp Tyr

<210> SEQ ID NO 92
<211> LENGTH: 17
<212> TYPE: PRT
<213> ORGANISM: ARTIFICIAL
<220> FEATURE:
<223> OTHER INFORMATION: Synthetic

<400> SEQUENCE: 92

Arg Ile Tyr Pro Thr Asn Gly Tyr Thr Arg Tyr Ala Asp Ser Val Lys
1               5                   10                  15

Gly

<210> SEQ ID NO 93
<211> LENGTH: 5
<212> TYPE: PRT
<213> ORGANISM: ARTIFICIAL
<220> FEATURE:
<223> OTHER INFORMATION: Synthetic

<400> SEQUENCE: 93

Asp Thr Tyr Ile His
1               5

<210> SEQ ID NO 94
<211> LENGTH: 9
<212> TYPE: PRT
<213> ORGANISM: ARTIFICIAL
<220> FEATURE:
<223> OTHER INFORMATION: Synthetic

<400> SEQUENCE: 94

Gln Gln His Tyr Thr Thr Pro Pro Thr
1               5

<210> SEQ ID NO 95
<211> LENGTH: 7
<212> TYPE: PRT
<213> ORGANISM: ARTIFICIAL
<220> FEATURE:
<223> OTHER INFORMATION: Synthetic

<400> SEQUENCE: 95

Ser Ala Ser Phe Leu Tyr Ser
1               5
```

```
<210> SEQ ID NO 96
<211> LENGTH: 11
<212> TYPE: PRT
<213> ORGANISM: ARTIFICIAL
<220> FEATURE:
<223> OTHER INFORMATION: Synthetic

<400> SEQUENCE: 96

Arg Ala Ser Gln Asp Val Asn Thr Ala Val Ala
1               5                   10

<210> SEQ ID NO 97
<211> LENGTH: 19
<212> TYPE: PRT
<213> ORGANISM: ARTIFICIAL
<220> FEATURE:
<223> OTHER INFORMATION: Synthetic

<400> SEQUENCE: 97

Glu Trp Ser Asp Ala Thr Tyr Phe Tyr Trp Phe Asp Phe Tyr Asp Tyr
1               5                   10                  15

Ser Asp Tyr

<210> SEQ ID NO 98
<211> LENGTH: 17
<212> TYPE: PRT
<213> ORGANISM: ARTIFICIAL
<220> FEATURE:
<223> OTHER INFORMATION: Synthetic

<400> SEQUENCE: 98

Arg Ile Tyr Pro Thr Asn Gly Tyr Thr Arg Tyr Ala Asp Ser Val Lys
1               5                   10                  15

Gly

<210> SEQ ID NO 99
<211> LENGTH: 5
<212> TYPE: PRT
<213> ORGANISM: ARTIFICIAL
<220> FEATURE:
<223> OTHER INFORMATION: Synthetic

<400> SEQUENCE: 99

Asp Thr Tyr Ile His
1               5

<210> SEQ ID NO 100
<211> LENGTH: 9
<212> TYPE: PRT
<213> ORGANISM: ARTIFICIAL
<220> FEATURE:
<223> OTHER INFORMATION: Synthetic

<400> SEQUENCE: 100

Gln Gln His Tyr Thr Thr Pro Pro Thr
1               5

<210> SEQ ID NO 101
<211> LENGTH: 7
<212> TYPE: PRT
<213> ORGANISM: ARTIFICIAL
<220> FEATURE:
<223> OTHER INFORMATION: Synthetic

<400> SEQUENCE: 101
```

Ser Ala Ser Phe Leu Tyr Ser
1               5

<210> SEQ ID NO 102
<211> LENGTH: 11
<212> TYPE: PRT
<213> ORGANISM: ARTIFICIAL
<220> FEATURE:
<223> OTHER INFORMATION: Synthetic

<400> SEQUENCE: 102

Arg Ala Ser Gln Asp Val Asn Thr Ala Val Ala
1               5                   10

<210> SEQ ID NO 103
<211> LENGTH: 19
<212> TYPE: PRT
<213> ORGANISM: ARTIFICIAL
<220> FEATURE:
<223> OTHER INFORMATION: Synthetic

<400> SEQUENCE: 103

Glu Leu Phe Asp Ser Ser Tyr Phe Ser Trp Phe Asp Phe Tyr Asp Tyr
1               5                   10                  15

Tyr Asp Tyr

<210> SEQ ID NO 104
<211> LENGTH: 17
<212> TYPE: PRT
<213> ORGANISM: ARTIFICIAL
<220> FEATURE:
<223> OTHER INFORMATION: Synthetic

<400> SEQUENCE: 104

Arg Ile Tyr Pro Thr Asn Gly Tyr Thr Arg Tyr Ala Asp Ser Val Lys
1               5                   10                  15

Gly

<210> SEQ ID NO 105
<211> LENGTH: 5
<212> TYPE: PRT
<213> ORGANISM: ARTIFICIAL
<220> FEATURE:
<223> OTHER INFORMATION: Synthetic

<400> SEQUENCE: 105

Asp Thr Tyr Ile His
1               5

<210> SEQ ID NO 106
<211> LENGTH: 9
<212> TYPE: PRT
<213> ORGANISM: ARTIFICIAL
<220> FEATURE:
<223> OTHER INFORMATION: Synthetic

<400> SEQUENCE: 106

Gln Gln His Tyr Thr Thr Pro Pro Thr
1               5

<210> SEQ ID NO 107
<211> LENGTH: 7
<212> TYPE: PRT
<213> ORGANISM: ARTIFICIAL
<220> FEATURE:

-continued

<223> OTHER INFORMATION: Synthetic

<400> SEQUENCE: 107

Ser Ala Ser Phe Leu Tyr Ser
1               5

<210> SEQ ID NO 108
<211> LENGTH: 11
<212> TYPE: PRT
<213> ORGANISM: ARTIFICIAL
<220> FEATURE:
<223> OTHER INFORMATION: Synthetic

<400> SEQUENCE: 108

Arg Ala Ser Gln Asp Val Asn Thr Ala Val Ala
1               5                   10

<210> SEQ ID NO 109
<211> LENGTH: 520
<212> TYPE: PRT
<213> ORGANISM: ARTIFICIAL
<220> FEATURE:
<223> OTHER INFORMATION: Synthetic

<400> SEQUENCE: 109

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ala Ala Ala
            20                  25                  30

Val Ala Trp Tyr Gln Gln Lys Pro Asp Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Asn Thr Tyr Pro Pro
                85                  90                  95

Thr Phe Gly Gln Gly Thr Lys Val Glu Ile Lys Arg Thr Ser Pro Asn
            100                 105                 110

Ser Ala Ser His Ser Gly Ser Ala Pro Gln Thr Ser Ser Ala Pro Gly
        115                 120                 125

Ser Gln Glu Val Gln Leu Val Glu Ser Gly Gly Leu Val Gln Pro
    130                 135                 140

Gly Gly Ser Leu Arg Leu Ser Cys Ala Ala Ser Gly Phe Asn Ile Lys
145                 150                 155                 160

Asp Thr Tyr Ile His Trp Val Arg Gln Ala Pro Gly Lys Gly Leu Glu
                165                 170                 175

Trp Val Ala Arg Ile Ser Pro Ser Ser Gly Ser Thr Arg Tyr Ala Gly
            180                 185                 190

Ser Val Lys Gly Arg Phe Thr Ile Ser Ala Asp Thr Ser Lys Asn Thr
        195                 200                 205

Ala Tyr Leu Gln Met Asn Ser Leu Arg Ala Glu Asp Thr Ala Val Tyr
    210                 215                 220

Tyr Cys Ala Arg Glu Trp Tyr Glu Ala Ser Tyr Tyr Asp Trp Phe Asp
225                 230                 235                 240

Tyr Phe Asp Phe Ser Asp Tyr Trp Gly Gln Gly Thr Leu Val Thr Val
                245                 250                 255

Ser Ser Ala Ala Ala His Lys Thr His Thr Cys Pro Pro Cys Pro Ala

```
                    260                 265                 270
Pro Glu Leu Leu Gly Pro Ser Val Phe Leu Phe Pro Pro Lys Pro
            275                 280                 285

Lys Asp Thr Leu Met Ile Ser Arg Thr Pro Glu Val Thr Cys Val Val
    290                 295                 300

Val Asp Val Ser His Glu Asp Pro Glu Val Lys Phe Asn Trp Tyr Val
305                 310                 315                 320

Asp Gly Val Glu Val His Asn Ala Lys Thr Lys Pro Arg Glu Glu Gln
                325                 330                 335

Tyr Asn Ser Thr Tyr Arg Val Val Ser Val Leu Thr Val Leu His Gln
            340                 345                 350

Asp Trp Leu Asn Gly Lys Glu Tyr Lys Cys Lys Val Ser Asn Lys Ala
        355                 360                 365

Leu Pro Ala Pro Ile Glu Lys Thr Ile Ser Lys Ala Lys Gly Gln Pro
    370                 375                 380

Arg Glu Pro Gln Val Tyr Thr Leu Pro Pro Ser Arg Asp Glu Leu Thr
385                 390                 395                 400

Lys Asn Gln Val Ser Leu Thr Cys Leu Val Lys Gly Phe Tyr Pro Ser
                405                 410                 415

Asp Ile Ala Val Glu Trp Glu Ser Asn Gly Gln Pro Glu Asn Asn Tyr
            420                 425                 430

Lys Thr Thr Pro Pro Val Leu Asp Ser Asp Gly Ser Phe Phe Leu Tyr
        435                 440                 445

Ser Lys Leu Thr Val Asp Lys Ser Arg Trp Gln Gln Gly Asn Val Phe
    450                 455                 460

Ser Cys Ser Val Met His Glu Ala Leu His Asn His Tyr Thr Gln Lys
465                 470                 475                 480

Ser Leu Ser Leu Ser Pro Gly Lys Gly Ser His His His His His His
                485                 490                 495

Lys Leu Asp Tyr Lys Asp His Asp Gly Asp Tyr Lys Asp His Asp Ile
            500                 505                 510

Asp Tyr Lys Asp Asp Asp Asp Lys
        515                 520

<210> SEQ ID NO 110
<211> LENGTH: 520
<212> TYPE: PRT
<213> ORGANISM: ARTIFICIAL
<220> FEATURE:
<223> OTHER INFORMATION: Synthetic

<400> SEQUENCE: 110

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Asp Tyr Ala
            20                  25                  30

Val Ser Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Asn Thr Thr Pro Pro
                85                  90                  95

Thr Phe Gly Gln Gly Thr Lys Val Glu Ile Lys Arg Thr Ser Pro Asn
```

```
            100                 105                 110
Ser Ala Ser His Ser Gly Ser Ala Pro Gln Thr Ser Ser Ala Pro Gly
            115                 120                 125

Ser Gln Glu Val Gln Leu Val Glu Ser Gly Gly Gly Leu Val Gln Pro
            130                 135                 140

Gly Gly Ser Leu Arg Leu Ser Cys Ala Ala Ser Gly Phe Asn Ile Lys
145                 150                 155                 160

Asp Thr Tyr Ile His Trp Val Arg Gln Ala Pro Gly Lys Gly Leu Glu
                165                 170                 175

Trp Val Ala Arg Ile Ala Pro Asp Asn Gly Thr Thr Arg Tyr Ala Val
                180                 185                 190

Ser Val Lys Gly Arg Phe Thr Ile Ser Ala Asp Thr Ser Lys Asn Thr
                195                 200                 205

Ala Tyr Leu Gln Met Asn Ser Leu Arg Ala Glu Asp Thr Ala Val Tyr
                210                 215                 220

Tyr Cys Ala Arg Glu Trp Tyr Glu Ala Ser Tyr Tyr Asp Trp Phe Asp
225                 230                 235                 240

Tyr Phe Asp Phe Ser Asp Tyr Trp Gly Gln Gly Thr Leu Val Thr Val
                245                 250                 255

Ser Ser Ala Ala Ala His Lys Thr His Thr Cys Pro Pro Cys Pro Ala
                260                 265                 270

Pro Glu Leu Leu Gly Gly Pro Ser Val Phe Leu Phe Pro Pro Lys Pro
                275                 280                 285

Lys Asp Thr Leu Met Ile Ser Arg Thr Pro Glu Val Thr Cys Val Val
            290                 295                 300

Val Asp Val Ser His Glu Asp Pro Glu Val Lys Phe Asn Trp Tyr Val
305                 310                 315                 320

Asp Gly Val Glu Val His Asn Ala Lys Thr Lys Pro Arg Glu Glu Gln
                325                 330                 335

Tyr Asn Ser Thr Tyr Arg Val Val Ser Val Leu Thr Val Leu His Gln
                340                 345                 350

Asp Trp Leu Asn Gly Lys Glu Tyr Lys Cys Lys Val Ser Asn Lys Ala
                355                 360                 365

Leu Pro Ala Pro Ile Glu Lys Thr Ile Ser Lys Ala Lys Gly Gln Pro
                370                 375                 380

Arg Glu Pro Gln Val Tyr Thr Leu Pro Pro Ser Arg Asp Glu Leu Thr
385                 390                 395                 400

Lys Asn Gln Val Ser Leu Thr Cys Leu Val Lys Gly Phe Tyr Pro Ser
                405                 410                 415

Asp Ile Ala Val Glu Trp Glu Ser Asn Gly Gln Pro Glu Asn Asn Tyr
                420                 425                 430

Lys Thr Thr Pro Pro Val Leu Asp Ser Asp Gly Ser Phe Phe Leu Tyr
                435                 440                 445

Ser Lys Leu Thr Val Asp Lys Ser Arg Trp Gln Gln Gly Asn Val Phe
                450                 455                 460

Ser Cys Ser Val Met His Glu Ala Leu His Asn His Tyr Thr Gln Lys
465                 470                 475                 480

Ser Leu Ser Leu Ser Pro Gly Lys Gly Ser His His His His His His
                485                 490                 495

Lys Leu Asp Tyr Lys Asp His Asp Gly Asp Tyr Lys Asp His Asp Ile
                500                 505                 510

Asp Tyr Lys Asp Asp Asp Lys
                515                 520
```

<210> SEQ ID NO 111
<211> LENGTH: 107
<212> TYPE: PRT
<213> ORGANISM: ARTIFICIAL
<220> FEATURE:
<223> OTHER INFORMATION: Synthetic

<400> SEQUENCE: 111

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ala Ala Ala
            20                  25                  30

Val Ala Trp Tyr Gln Gln Lys Pro Asp Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Asn Thr Tyr Pro Pro
                85                  90                  95

Thr Phe Gly Gln Gly Thr Lys Val Glu Ile Lys
            100                 105

<210> SEQ ID NO 112
<211> LENGTH: 128
<212> TYPE: PRT
<213> ORGANISM: ARTIFICIAL
<220> FEATURE:
<223> OTHER INFORMATION: Synthetic

<400> SEQUENCE: 112

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Ser Pro Ser Ser Gly Ser Thr Arg Tyr Ala Gly Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Trp Tyr Glu Ala Ser Tyr Tyr Asp Trp Phe Asp Tyr Phe
            100                 105                 110

Asp Phe Ser Asp Tyr Trp Gly Gln Gly Thr Leu Val Thr Val Ser Ser
        115                 120                 125

<210> SEQ ID NO 113
<211> LENGTH: 107
<212> TYPE: PRT
<213> ORGANISM: ARTIFICIAL
<220> FEATURE:
<223> OTHER INFORMATION: Synthetic

<400> SEQUENCE: 113

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Asp Tyr Ala
            20                  25                  30

Val Ser Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Asn Thr Thr Pro Pro
                85                  90                  95

Thr Phe Gly Gln Gly Thr Lys Val Glu Ile Lys
            100                 105

<210> SEQ ID NO 114
<211> LENGTH: 128
<212> TYPE: PRT
<213> ORGANISM: ARTIFICIAL
<220> FEATURE:
<223> OTHER INFORMATION: Synthetic

<400> SEQUENCE: 114

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Ala Pro Asp Asn Gly Thr Thr Arg Tyr Ala Val Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Trp Tyr Glu Ala Ser Tyr Tyr Asp Trp Phe Asp Tyr Phe
            100                 105                 110

Asp Phe Ser Asp Tyr Trp Gly Gln Gly Thr Leu Val Thr Val Ser Ser
        115                 120                 125

<210> SEQ ID NO 115
<211> LENGTH: 19
<212> TYPE: PRT
<213> ORGANISM: ARTIFICIAL
<220> FEATURE:
<223> OTHER INFORMATION: Synthetic

<400> SEQUENCE: 115

Glu Trp Tyr Glu Ala Ser Tyr Tyr Asp Trp Phe Asp Tyr Phe Asp Phe
1               5                   10                  15

Ser Asp Tyr

<210> SEQ ID NO 116
<211> LENGTH: 17
<212> TYPE: PRT
<213> ORGANISM: ARTIFICIAL
<220> FEATURE:
<223> OTHER INFORMATION: Synthetic

<400> SEQUENCE: 116

Arg Ile Ser Pro Ser Ser Gly Ser Thr Arg Tyr Ala Gly Ser Val Lys
1               5                   10                  15

Gly

<210> SEQ ID NO 117
<211> LENGTH: 5
<212> TYPE: PRT
<213> ORGANISM: ARTIFICIAL
<220> FEATURE:
<223> OTHER INFORMATION: Synthetic

<400> SEQUENCE: 117

Asp Thr Tyr Ile His
1               5

<210> SEQ ID NO 118
<211> LENGTH: 9
<212> TYPE: PRT
<213> ORGANISM: ARTIFICIAL
<220> FEATURE:
<223> OTHER INFORMATION: Synthetic

<400> SEQUENCE: 118

Gln Gln His Asn Thr Tyr Pro Pro Thr
1               5

<210> SEQ ID NO 119
<211> LENGTH: 7
<212> TYPE: PRT
<213> ORGANISM: ARTIFICIAL
<220> FEATURE:
<223> OTHER INFORMATION: Synthetic

<400> SEQUENCE: 119

Ser Ala Ser Phe Leu Tyr Ser
1               5

<210> SEQ ID NO 120
<211> LENGTH: 11
<212> TYPE: PRT
<213> ORGANISM: ARTIFICIAL
<220> FEATURE:
<223> OTHER INFORMATION: Synthetic

<400> SEQUENCE: 120

Arg Ala Ser Gln Ser Val Ala Ala Ala Val Ala
1               5                   10

<210> SEQ ID NO 121
<211> LENGTH: 19
<212> TYPE: PRT
<213> ORGANISM: ARTIFICIAL
<220> FEATURE:
<223> OTHER INFORMATION: Synthetic

<400> SEQUENCE: 121

Glu Trp Tyr Glu Ala Ser Tyr Tyr Asp Trp Phe Asp Tyr Phe Asp Phe
1               5                   10                  15

Ser Asp Tyr

<210> SEQ ID NO 122
<211> LENGTH: 17
<212> TYPE: PRT
<213> ORGANISM: ARTIFICIAL
<220> FEATURE:
<223> OTHER INFORMATION: Synthetic

<400> SEQUENCE: 122

```
Arg Ile Ala Pro Asp Asn Gly Thr Thr Arg Tyr Ala Val Ser Val Lys
1               5                   10                  15

Gly

<210> SEQ ID NO 123
<211> LENGTH: 5
<212> TYPE: PRT
<213> ORGANISM: ARTIFICIAL
<220> FEATURE:
<223> OTHER INFORMATION: Synthetic

<400> SEQUENCE: 123

Asp Thr Tyr Ile His
1               5

<210> SEQ ID NO 124
<211> LENGTH: 9
<212> TYPE: PRT
<213> ORGANISM: ARTIFICIAL
<220> FEATURE:
<223> OTHER INFORMATION: Synthetic

<400> SEQUENCE: 124

Gln Gln His Asn Thr Thr Pro Pro Thr
1               5

<210> SEQ ID NO 125
<211> LENGTH: 7
<212> TYPE: PRT
<213> ORGANISM: ARTIFICIAL
<220> FEATURE:
<223> OTHER INFORMATION: Synthetic

<400> SEQUENCE: 125

Ser Ala Ser Phe Leu Tyr Ser
1               5

<210> SEQ ID NO 126
<211> LENGTH: 11
<212> TYPE: PRT
<213> ORGANISM: ARTIFICIAL
<220> FEATURE:
<223> OTHER INFORMATION: Synthetic

<400> SEQUENCE: 126

Arg Ala Ser Gln Ser Val Asp Tyr Ala Val Ser
1               5                   10
```

ANTIBODIES AND USE THEREOF

CROSS-REFERENCE TO RELATED APPLICATIONS

This application claims priority under 35 U.S.C. § 119 to U.S. Provisional Patent Application 62/827,444, filed Apr. 1, 2019; the contents of which are incorporated herein by reference.

The present invention relates to antibodies specific to fibrils of liraglutide or to fibrils of semaglutide as well as use of such antibodies.

SEQUENCE LISTING

The instant application contains a Sequence Listing which has been submitted in ASCII format via EFS-Web and is hereby incorporated by reference in its entirety. Said ASCII copy, created on Mar. 31, 2020, is named 190042US02_SeqList.txt and is 109 kilobytes in size.

BACKGROUND

Human GLP-1(7-37) and analogues thereof are known to be prone to form various types of aggregates in solution. A particular type of such aggregates, referred to as fibrils herein, are believed to be irreversibly formed and should be kept at a minimum in drug products for administration to patients in liquid form. Until now, preferred methods for assaying (i.e. identifying and/or quantifying) such fibrils are based on Thioflavin T (ThT) which is a fluorophore changing emission spectrum upon binding to fibrils, see e.g. Assay (V) herein. Assays detecting peptide fibrils via ThT often involves first stressing the samples to amplify the amount of fibrils to allow detection, such application of stress is undesired and time-consuming. Means to identify such peptide fibrils with higher sensitivity, also in mixtures comprising the soluble form of the peptide, are desired.

SUMMARY

In some embodiments the invention relates to an antibody binding liraglutide fibrils, wherein said fibrils are prepared according to Assay (I) herein. In some embodiments the invention relates to an antibody binding semaglutide fibrils, wherein said fibrils are prepared according to Assay (II) herein. In some embodiments the invention relates to an antibody binding liraglutide fibrils, wherein said fibrils are optionally prepared according to Assay (I) herein and said antibody has a level of binding to liraglutide fibrils which is at least 10 times higher than the level of binding of said antibody to soluble liraglutide, wherein said level of binding is determined according to Assay (III) at a liraglutide fibril concentration of at least 25 µM. In some embodiments the invention relates to an antibody binding liraglutide fibrils, wherein said fibrils are optionally prepared according to Assay (I) herein and said antibody has a detection limit for liraglutide fibrils at a concentration at least 10 times lower than the detection limit for liraglutide fibrils in a ThT assay, wherein said detection limit is determined according to Assay (VI) herein at a liraglutide fibril concentration of at least 1 µM. In some embodiments the invention relates to an antibody binding liraglutide fibrils, wherein said fibrils are optionally prepared according to Assay (I) herein and said antibody has a level of binding to liraglutide fibrils which is at least 5 times higher than the level of binding of said antibody to soluble liraglutide, wherein said antibody has a purity of above 95% monomer and wherein said level of binding is determined according to Assay (III-B) herein at a liraglutide fibril concentration of at least 30 µM. In some embodiments the invention relates to an antibody binding liraglutide fibrils, wherein said fibrils are optionally prepared according to Assay (I) herein and said antibody has a detection limit for liraglutide fibrils at a concentration at least 10 times lower than the detection limit for liraglutide fibrils in a ThT assay, wherein said antibody has a purity of above 95% monomer and wherein said detection limit is determined according to Assay (VI-B) herein at a liraglutide fibril concentration of at least 0.025 µM.

In some embodiments the invention relates to an antibody binding liraglutide fibrils, wherein the variable region of the heavy chain of said antibody comprises a CDR3 sequence and said CDR3 sequence is selected from the group consisting of SEQ ID NO: 37, 43, 49, 55, 61, 67, 73, 79, 85, 91, 97, 103, or any of said sequences with 1, 2 or 3 amino acid substitutions, deletions or insertions. In some embodiments the invention relates to an antibody binding liraglutide fibrils, wherein the variable region of the heavy chain of said antibody comprises a CDR3 sequence and said CDR3 sequence is selected from the group consisting of SEQ ID NO: 115 and 121, or any of said sequences with 1, 2 or 3 amino acid substitutions, deletions or insertions. In some embodiments the invention relates to an antibody binding liraglutide fibrils, wherein the variable region of the heavy chain of said antibody comprises a CDR1, a CDR2, and/or a CDR3 sequence selected from the group consisting of: SEQ ID NO: 37, 38 and 39; SEQ ID NO: 43, 44 and 45; SEQ ID NO: 49, 50 and 51; SEQ ID NO: 55, 56 and 57; SEQ ID NO: 61, 62 and 63; SEQ ID NO: 67, 68 and 69; SEQ ID NO: 73, 74 and 75; SEQ ID NO: 79, 80 and 81; SEQ ID NO: 85, 86 and 87; SEQ ID NO: 91, 92 and 93; SEQ ID NO: 97, 98 and 99; SEQ ID NO: 103, 104 and 105; or any of said sequences with 1, 2 or 3 amino acid substitutions, deletions or insertions. In some embodiments the invention relates to an antibody binding liraglutide fibrils, wherein the variable region of the heavy chain of said antibody comprises a CDR1, a CDR2, and/or a CDR3 sequence selected from the group consisting of: SEQ ID NO: 115, 116 and 117; SEQ ID NO: 121, 122, 123; or any of said sequences with 1, 2 or 3 amino acid substitutions, deletions or insertions. In some embodiments the invention relates to an antibody binding liraglutide fibrils, wherein the variable region of the light chain of said antibody comprises a CDR1, a CDR2, and/or a CDR3 sequence selected from the group consisting of: SEQ ID NO: 40, 41 and 42; SEQ ID NO: 46, 47 and 48; SEQ ID NO: 52, 53 and 54; SEQ ID NO: 58, 59 and 60; SEQ ID NO: 64, 65 and 66; SEQ ID NO: 70, 71 and 72; SEQ ID NO: 76, 77 and 78; SEQ ID NO: 82, 83 and 84; SEQ ID NO: 88, 89 and 90; SEQ ID NO: 94, 95 and 96; SEQ ID NO: 100, 101 and 102; SEQ ID NO: 106, 107 and 108; or any of said sequences with 1, 2 or 3 amino acid substitutions, deletions or insertions. In some embodiments the invention relates to an antibody binding liraglutide fibrils, wherein the variable region of the light chain of said antibody comprises a CDR1, a CDR2, and/or a CDR3 sequence selected from the group consisting of: SEQ ID NO: 118, 119 and 120; SEQ ID NO: 124, 125 and 126; or any of said sequences with 1, 2 or 3 amino acid substitutions, deletions or insertions.

In some embodiments the invention relates to an antibody binding liraglutide fibrils, wherein said antibody comprises a variable region of the heavy chain as defined in any one of the preceding embodiments and a variable region of the light chain as defined herein. In some embodiments the invention relates to an antibody binding liraglutide fibrils, wherein said antibody comprises a sequence selected from the group consisting of SEQ ID NO: 1, 2, 3, 4, 5, 6, 7, 8, 9, 10, 11 and 12; or any of said sequences with up to 20, such as up to 15 or up to 10, amino acid substitutions, deletions or insertions. In some embodiments the invention relates to an antibody binding liraglutide fibrils, wherein said antibody comprises a sequence selected from the group consisting of SEQ ID NO: 109 and 110; or any of said sequences with up to 20, such as up to 15 or up to 10, amino acid substitutions, deletions or insertions. In some embodiments the invention relates to an antibody binding liraglutide fibrils, wherein said antibody has at least 80%, such as at least 90% or at least 95%, sequence identity to a sequence selected from the group consisting of SEQ ID NO: 1, 2, 3, 4, 5, 6, 7, 8, 9, 10, 11 and 12. In some embodiments the invention relates to an antibody binding liraglutide fibrils, wherein said antibody has at least 80%, such as at least 90% or at least 95%, sequence identity to a sequence selected from the group consisting of SEQ ID NO: 109 and 110.

In some embodiments the invention relates to an antibody binding liraglutide fibrils, wherein said antibody comprises a variable light chain (VL) sequence selected from the group consisting of SEQ ID NO: 13, 15, 17, 19, 21, 23, 25, 27, 29, 31, 33, 35, 111 and 113; or any of said sequences with up to 20, such as up to 15 or up to 10, amino acid substitutions, deletions or insertions. In some embodiments the invention relates to an antibody binding liraglutide fibrils, wherein said antibody comprises a variable heavy chain (VH) sequence selected from the group consisting of SEQ ID NO: 14, 16, 18, 20, 22, 24, 26, 28, 30, 32, 34, 36, 112 and 114; or any of said sequences with up to 20, such as up to 15 or up to 10, amino acid substitutions, deletions or insertions.

In some embodiments the invention relates to use of an antibody as defined herein for identification of liraglutide fibrils or semaglutide fibrils. In some embodiments the invention relates to methods for identifying liraglutide fibrils or semaglutide fibrils, said method comprising the step of a) binding the antibody as defined herein to liraglutide fibrils or semaglutide fibrils. In some embodiments the invention relates to methods for quantifying liraglutide fibrils or semaglutide fibrils, said method comprising the step of a) binding the antibody as defined herein to liraglutide fibrils or semaglutide fibrils.

In some embodiments the invention relates to use of an antibody as defined herein for purification of liraglutide or semaglutide by removal or reduction of fibrils thereof by immobilisation of the antibody to a solid surface, e.g. a chromatographic or membrane surface creating an affinity surface, and exposing a mixture comprising both fibrils and soluble form of liraglutide or semaglutide the surface resulting in isolation of the fibrils or part thereof.

BRIEF DESCRIPTION OF DRAWINGS

FIG. 1 shows analytical size-exclusion chromatography of selected antibody variants, E, M and N.

DESCRIPTION

The present invention relates to antibodies which specifically bind to fibrils of the GLP-1 receptor agonist liraglutide or semaglutide. Liraglutide and semaglutide are analogues of human GLP-1(7-37) and are therapeutic peptides commercially available in the form of solutions. Fibrils of liraglutide or semaglutide are undesired in drug products. Thus, the antibodies of the invention will allow distinguishing fibrils of liraglutide or semaglutide from their soluble form. Such antibodies of the invention have several technical benefits, including allowing identification and/or quantification of such fibrils, optionally in a mixture with their soluble form, and providing means for ensuring sufficient quality of a drug product comprising liraglutide or semaglutide. In some embodiments the antibodies of the present invention allow isolation, or partly isolation, of liraglutide fibrils from a mixture of soluble liraglutide. Such isolation may be performed by immobilisation to a solid surface, e.g. a chromatographic column, filter, or membrane. In some embodiments the antibodies of the present invention allow sensitive assays for detecting extremely low levels of peptide fibrils, optionally in the presence of a great excess of the soluble form of the peptide. In some embodiments the term "fibrils", "peptide fibrils", also in relation to the specific peptides liraglutide or semaglutide, refer to a type of aggregate which may be obtained according to Assay (I) herein for liraglutide or according to Assay (II) herein for semaglutide, such fibrils are visible as in the shape of thin threads using e.g. transmission electron microscopy.

The present inventors surprisingly found that the antibodies of the invention are at least 100-fold, and perhaps even at least-1000 fold, more sensitive for detecting fibrils compared to a ThT Assay, such as a ThT assay without shaking, e.g. Assay (V) herein.

In some embodiments the invention relates to an antibody binding liraglutide fibrils. In some embodiments the invention relates to an antibody binding liraglutide fibrils, wherein said fibrils are prepared according to Assay (I) herein. In some embodiments the invention relates to an antibody binding semaglutide fibrils. In some embodiments the invention relates to an antibody binding semaglutide fibrils, wherein said fibrils are prepared according to Assay (II) herein. In some embodiments the antibody has a detection limit for liraglutide fibrils at a concentration at least 10 times, such as at least 100 times or at least 1000 times, lower than the detection limit for liraglutide fibrils in a ThT assay, said detection limit optionally determined according to Assay (VI) herein. In some embodiments the antibody has a level of binding to liraglutide fibrils which is at least 10 times higher, such as at least 20 times higher or at least 50 times higher, than the level of binding of said antibody to soluble liraglutide. In some embodiments the antibody has a detection limit for semaglutide fibrils at a concentration at least 10 times, such as at least 100 times or at least 1000 times, lower than the detection limit for semaglutide fibrils in a ThT assay, said detection limit optionally determined according to Assay (VI) herein. In some embodiments the antibody has a level of binding to semaglutide fibrils which is at least 10 times higher, such as at least 20 times higher or at least 50 times higher than the level of binding of said antibody to soluble semaglutide. In some embodiments the level of binding is determined according to Assay (IV) herein. In some embodiments the level of binding is determined according to Assay (III) herein. In some embodiments the level of binding is determined according to Assay (III-B) herein.

In some embodiments the invention relates to an antibody binding liraglutide fibrils, wherein said fibrils are optionally prepared according to Assay (I) herein and said antibody has a level of binding to liraglutide fibrils which is at least 10 times higher than the level of binding of said antibody to soluble liraglutide, wherein said level of binding is determined according to Assay (III) at a liraglutide fibril concentration of at least 25 µM. In some embodiments the invention relates to an antibody binding liraglutide fibrils, wherein said fibrils are optionally prepared according to Assay (I)

herein and said antibody has a detection limit for liraglutide fibrils at a concentration at least 10 times lower than the detection limit for liraglutide fibrils in a ThT assay, wherein said detection limit is determined according to Assay (VI) herein at a liraglutide fibril concentration of at least 1 μM. In some embodiments the invention relates to an antibody binding liraglutide fibrils, wherein said fibrils are optionally prepared according to Assay (I) herein and said antibody has a level of binding to liraglutide fibrils which is at least 5 times higher than the level of binding of said antibody to soluble liraglutide, wherein said antibody has a purity of above 95% monomer and wherein said level of binding is determined according to Assay (III-B) herein at a liraglutide fibril concentration of at least 30 μM. In some embodiments the invention relates to an antibody binding liraglutide fibrils, wherein said fibrils are optionally prepared according to Assay (I) herein and said antibody has a detection limit for liraglutide fibrils at a concentration at least 10 times lower than the detection limit for liraglutide fibrils in a ThT assay, wherein said antibody has a purity of above 95% monomer and wherein said detection limit is determined according to Assay (VI-B) herein at a liraglutide fibril concentration of at least 0.025 μM.

In some embodiments the invention relates to an antibody binding liraglutide fibrils, wherein said antibody can detect liraglutide fibrils at concentrations of 1-1000 ppm fibrils in solution, such as 1-10 ppm fibrils, alternatively 10-100 ppm fibrils, alternatively 100-1000 ppm fibrils.

In some embodiments the invention relates to an antibody binding liraglutide fibrils, wherein the variable region of the heavy chain of said antibody comprises a CDR3 sequence and said CDR3 sequence is selected from the group consisting of SEQ ID NO: 37, 43, 49, 55, 61, 67, 73, 79, 85, 91, 97, 103, or any of said sequences with 1, 2 or 3 amino acid substitutions, deletions or insertions. In some embodiments the invention relates to an antibody binding liraglutide fibrils, wherein the variable region of the heavy chain of said antibody comprises a CDR3 sequence and said CDR3 sequence is selected from the group consisting of SEQ ID NO: 115 and 121, or any of said sequences with 1, 2 or 3 amino acid substitutions, deletions or insertions. In some embodiments the invention relates to an antibody binding liraglutide fibrils, wherein the variable region of the heavy chain of said antibody comprises a CDR3 sequence and said CDR3 sequence is selected from the group consisting of SEQ ID NO: 37, 43, 49, 55, 61, 67, 73, 79, 85, 91, 97, 103, or any of said sequences with 1, 2 or 3 amino acid substitutions, deletions or insertions. In some embodiments the variable region of the heavy chain of said antibody comprises the CDR3 sequence of SEQ ID NO: 37, or any of said sequences with 1, 2 or 3 amino acid substitutions, deletions or insertions. In some embodiments the variable region of the heavy chain of said antibody comprises the CDR3 sequence of SEQ ID NO: 43, or any of said sequences with 1, 2 or 3 amino acid substitutions, deletions or insertions. In some embodiments the variable region of the heavy chain of said antibody comprises the CDR3 sequence of SEQ ID NO: 49, or any of said sequences with 1, 2 or 3 amino acid substitutions, deletions or insertions. In some embodiments the variable region of the heavy chain of said antibody comprises the CDR3 sequence of SEQ ID NO: 55, or any of said sequences with 1, 2 or 3 amino acid substitutions, deletions or insertions. In some embodiments the variable region of the heavy chain of said antibody comprises the CDR3 sequence of SEQ ID NO: 61, or any of said sequences with 1, 2 or 3 amino acid substitutions, deletions or insertions. In some embodiments the variable region of the heavy chain of said antibody comprises the CDR3 sequence of SEQ ID NO: 67, or any of said sequences with 1, 2 or 3 amino acid substitutions, deletions or insertions. In some embodiments the variable region of the heavy chain of said antibody comprises the CDR3 sequence of SEQ ID NO: 73, or any of said sequences with 1, 2 or 3 amino acid substitutions, deletions or insertions. In some embodiments the variable region of the heavy chain of said antibody comprises the CDR3 sequence of SEQ ID NO: 79, or any of said sequences with 1, 2 or 3 amino acid substitutions, deletions or insertions. In some embodiments the variable region of the heavy chain of said antibody comprises the CDR3 sequence of SEQ ID NO: 85, or any of said sequences with 1, 2 or 3 amino acid substitutions, deletions or insertions. In some embodiments the variable region of the heavy chain of said antibody comprises the CDR3 sequence of SEQ ID NO: 91, or any of said sequences with 1, 2 or 3 amino acid substitutions, deletions or insertions. In some embodiments the variable region of the heavy chain of said antibody comprises the CDR3 sequence of SEQ ID NO: 97, or any of said sequences with 1, 2 or 3 amino acid substitutions, deletions or insertions. In some embodiments the variable region of the heavy chain of said antibody comprises the CDR3 sequence of SEQ ID NO: 103, or any of said sequences with 1, 2 or 3 amino acid substitutions, deletions or insertions. In some embodiments the variable region of the heavy chain of said antibody comprises the CDR3 sequence of SEQ ID NO: 115, or any of said sequences with 1, 2 or 3 amino acid substitutions, deletions or insertions. In some embodiments the variable region of the heavy chain of said antibody comprises the CDR3 sequence of SEQ ID NO: 121, or any of said sequences with 1, 2 or 3 amino acid substitutions, deletions or insertions.

In some embodiments the invention relates to an antibody binding liraglutide fibrils, wherein the variable region of the heavy chain of said antibody comprises a CDR1, a CDR2, and/or a CDR3 sequence selected from the group consisting of: SEQ ID NO: 37, 38 and 39; SEQ ID NO: 43, 44 and 45; SEQ ID NO: 49, 50 and 51; SEQ ID NO: 55, 56 and 57; SEQ ID NO: 61, 62 and 63; SEQ ID NO: 67, 68 and 69; SEQ ID NO: 73, 74 and 75; SEQ ID NO: 79, 80 and 81; SEQ ID NO: 85, 86 and 87; SEQ ID NO: 91, 92 and 93; SEQ ID NO: 97, 98 and 99; SEQ ID NO: 103, 104 and 105; or any of said sequences with 1, 2 or 3 amino acid substitutions, deletions or insertions. In some embodiments the invention relates to an antibody binding liraglutide fibrils, wherein the variable region of the heavy chain of said antibody comprises a CDR1, a CDR2, and/or a CDR3 sequence selected from the group consisting of: SEQ ID NO: 115, 116 and 117; SEQ ID NO: 121, 122, 123; or any of said sequences with 1, 2 or 3 amino acid substitutions, deletions or insertions. In some embodiments the invention relates to an antibody binding liraglutide fibrils, wherein the variable region of the heavy chain of said antibody comprises a CDR1, a CDR2, and/or a CDR3 sequence selected from the group consisting of: SEQ ID NO: 37, 38 and 39; SEQ ID NO: 43, 44 and 45; SEQ ID NO: 49, 50 and 51; SEQ ID NO: 55, 56 and 57; SEQ ID NO: 61, 62 and 63; SEQ ID NO: 67, 68 and 69; SEQ ID NO: 73, 74 and 75; SEQ ID NO: 79, 80 and 81; SEQ ID NO: 85, 86 and 87; SEQ ID NO: 91, 92 and 93; SEQ ID NO: 97, 98 and 99; SEQ ID NO: 103, 104 and 105; or any of said sequences with 1, 2 or 3 amino acid substitutions, deletions or insertions. In some embodiments the invention relates to an antibody binding liraglutide fibrils, wherein the variable region of the heavy chain of said antibody comprises a CDR1, a CDR2, and/or a CDR3 sequence selected from the group consisting of: SEQ ID NO: SEQ ID NO: 115, 116 and 117; SEQ ID NO: 121, 122, 123; or any of said sequences with 1, 2 or 3 amino acid substitutions, deletions or insertions. In some embodiments the variable region of the heavy chain of said antibody comprises a CDR1, a CDR2, and/or a CDR3 sequence selected from the group consisting of: SEQ ID NO: 37, 38 and 39; or any of said sequences with 1, 2 or 3 amino acid substitutions, deletions or insertions. In some embodiments the variable region of the heavy chain of said antibody comprises a CDR1, a CDR2, and/or a CDR3 sequence selected from the group consisting of: SEQ ID NO: 43, 44 and 45; or any of said sequences with 1, 2 or 3 amino acid substitutions, deletions or insertions. In some embodiments the variable region of the heavy chain of said antibody comprises a CDR1, a CDR2, and/or a CDR3 sequence selected from the group consisting of: SEQ ID NO: 49, 50 and 51; or any of said sequences with 1, 2 or 3 amino acid substitutions, deletions or insertions. In some embodiments the variable region of the heavy chain of said antibody comprises a CDR1, a CDR2, and/or a CDR3 sequence selected from the group consisting of: SEQ ID NO: 55, 56 and 57; or any of said sequences with 1, 2 or 3 amino acid substitutions, deletions or insertions. In some embodiments the variable region of the heavy chain of said antibody comprises a CDR1, a CDR2, and/or a CDR3 sequence selected from the group consisting of: SEQ ID NO: 61, 62 and 63; or any of said sequences with 1, 2 or 3 amino acid substitutions, deletions or insertions. In some embodiments the variable region of the heavy chain of said antibody comprises a CDR1, a CDR2, and/or a CDR3 sequence selected from the group consisting of: SEQ ID NO: 67, 68 and 69; or any of said sequences with 1, 2 or 3 amino acid substitutions, deletions or insertions. In some embodiments the variable region of the heavy chain of said antibody comprises a CDR1, a CDR2, and/or a CDR3 sequence selected from the group consisting of: SEQ ID NO: 73, 74 and 75; or any of said sequences with 1, 2 or 3 amino acid substitutions, deletions or insertions. In some embodiments the variable region of the heavy chain of said antibody comprises a CDR1, a CDR2, and/or a CDR3 sequence selected from the group consisting of: SEQ ID NO: 79, 80 and 81; or any of said sequences with 1, 2 or 3 amino acid substitutions, deletions or insertions. In some embodiments the variable region of the heavy chain of said antibody comprises a CDR1, a CDR2, and/or a CDR3 sequence selected from the group consisting of: SEQ ID NO: 85, 86 and 87; or any of said sequences with 1, 2 or 3 amino acid substitutions, deletions or insertions. In some embodiments the variable region of the heavy chain of said antibody comprises a CDR1, a CDR2, and/or a CDR3 sequence selected from the group consisting of: SEQ ID NO: 91, 92 and 93; or any of said sequences with 1, 2 or 3 amino acid substitutions, deletions or insertions. In some embodiments the variable region of the heavy chain of said antibody comprises a CDR1, a CDR2, and/or a CDR3 sequence selected from the group consisting of: SEQ ID NO: 97, 98 and 99; or any of said sequences with 1, 2 or 3 amino acid substitutions, deletions or insertions. In some embodiments the variable region of the heavy chain of said antibody comprises a CDR1, a CDR2, and/or a CDR3 sequence selected from the group consisting of: SEQ ID NO: 103, 104 and 105; or any of said sequences with 1, 2 or 3 amino acid substitutions, deletions or insertions. In some embodiments the variable region of the heavy chain of said antibody comprises a CDR1, a CDR2, and/or a CDR3 sequence selected from the group consisting of: SEQ ID NO: 115, 116 and 117; or any of said sequences with 1, 2 or 3 amino acid substitutions, deletions or insertions. In some embodiments the variable region of the heavy chain of said antibody comprises a CDR1, a CDR2, and/or a CDR3 sequence selected from the group consisting of: SEQ ID NO: 121, 122, 123; or any of said sequences with 1, 2 or 3 amino acid substitutions, deletions or insertions.

In some embodiments the invention relates to an antibody binding liraglutide fibrils, wherein the variable region of the light chain of said antibody comprises a CDR1, a CDR2, and/or a CDR3 sequence selected from the group consisting of: SEQ ID NO: 40, 41 and 42; SEQ ID NO: 46, 47 and 48; SEQ ID NO: 52, 53 and 54; SEQ ID NO: 58, 59 and 60; SEQ ID NO: 64, 65 and 66; SEQ ID NO: 70, 71 and 72; SEQ ID NO: 76, 77 and 78; SEQ ID NO: 82, 83 and 84; SEQ ID NO: 88, 89 and 90; SEQ ID NO: 94, 95 and 96; SEQ ID NO: 100, 101 and 102; SEQ ID NO: 106, 107 and 108; or any of said sequences with 1, 2 or 3 amino acid substitutions, deletions or insertions. In some embodiments the invention relates to an antibody binding liraglutide fibrils, wherein the variable region of the light chain of said antibody comprises a CDR1, a CDR2, and/or a CDR3 sequence selected from the group consisting of: SEQ ID NO: 118, 119 and 120; SEQ ID NO: 124, 125 and 126; or any of said sequences with 1, 2 or 3 amino acid substitutions, deletions or insertions. In some embodiments the invention relates to an antibody binding liraglutide fibrils, wherein the variable region of the light chain of said antibody comprises a CDR1, a CDR2, and/or a CDR3 sequence selected from the group consisting of: SEQ ID NO: 40, 41 and 42; or any of said sequences with 1, 2 or 3 amino acid substitutions, deletions or insertions. In some embodiments the invention relates to an antibody binding liraglutide fibrils, wherein the variable region of the light chain of said antibody comprises a CDR1, a CDR2, and/or a CDR3 sequence selected from the group consisting of: SEQ ID NO: 46, 47 and 48; or any of said sequences with 1, 2 or 3 amino acid substitutions, deletions or insertions. In some embodiments the invention relates to an antibody binding liraglutide fibrils, wherein the variable region of the light chain of said antibody comprises a CDR1, a CDR2, and/or a CDR3 sequence selected from the group consisting of: SEQ ID NO: 52, 53 and 54; or any of said sequences with 1, 2 or 3 amino acid substitutions, deletions or insertions. In some embodiments the invention relates to an antibody binding liraglutide fibrils, wherein the variable region of the light chain of said antibody comprises a CDR1, a CDR2, and/or a CDR3 sequence selected from the group consisting of: SEQ ID NO: 58, 59 and 60; or any of said sequences with 1, 2 or 3 amino acid substitutions, deletions or insertions. In some embodiments the invention relates to an antibody binding liraglutide fibrils, wherein the variable region of the light chain of said antibody comprises a CDR1, a CDR2, and/or a CDR3 sequence selected from the group consisting of: SEQ ID NO: 64, 65 and 66; or any of said sequences with 1, 2 or 3 amino acid substitutions, deletions or insertions. In some embodiments the invention relates to an antibody binding liraglutide fibrils, wherein the variable region of the light chain of said antibody comprises a CDR1, a CDR2, and/or a CDR3 sequence selected from the group consisting of: SEQ ID NO: 70, 71 and 72; or any of said sequences with 1, 2 or 3 amino acid substitutions, deletions or insertions. In some embodiments the invention relates to an antibody binding liraglutide fibrils, wherein the variable region of the light chain of said antibody comprises a CDR1, a CDR2, and/or a CDR3 sequence selected from the group consisting of: SEQ ID NO: 76, 77 and 78; or any of said sequences with 1, 2 or 3 amino acid substitutions, deletions or insertions. In some embodiments the invention relates to an antibody binding liraglutide fibrils, wherein the variable region of the light chain of said antibody comprises a CDR1, a CDR2, and/or a CDR3 sequence selected from the group consisting of: SEQ ID NO: 82, 83 and 84; or any of said sequences with 1, 2 or 3 amino acid substitutions, deletions or insertions. In some embodiments the invention relates to an antibody binding liraglutide fibrils, wherein the variable region of the light chain of said antibody comprises a CDR1, a CDR2, and/or a CDR3 sequence selected from the group consisting of: SEQ ID NO: 88, 89 and 90; or any of said sequences with 1, 2 or 3 amino acid substitutions, deletions or insertions. In some embodiments the invention relates to an antibody binding liraglutide fibrils, wherein the variable region of the light chain of said antibody comprises a CDR1, a CDR2, and/or a CDR3 sequence selected from the group consisting of: SEQ ID NO: 94, 95 and 96; or any of said sequences with 1, 2 or 3 amino acid substitutions, deletions or insertions. In some embodiments the invention relates to an antibody binding liraglutide fibrils, wherein the variable region of the light chain of said antibody comprises a CDR1, a CDR2, and/or a CDR3 sequence selected from the group consisting of: SEQ ID NO: 100, 101 and 102; or any of said sequences with 1, 2 or 3 amino acid substitutions, deletions or insertions. In some embodiments the invention relates to an antibody binding liraglutide fibrils, wherein the variable region of the light chain of said antibody comprises a CDR1, a CDR2, and/or a CDR3 sequence selected from the group consisting of: SEQ ID NO: 106, 107 and 108; or any of said sequences with 1, 2 or 3 amino acid substitutions, deletions or insertions. In some embodiments the invention relates to an antibody binding liraglutide fibrils, wherein the variable region of the light chain of said antibody comprises a CDR1, a CDR2, and/or a CDR3 sequence selected from the group consisting of: SEQ ID NO: 118, 119 and 120; or any of said sequences with 1, 2 or 3 amino acid substitutions, deletions or insertions. In some embodiments the invention relates to an antibody binding liraglutide fibrils, wherein the variable region of the light chain of said antibody comprises a CDR1, a CDR2, and/or a CDR3 sequence selected from the group consisting of: SEQ ID NO: 124, 125 and 126; or any of said sequences with 1, 2 or 3 amino acid substitutions, deletions or insertions. In some embodiments the invention relates to an antibody binding liraglutide fibrils, wherein said antibody comprises a variable region of the heavy chain as defined herein and a variable region of the light chain as defined in any one of the preceding embodiments. In some embodiments the invention relates to an antibody binding liraglutide fibrils, wherein said antibody comprises a sequence selected from the group consisting of SEQ ID NO: 1, 2, 3, 4, 5, 6, 7, 8, 9, 10, 11 and 12; or any of said sequences with up to 20, such as up to 15 or up to 10, amino acid substitutions, deletions or insertions. In some embodiments the invention relates to an antibody binding liraglutide fibrils, wherein said antibody comprises a sequence selected from the group consisting of SEQ ID NO: 109 and 110; or any of said sequences with up to 20, such as up to 15 or up to 10, amino acid substitutions, deletions or insertions. In some embodiments the invention relates to an antibody binding liraglutide fibrils, wherein said antibody has at least 80%, such as at least 90% or at least 95%, sequence identity to a sequence selected from the group consisting of SEQ ID NO: 1, 2, 3, 4, 5, 6, 7, 8, 9, 10, 11 and 12. In some embodiments the invention relates to an antibody binding liraglutide fibrils, wherein said antibody has at least 80%, such as at least 90% or at least 95%, sequence identity to a sequence selected from the group consisting of SEQ ID NO: 109 and 110. In some embodiments the antibody has at least 70%, such as at least 75%, sequence identity to a sequence defined herein. In some embodiments the antibody has at least 80%, such as at least 85% or at least 90%, sequence identity to a sequence defined herein. In some embodiments the antibody has at least 91%, such as at least 92% or at least 93%, sequence identity to a sequence defined herein. In some embodiments the antibody has at least 94%, such as at least 95% or at least 96%, sequence identity to a sequence defined herein. In some embodiments the antibody has at least 97%, such as at least 98% or at least 99%, sequence identity to a sequence defined herein.

In some embodiments the invention relates to an antibody binding liraglutide fibrils, wherein said antibody comprises a variable light chain (VL) sequence selected from the group consisting of SEQ ID NO: 13, 15, 17, 19, 21, 23, 25, 27, 29, 31, 33, 35, 111 and 113; or any of said sequences with up to 20, such as up to 15 or up to 10, amino acid substitutions, deletions or insertions. In some embodiments the invention relates to an antibody binding liraglutide fibrils, wherein said antibody comprises a variable heavy chain (VH) sequence selected from the group consisting of SEQ ID NO: 14, 16, 18, 20, 22, 24, 26, 28, 30, 32, 34, 36, 112 and 114; or any of said sequences with up to 20, such as up to 15 or up to 10, amino acid substitutions, deletions or insertions.

In some embodiments the antibody is an isolated antibody. In some embodiments the antibody is single chain Fv fragment. In some embodiments the antibody comprises an Fc domain. In some embodiments the antibody is single chain Fv fragment further comprising an Fc domain. In some embodiments the antibody specifically binds said liraglutide fibrils and/or semaglutide fibrils. In some embodiments the antibody specifically binds said liraglutide fibrils. In some embodiments the antibody specifically binds said semaglutide fibrils.

In some embodiments the antibody binding liraglutide fibrils has a purity of above 70%, alternatively above 75%, alternatively above 80%, alternatively above 85%, alternatively above 90%, alternatively above 95% monomer. In some embodiments the antibody binding liraglutide fibrils has a purity of above 70% monomer. In some embodiments the antibody binding liraglutide fibrils has a purity of above 75% monomer. In some embodiments the antibody binding liraglutide fibrils has a purity of above 80% monomer. In some embodiments the antibody binding liraglutide fibrils has a purity of above 85% monomer. In some embodiments the antibody binding liraglutide fibrils has a purity of above 90% monomer. In some embodiments the antibody binding liraglutide fibrils has a purity of above 95% monomer. In some embodiments purity of the antibody binding liraglutide fibrils is determined according method described herein under "Size-exclusion chromatography" followed by determination of area under the curve based on absorbance at 280 nm ($AUC_{280\ nm}$) for the peak of the monomeric antibody in relation to the sum of $AUC_{280\ nm}$ for all peaks.

Liraglutide and Semaglutide

Liraglutide and semaglutide are analogues of human GLP-1(7-37) comprising a covalently attached moiety. The antibodies of the invention bind liraglutide fibrils and/or semaglutide fibrils. The term "fibril" as used herein in relation to liraglutide refers to liraglutide fibrils and as used herein in relation to semaglutide refers to semaglutide fibrils. In some embodiments the antibodies of the invention bind liraglutide fibrils. In some embodiments the antibodies of the invention bind semaglutide fibrils.

Liraglutide is Arg34,Lys26-(N-epsilon-(gamma-L-glutamyl(N-alfa-hexadecanoyl)))-GLP-1(7-37), and may be prepared according to Example 37 of WO98/08871. Example 37 of WO98/08871 is incorporated herein by reference. The structure of liraglutide was also published in WHO Drug Information Vol. 17, No. 2, 2003. The structure of liraglutide was also published in WHO Drug Information Vol. 24, No. 1, 2010. Liraglutide fibrils may be prepared as described in Assay (I) herein. An example of soluble liraglutide is the commercially available solutions manufactured by Novo Nordisk A/S, Denmark; e.g. trademark Victoza®. Semaglutide is N-ε26-[2-(2-[2-(2-[2-(2-[4-(17-Carboxyheptadecanoylamino)-4(S)-carboxybutyrylamino]ethoxy)ethoxy]acetylamino)ethoxy]ethoxy)acetyl][Aib8,Arg34]GLP-1-(7-37)peptide, and may be prepared according to Example 4 of WO2006/097537. Example 4 of WO2006/097537 is incorporated herein by reference. Semaglutide fibrils may be prepared as described in Assay (II) herein. An example of soluble semaglutide is the commercially available solution manufactured by Novo Nordisk A/S, Denmark; trademark Ozempic®.

Antibodies

In some embodiments the invention relates to one or more of a series of antibodies which are characterized by their functionality and/or the amino acid sequence of the CDRs, the variable region of the heavy chain, the variable region of the light chain and/or the sequence of the Fc domain. In some embodiments the term "CDR" as used herein is determined are according to the Kabat antibody numbering scheme (Kabat, Elvin A. (1976). Structural Concepts in Immunology and Immunochemistry. New York, N.Y., USA: Holt, Rinehart & Winston). In some embodiments the invention relates to one or more of a series of antibodies which are characterized by their functionality and/or the H-CDR3 amino acid sequence. In some embodiments the invention relates to one or more of a series of antibodies which are characterized by their functionality and/or the CDR amino acid sequences (CDR1, CDR2, and CDR3 of the variable region of the heavy chain may be referred herein to as H-CDR1, H-CDR2, and H-CDR3. Similarly, CDR1, CDR2, and CDR3 of the variable region of the light chain may be referred to herein as L-CDR1, L-CDR2, and L-CDR3). In some embodiments the invention relates to one or more of a series of antibodies which are characterized by their functionality and/or the amino acid sequence of the variable region of the heavy chain and the variable region of the light chain. In some embodiments the invention relates to one or more of a series of antibodies which are characterized by their functionality and/or the amino acid sequence of the variable region of the heavy chain, the variable region of the light chain and/or the sequence of the Fc domain. In some embodiments the antibody comprises H-CDR3. In some embodiments the antibody comprises H-CDR1, H-CDR2, and/or H-CDR3. In some embodiments the antibody comprises H-CDR1, H-CDR2, and H-CDR3. In some embodiments the antibody comprises L-CDR1, L-CDR2, and/or L-CDR3. In some embodiments the antibody comprises L-CDR1, L-CDR2, and L-CDR3. In some embodiments the antibody comprises a variable region of the heavy chain and/or a variable region of the light chain.

An antibody of the invention may be in any format, including a whole antibody and an antigen binding fragment (i.e., "antigen-binding portion") or a single chain antibody. In some embodiments the antibody is a single chain variable fragment (scFv) antibody. In some embodiments the antibody is a single chain variable fragment fused to an Fc domain (scFv-Fc) antibody. In some embodiments, scFv or scFv-Fc antibodies consist of one amino acid sequence which comprises a variable region of the heavy chain ($V_H$) and a variable region of the light chain (VL); scFv-Fc antibodies further comprise an Fc domain.

In some embodiments the antibody is a full-length antibody comprising standard antibody domains and regions, e.g. as described herein. Full-length antibodies (or whole antibodies) comprise four polypeptide chains, two heavy (H) chains and two light (L) chains interconnected by disulfide bonds. Each heavy chain comprises a variable region of the heavy chain ($V_H$) and a heavy chain constant region ($C_H$). Each light chain comprises a variable region of the light chain (VL) and a light chain constant region (CL). The heavy chain constant region comprises three domains, $C_H1$, $C_H2$ and $C_H3$. Each light chain comprises a light chain variable region (abbreviated herein as VL) and a light chain constant region. The light chain constant region comprises one domain, CL.

The variable region of the heavy chain and the variable region of the light chain each comprise a binding domain that interacts with the antigen. The $V_H$ and $V_L$ regions can be further subdivided into regions of hypervariability, termed complementarity determining regions (CDR), interspersed with regions that are more conserved, termed framework regions (FR). Each $V_H$ and $V_L$ may comprise three CDRs and four FRs, arranged from amino-terminus to carboxy-terminus in the following order: FR1, CDR1, FR2, CDR2, FR3, CDR3, FR4. The constant regions of the antibodies may mediate the binding of the immunoglobulin to host tissues or factors, including various cells of the immune system (e.g., effector cells) and the first component (Clq) of the classical complement system.

In some embodiments the antibody is an antibody fragment, such fragments may be obtained using conventional recombinant or protein engineering techniques. Antibody fragments of the invention may be made by truncation, e.g. by removal of one or more amino acids from the N and/or C-terminal ends of a polypeptide. Fragments may also be generated by one or more internal deletions. In some embodiments, the antibody of the invention is, or comprises, a fragment of any one of the antibodies described herein. In some embodiments, the antibody of the invention is, or comprises, an antigen binding portion of one of the antibodies described herein, or variants thereof. For example, the antibody of the invention may be an Fab fragment of one of the antibodies described herein, or variants thereof, or the antibody of the invention may be a single chain antibody derived from one of the antibodies described herein, or a variant thereof. Examples of antigen-binding fragments include Fab, Fab', F(ab)2, F(ab')2, Fv (typically the $V_L$ and $V_H$ of a single arm of an antibody), single-chain Fv (scFv; see e.g. Bird et al., Science 1988; 242:42S-426; and Huston et al. PNAS 1988; 85:5879-5883), Fd (typically the $V_H$ and $C_H1$), and dAb (typically a $V_H$) fragments; $V_H$, $V_L$, VhH, and V-NAR; monovalent molecules comprising a single $V_H$ and a single $V_L$ chain; minibodies, diabodies, triabodies, tetrabodies, and kappa bodies (see, e.g., Ill et al., Protein Eng 1997; 10:949-57); camel IgG; IgNAR; as well as one or more isolated CDRs or a functional paratope, where the isolated CDRs or antigen-binding residues or polypeptides can be associated or linked together so as to form a functional antibody fragment. Various types of antibody fragments have been described or reviewed in, e.g., Holliger and Hudson, Nat Biotechnol 2005; 2S:1126-1136; WO2005040219, and published U.S. Patent Applications 20050238646 and 20020161201.

The terms "complementarity-determining region" ("CDR") or "hypervariable region", when used herein, refer to the amino acid residues of an antibody that are responsible for antigen binding. The CDRs are generally comprised of CDR1, CDR2, and CDR3 in the variable region of the light chain and CDR1, CDR2, and CDR3 in the variable region of the heavy chain defined according to Kabat and/or those residues from a "hypervariable loop" (Chothia and Lesk, J. Mol. Biol 1987; 196:901-917). Typically, the numbering of amino acid residues in this region is performed by the method described in Kabat et al., supra. The term "Kabat" as used herein refers to the numbering system for the variable region of the heavy chain and/or the variable region of the light chain described in e.g. Kabat et al. (1991) Sequences of Proteins of Immunological Interest, Fifth Edition, U.S. Department of Health and Human Services, NIH Publication No. 91-3242. Using the Kabat numbering system, the actual linear amino acid sequence of a peptide may contain fewer or additional amino acids corresponding to a shortening of, or insertion into, a framework (FR) or CDR of the variable region. The Kabat numbering of residues may be determined for a given antibody by alignment at regions of homology of the sequence of the antibody with a "standard" Kabat numbered sequence. The term "framework region" or "FR" residues refer to those $V_H$ or $V_L$ amino acid residues that are not within the CDRs, as defined herein. The fragment crystallizable region ("Fc domain") of an antibody is the region of an antibody that is capable of interacting with cell surface receptors called Fc receptors, as well as some proteins of the complement system.

The term "antibody derivatives" refers to any modified form of the antibody, such as a conjugate of the antibody and another agent or antibody.

The term "antigen" may refer to the molecular entity used for generating an antibody. However, herein the term "antigen" broadly refers to target molecules binding, or specifically binding, the antibody; thus, including fragments or mimics of the molecular entity used to generate the antibody. Antibodies may be generated in any way including by immunization of an animal or display screening, e.g. phage display or yeast display.

The term "epitope", as used herein, is defined in the context of a molecular interaction between an "antigen binding" polypeptide, such as an antibody or a fragment thereof, and its corresponding antigen. Generally, "epitope" refers to the area or region on an antigen to which an antibody binds, or specifically binds, i.e. the area or region in physical contact with the antibody. An epitope may comprise amino acid residues in the antigen that are directly involved in binding to the antibody (also called the immunodominant component of the epitope) and other amino acid residues, which are not directly involved in binding, such as amino acid residues of the antigen which are effectively blocked by the antibody (in other words, the amino acid residue is within the "solvent-excluded surface" and/or the "footprint" of the antibody). A given antigen may comprise a number of different epitopes, which may include, without limitation; linear peptide antigenic determinants, conformational antigenic determinants which consist of one or more non-contiguous amino acids located near each other in the native (mature) conformation; and post-translational antigenic determinants which consist, either in whole or part, of molecular structures covalently attached to the antigen, such as carbohydrate groups.

The terms "binding", "specifically binding" and "specificity" of an antibody are used herein to describe the selectivity of an antibody or an antigen binding fragment thereof. Antibodies according to the invention may specifically bind liraglutide fibrils or semaglutide fibrils, indicating that the antibody has a significantly lower level of binding to other antigens. In some embodiments significantly lower is at least 10-fold lower, such as at least 15-fold lower or at least 20-fold lower, level of binding. Level of binding may be determined according to Assay (III) herein or according to Assay (IV) herein. Level of binding may be determined according to Assay (III-B) herein.

The term "sequence identity" as used herein refers to the degree of relatedness between polypeptide sequences, as determined by the number of matches between strings of two or more amino acid residues and may be determined as the percent of identical matches between the smaller of two or more sequences with gap alignments (if any) addressed by a particular mathematical model or computer program (i.e., "algorithms"). Sequence identity of polypeptides can be readily calculated by methods known in the art, including, but not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988). Preferred methods for determining sequence identity are designed to give the largest match between the sequences tested. Methods of determining sequence identity are described in publicly available computer programs; such preferred computer program methods for determining sequence identity between two sequences include the GCG program package, including GAP (Devereux et al., Nucl. Acid. Res. 12, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well-known Smith Waterman algorithm may also be used to determine sequence identity. For example, using the computer algorithm GAP (Genetics Computer Group, University of Wisconsin, Madison, Wis.), two polypeptides for which the percent sequence identity is to be determined are aligned for optimal matching of their respective amino acids (the "matched span", as determined by the algorithm). A gap opening penalty (which is calculated as 3 times the average diagonal; the "average diagonal" is the average of the diagonal of the comparison matrix being used; the "diagonal" is the score or number assigned to each perfect amino acid match by the particular comparison matrix) and a gap extension penalty (which is usually {fraction (1/10)} times the gap opening penalty), as well as a comparison matrix such as PAM 250 or BLOSUM 62 are used in conjunction with the algorithm. A standard comparison matrix (see Dayhoff et al., Atlas of Protein Sequence and Structure, vol. 5, supp.3 (1978) for the PAM 250 comparison matrix; Henikoff et al., Proc. Natl. Acad. Sci USA 89, 10915-10919 (1992) for the BLOSUM 62 comparison matrix) is also used by the algorithm. In some embodiments sequence identity is determined using the following parameters, e.g. using the algorithm GAP: Algorithm: Needleman et al., J. Mol. Biol. 48, 443-453 (1970); Comparison matrix: BLOSUM 62 from Henikoff et al., PNAS USA 89, 10915-

10919 (1992); and Gap Penalty: 12, Gap Length Penalty: 4, Threshold of Similarity: 0, and no penalty for end gaps.

In some embodiments the antibody of the invention comprises one or more amino acid substitutions or insertion. Amino acid substitution may be in the form of conservative amino acid substitution. A "conservative amino acid substitution" may involve a substitution of one amino acid residue with another residue such that there is little or no effect on the polarity or charge of the amino acid residue at that position. Conservative amino acid substitution may be carried out within the following groups of amino acids: Hydrophilic: Ala, Pro, Gly, Glu, Asp, Gln, Asn, Ser, Thr; Aliphatic: Val, Ile, Leu, Met. Basic: Lys, Arg, His; Aromatic: Phe, Tyr, Trp; furthermore, typically any residue may be substituted with alanine.

In some embodiments, one or more unnatural amino acids are introduced by substitution or insertion into the antibody of the present invention. Such unnatural amino acids include, but are not limited to, the D-isomers of the common amino acids, 2,4-diaminobutyric acid, α-amino isobutyric acid, 4-aminobutyric acid, 2-aminobutyric acid, 6-amino hexanoic acid, 2-amino isobutyric acid, 3-amino propionic acid, ornithine, norleucine, norvaline, hydroxyproline, sarcosine, citralline, homocitrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, and Nα-methyl amino acids.

Amino acid sequence variants of the antibody of the present invention may be prepared by introducing appropriate nucleotide changes into a nucleic acid of the present invention, or by in vitro synthesis of the desired polypeptide. Such variants include, for example, deletions, insertions or substitutions of residues within the amino acid sequence. A combination of deletion, insertion and substitution can be made to arrive at the final construct, provided that the final polypeptide product possesses the desired characteristics. Variant (altered) polypeptides can be prepared using any technique known in the art. For example, a polynucleotide of the invention can be subjected to in vitro mutagenesis. Such in vitro mutagenesis techniques include sub-cloning the polynucleotide into a suitable vector, transforming the vector into a "mutator" strain such as the *E. coli* XL-I red (Stratagene) and propagating the transformed bacteria for a suitable number of generations. Products derived from mutated/altered DNA can readily be screened using techniques described herein to determine if they have receptor-binding and/or—inhibitory activity. In designing amino acid sequence variants, the location of the mutation site and the nature of the mutation will depend on characteristic(s) to be modified. The sites for mutation can be modified individually or in series, e.g., by (1) substituting first with conservative amino acid choices and then with more radical selections depending upon the results achieved, (2) deleting the target residue, or (3) inserting other residues adjacent to the located site. In some embodiments amino acid sequence deletions range from about 1 to 15 residues, more preferably about 1 to 10 residues, and typically about 1 to 5, contiguous residues.

In some embodiments, a molecule consists essentially of the defined sequence. In some embodiments, a molecule consists of the defined sequence. In some embodiments the antibody is an isolated antibody. The term "isolated antibody" refers to an antibody that has been separated and/or recovered from another/other component(s) of its natural environment and/or purified from a mixture of components in its natural environment. The antibodies of the invention may be from different species including mammalian species such as mouse, rat, rabbit, pig or non-human primate. The antibody may be a rodent antibody and more particularly a mouse antibody. Alternatively, the antibody may be from a non-mammalian species such as chicken. The antibody may further be a humanized antibody or human antibody.

Antibodies of the invention may be prepared according to methods known in the art, such as recombinant protein, cell culture, and immunological techniques. Such techniques are described and explained throughout the literature in sources such as, J. Perbal, A Practical Guide to Molecular Cloning, John Wiley and Sons (1984), J. Sambrook et al, Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley and Sons (including all updates until present).

Single chain antibodies, including scFv or scFv-Fc antibodies, may be prepared by inserting the DNA sequence corresponding to their amino acid sequence into a plasmid in a host cell followed by expression of the antibody using this host cell by recombinant techniques, e.g. bacterial cell culture; such methods are well-known in the art.

Monoclonal antibodies are typically made by fusing myeloma cells with the spleen cells from a mouse that has been immunized with the desired antigen. Human monoclonal antibodies can be obtained from transgenic animals (e.g. mice or other suitable species) encoding human antibodies. Alternatively, recombinant monoclonal antibodies can be made involving technologies, referred to as repertoire cloning or phage display/yeast display. Recombinant antibody engineering involves the use of viruses or yeast to create antibodies, rather than mice.

Methods and Use of Antibodies

In some embodiments the present invention relates to use of the antibodies as defined herein for identifying and/or quantifying liraglutide fibrils or semaglutide fibrils. In some embodiments the present invention relates to use of the antibodies as defined herein for isolating, including partly isolating, liraglutide fibrils or semaglutide fibrils from solutions comprising soluble liraglutide or soluble semaglutide. Such identification and/or quantification may be carried out by binding the antibody to the fibrils followed by detection of bound antibody, for example via an enzyme-linked immunosorbent assay (ELISA). An ELISA may be carried out as known in the art. In some embodiments the container for the ELISA (such as a microtiter plate) is initially saturated. Saturation may be with a protein such as lysozyme or albumin, e.g. bovine serum albumin (BSA) or ovalbumin. In some embodiments the antibody of the invention bound to the fibril will be bound to a secondary antibody. If the antibody of the invention comprises an Fc domain then the secondary antibody may bind to this Fc domain. Detection and/or quantification of the secondary antibody may be possible if a marker is present on the secondary antibody, such a marker may be a fluorophore which can be identified via spectroscopy. Quantification may be carried out using a standard of the fibril bound to the antibody of the invention.

In some embodiments the term "detection limit" as used herein refers to the lowest limit of detection, which is the lowest concentration of a substance which can be distinguished from the absence of this substance. In some embodiments the term "detection limit" as used herein refers to a mixture/soluble specificity ratio of 3 determined according to Assay (IV) herein. Comparisons of detection limits using an antibody and a ThT Assay may be carried according to Assay (VI) herein. Comparisons of detection limits using an antibody and a ThT Assay may be carried according to Assay (VI-B) herein. In some embodiments the term "detection limit" as used herein in relation to an antibody refers to the detection limit of an assay using said antibody in an ELISA, such as Assay (III) or Assay (IV) herein. In some embodiments the term "detection limit" as used herein in relation to an antibody refers to the detection limit of an assay using said antibody in an ELISA, such as Assay (III-B) herein. In some embodiments the term "detection limit" as used herein is three times the standard deviation of the control sample tested in duplicate; standard deviation may be determined by the Student's t-test.

In some embodiments the present invention relates to use of an antibody as defined herein for identification of liraglutide fibrils or semaglutide fibrils.

In some embodiments the present invention relates to use of an antibody as defined herein as an affinity ligand to remove fibrils from a mixture comprising (i) liraglutide fibrils and soluble liraglutide or (ii) semaglutide fibrils and soluble semaglutide.

In some embodiments the present invention relates to methods for identifying liraglutide fibrils or semaglutide fibrils, said method comprising the step of a) binding the antibody as defined herein to liraglutide fibrils or semaglutide fibrils.

In some embodiments the present invention relates to methods for quantifying liraglutide fibrils or semaglutide fibrils, said method comprising the step of a) binding the antibody as defined herein to liraglutide fibrils or semaglutide fibrils. The method according to any one of the preceding embodiments further comprising a step of b) detecting antibody bound to liraglutide fibrils or semaglutide fibrils. In some embodiments the method further comprises a step of c) quantifying antibody bound to liraglutide fibrils or semaglutide fibrils, optionally by use of a standard of said fibril. In some embodiments the fibrils are in a solution.

In some embodiments the fibrils are in a solution further comprising soluble liraglutide. In some embodiments the fibrils are in a solution further comprising no other peptide or protein other than liraglutide fibrils, and optionally soluble liraglutide.

In some embodiments the method comprises (a) contacting a solid support with the sample under conditions whereby one or more fibrils in the sample are immobilized on the solid support; (b) contacting the solid support with any one of the antibodies described herein, or an antigen-binding fragment thereof, under conditions whereby the antibody binds to the one or more immobilized fibrils to form an antibody-fibril complex; and (c) contacting the antibody-fibril complex with a second antibody comprising a detectable label, wherein (i) the second antibody specifically binds to the antibody-fibril complex and (ii) detection of a signal from the detectable label indicating the presence of one or more fibrils in the sample.

In some embodiments, the method comprises (a) contacting a solid support comprising a fibril-specific antibody with a sample such that fibril, if present in the sample, binds to the antibody and is immobilized to the surface to form complex; and (b) detecting the complex.

Any solid support known in the art can be used in the methods described herein, including but not limited to, solid supports made out of polymeric materials in the form of planar substrates or beads, and the like. For example, the solid support may be a slide, multiwell plate, (e.g., 96-well plate), or a bead, e.g., latex, agarose, sepharose, streptavidin, tosylactivated, epoxy, polystyrene, amino bead, amine bead, carboxyl bead, or the like. In certain embodiments, the bead may be a particle, e.g., a microparticle. The terms "bead" and "particle" are used herein interchangeably and refer to a substantially spherical solid support. The terms "microparticle" and "microbead" are used interchangeably herein and refer to a microbead or microparticle that is allowed to occupy or settle in an array of wells, such as, for example, in an array of wells in a detection module. Any number of techniques known in the art may be used to attach a protein or peptide to a solid support, such as a plate or microparticle. A wide variety of techniques are known for adding reactive moieties to proteins, such as, for example, the method described in U.S. Pat. No. 5,620,850. Methods for attachment of proteins to surfaces also are described in, for example, Heller, *Acc. Chem. Res.*, 23: 128 (1990).

The solid support may be contacted with a volume of the sample using any suitable method known in the art. The term "contacting," as used herein, refers to any type of combining action which brings a solid support into sufficiently close proximity with one or more fibrils in a sample such that a binding interaction will occur if one or more fibrils are present in the sample. Contacting may be achieved in a variety of different ways, including combining the sample with a multiwell plate or microparticle. The contacting may be repeated as many times as necessary. The incubating may be in a binding buffer that facilitates the specific binding interaction, such as, for example, albumin (e.g., BSA), non-ionic detergents (Tween-20, Triton X-100), and/or protease inhibitors (e.g., PMSF). Other conditions for the binding interaction, such as, for example, temperature and salt concentration, may also be determined empirically or may be based on manufacturer's instructions. For example, the contacting may be carried out at room temperature (21° C.-28° C., e.g., 23° C.-25° C.), 37° C., or 4° C. The terms "detectable label," and "label," as used herein, refer to a moiety that can produce a signal that is detectable by visual or instrumental means. The detectable label may be, for example, a signal-producing substance, such as a chromogen, a fluorescent compound, an enzyme, a chemiluminescent compound, a radioactive compound, and the like. In one embodiment, the detectable label may be a fluorescent compound, such as a fluorophore. The presence or amount of fibrils in a sample may be determined (e.g., quantified) using any suitable method known in the art. Such methods include, but are not limited to, immunoassays, e.g. ELISA.

In some embodiments the present invention relates to an assay for detecting liraglutide fibrils over soluble and/or monomeric liraglutide comprising an antibody according to the invention, wherein said antibody can detect liraglutide fibrils at concentrations of 1-1000 ppm fibrils in solution, such as 1-10 ppm fibrils, alternatively 10-100 ppm fibrils, alternatively 100-1000 ppm fibrils.

In some embodiments, "a" means "one or more". The term "about" as used herein means the range from minus 10% to plus 10% the value referred to. Unless otherwise indicated in the specification, terms presented in singular form also include the plural situation.

Embodiments of the Invention

Non-limiting embodiments of the invention include:
1. An antibody binding liraglutide fibrils.
2. An antibody binding liraglutide fibrils, wherein said fibrils are prepared according to Assay (I) herein.
3. An antibody binding semaglutide fibrils.
4. An antibody binding semaglutide fibrils, wherein said fibrils are prepared according to Assay (II) herein.
5. The antibody according to any embodiment 1 or 2, wherein said antibody has a detection limit for liraglutide fibrils at a concentration at least 10 times, such as at least 100 times or at least 1000 times, lower than the detection limit for liraglutide fibrils in a ThT assay, said detection limit optionally determined according to Assay (VI) herein.
6. The antibody according to any embodiment 1 or 2, wherein said antibody has a level of binding to liraglutide fibrils which is at least 10 times higher, such as at least 20 times higher or at least 50 times higher, than the level of binding of said antibody to soluble liraglutide.
7. The antibody according to any embodiment 1 or 2, wherein said antibody has a detection limit for liraglutide fibrils at a concentration at least 10 times, such as at least 100 times or at least 1000 times, lower than the detection limit for liraglutide fibrils in a ThT assay, said detection limit optionally determined according to Assay (VI-B) herein.
8. The antibody according to any embodiment 1 or 2, wherein said antibody has a level of binding to liraglutide fibrils which is at least 5 times, such as 10 times, higher than the level of binding of said antibody to soluble liraglutide, said level of binding optionally determined according to Assay (III-B) herein.
9. The antibody according to any embodiment 3 or 4, wherein said antibody has a detection limit for semaglutide fibrils at a concentration at least 10 times, such as at least 100 times or at least 1000 times, lower than the detection limit for semaglutide fibrils in a ThT assay, said detection limit optionally determined according to Assay (VI) herein.
10. The antibody according to embodiment 3 or 4, wherein said antibody has a level of binding to semaglutide fibrils which is at least 10 times higher, such as at least 20 times higher or at least 50 times higher than the level of binding of said antibody to soluble semaglutide.
11. The antibody according to any one of embodiments 6 or 10, wherein said level of binding is determined according to Assay (IV) herein.
12. The antibody according to any one of embodiments 6 or 10, wherein said level of binding is determined according to Assay (III) herein.
13. An antibody binding liraglutide fibrils, wherein the variable region of the heavy chain of said antibody comprises a CDR3 sequence and said CDR3 sequence is selected from the group consisting of SEQ ID NO: 37, 43, 49, 55, 61, 67, 73, 79, 85, 91, 97, 103, or any of said sequences with 1, 2 or 3 amino acid substitutions, deletions or insertions.
14. An antibody binding liraglutide fibrils, wherein the variable region of the heavy chain of said antibody comprises a CDR1, a CDR2, and/or a CDR3 sequence selected from the group consisting of:
    a. SEQ ID NO: 37, 38 and 39;
    b. SEQ ID NO: 43, 44 and 45;
    c. SEQ ID NO: 49, 50 and 51;
    d. SEQ ID NO: 55, 56 and 57;
    e. SEQ ID NO: 61, 62 and 63;
    f. SEQ ID NO: 67, 68 and 69;
    g. SEQ ID NO: 73, 74 and 75;
    h. SEQ ID NO: 79, 80 and 81;
    i. SEQ ID NO: 85, 86 and 87;
    j. SEQ ID NO: 91, 92 and 93;
    k. SEQ ID NO: 97, 98 and 99;
    l. SEQ ID NO: 103, 104 and 105;
    or any of said sequences with 1, 2 or 3 amino acid substitutions, deletions or insertions.
15. An antibody binding liraglutide fibrils, wherein the variable region of the light chain of said antibody comprises a CDR1, a CDR2, and/or a CDR3 sequence selected from the group consisting of:
    a. SEQ ID NO: 40, 41 and 42;
    b. SEQ ID NO: 46, 47 and 48;
    c. SEQ ID NO: 52, 53 and 54;
    d. SEQ ID NO: 58, 59 and 60;
    e. SEQ ID NO: 64, 65 and 66;
    f. SEQ ID NO: 70, 71 and 72;
    g. SEQ ID NO: 76, 77 and 78;
    h. SEQ ID NO: 82, 83 and 84;
    i. SEQ ID NO: 88, 89 and 90;
    j. SEQ ID NO: 94, 95 and 96;
    k. SEQ ID NO: 100, 101 and 102;
    l. SEQ ID NO: 106, 107 and 108;
    or any of said sequences with 1, 2 or 3 amino acid substitutions, deletions or insertions.
16. An antibody binding liraglutide fibrils, wherein said antibody comprises a variable region of the heavy chain as defined in any one of the preceding embodiments and a variable region of the light chain as defined in any one of the preceding embodiments.
17. An antibody binding liraglutide fibrils, wherein said antibody comprises a sequence selected from the group consisting of SEQ ID NO: 1, 2, 3, 4, 5, 6, 7, 8, 9, 10, 11 and 12; or any of said sequences with up to 20, such as up to 15 or up to 10, amino acid substitutions, deletions or insertions.
18. An antibody binding liraglutide fibrils, wherein said antibody has at least 80%, such as at least 90% or at least 95%, sequence identity to a sequence selected from the group consisting of SEQ ID NO: 1, 2, 3, 4, 5, 6, 7, 8, 9, 10, 11 and 12.
19. An antibody binding liraglutide fibrils, wherein said antibody comprises a variable light chain (VL) sequence selected from the group consisting of SEQ ID NO: 13, 15, 17, 19, 21, 23, 25, 27, 29, 31, 33, 35, 111 and 113; or any of said sequences with up to 20, such as up to 15 or up to 10, amino acid substitutions, deletions or insertions.
20. An antibody binding liraglutide fibrils, wherein said antibody comprises a variable heavy chain (VH) sequence selected from the group consisting of SEQ ID NO: 14, 16, 18, 20, 22, 24, 26, 28, 30, 32, 34, 36, 112 and 114; or any of said sequences with up to 20, such as up to 15 or up to 10, amino acid substitutions, deletions or insertions.
21. The antibody according to any one of the preceding embodiments, wherein said antibody is an isolated antibody.
22. The antibody according to any one of the preceding embodiments, wherein said antibody is single chain Fv fragment.
23. The antibody according to any one of the preceding embodiments, wherein said antibody comprises an Fc domain.

24. The antibody according to any one of the preceding embodiments, wherein said antibody is single chain Fv fragment further comprising an Fc domain.
25. The antibody according to any one of the preceding embodiments, wherein said antibody specifically binds said liraglutide fibrils and/or semaglutide fibrils.
26. The antibody according to any one of the preceding embodiments, wherein said antibody specifically binds said liraglutide fibrils.
27. The antibody according to any one of the preceding embodiments, wherein said antibody specifically binds said semaglutide fibrils.
28. Use of an antibody as defined in any one of the preceding embodiments for identification of liraglutide fibrils or semaglutide fibrils.
29. Use of an antibody as defined in any one of the preceding embodiments as an affinity ligand to remove fibrils from a mixture comprising (i) liraglutide fibrils and soluble liraglutide or (ii) semaglutide fibrils and soluble semaglutide.
30. Method for identifying liraglutide fibrils or semaglutide fibrils, said method comprising the step of a) binding the antibody as defined in any one of the preceding embodiments to liraglutide fibrils or semaglutide fibrils.
31. Method for quantifying liraglutide fibrils or semaglutide fibrils, said method comprising the step of a) binding the antibody as defined in any one of the preceding embodiments to liraglutide fibrils or semaglutide fibrils.
32. The method according to any one of the preceding embodiments further comprising a step of b) detecting antibody bound to liraglutide fibrils or semaglutide fibrils.
33. The method according to any one of the preceding embodiments further comprising a step of c) quantifying antibody bound to liraglutide fibrils or semaglutide fibrils, optionally by use of a standard of said fibril.
34. The method according to any one of the preceding embodiments, wherein said fibrils are in a solution.
35. The method according to any one of the preceding embodiments, wherein said fibrils are in a solution further comprising soluble liraglutide.
36. The method according to any one of the preceding embodiments, wherein said fibrils are in a solution further comprising no other peptide or protein other than liraglutide fibrils, and optionally soluble liraglutide.
37. An antibody binding liraglutide fibrils, wherein said fibrils are optionally prepared according to Assay (I) herein and said antibody has
  a. a level of binding to liraglutide fibrils which is at least 10 times higher, such as at least 20 times higher or at least 50 times higher, than the level of binding of said antibody to soluble liraglutide; and/or
  b. a detection limit for liraglutide fibrils at a concentration at least 10 times, such as at least 100 times or at least 1000 times, lower than the detection limit for liraglutide fibrils in a ThT assay, said detection limit optionally determined according to Assay (VI) herein.
38. An antibody binding semaglutide fibrils, wherein said fibrils are optionally prepared according to Assay (II) herein and said antibody has
  c. a level of binding to semaglutide fibrils which is at least 10 times higher, such as at least 20 times higher or at least 50 times higher than the level of binding of said antibody to soluble semaglutide; and/or
  d. detection limit for semaglutide fibrils at a concentration at least 10 times, such as at least 100 times or at least 1000 times, lower than the detection limit for semaglutide fibrils in a ThT assay, said detection limit optionally determined according to Assay (VI) herein.
39. The antibody according to any one of embodiments 37 or 38, wherein said level of binding is determined according to Assay (IV) herein.
40. The antibody according to any one of embodiments 37 or 38, wherein said level of binding is determined according to Assay (III) herein.
41. An antibody binding liraglutide fibrils, wherein the variable region of the heavy chain of said antibody comprises a CDR3 sequence and said CDR3 sequence is selected from the group consisting of SEQ ID NO: 37, 43, 49, 55, 61, 67, 73, 79, 85, 91, 97, 103, 115 and 121, or any of said sequences with 1, 2 or 3 amino acid substitutions, deletions or insertions.
42. An antibody binding liraglutide fibrils, wherein the variable region of the heavy chain of said antibody comprises a CDR3 sequence and said CDR3 sequence is selected from the group consisting of SEQ ID NO: 37, 43, 49, 55, 61, 67, 73, 79, 85, 91, 97, 103, or any of said sequences with 1, 2 or 3 amino acid substitutions, deletions or insertions.
43. An antibody binding liraglutide fibrils, wherein the variable region of the heavy chain of said antibody comprises a CDR1, a CDR2, and/or a CDR3 sequence selected from the group consisting of:
  a. SEQ ID NO: 37, 38 and 39;
  b. SEQ ID NO: 43, 44 and 45;
  c. SEQ ID NO: 49, 50 and 51;
  d. SEQ ID NO: 55, 56 and 57;
  e. SEQ ID NO: 61, 62 and 63;
  f. SEQ ID NO: 67, 68 and 69;
  g. SEQ ID NO: 73, 74 and 75;
  h. SEQ ID NO: 79, 80 and 81;
  i. SEQ ID NO: 85, 86 and 87;
  j. SEQ ID NO: 91, 92 and 93;
  k. SEQ ID NO: 97, 98 and 99;
  l. SEQ ID NO: 103, 104 and 105;
  or any of said sequences with 1, 2 or 3 amino acid substitutions, deletions or insertions.
44. An antibody binding liraglutide fibrils, wherein the variable region of the light chain of said antibody comprises a CDR1, a CDR2, and/or a CDR3 sequence selected from the group consisting of:
  a. SEQ ID NO: 40, 41 and 42;
  b. SEQ ID NO: 46, 47 and 48;
  c. SEQ ID NO: 52, 53 and 54;
  d. SEQ ID NO: 58, 59 and 60;
  e. SEQ ID NO: 64, 65 and 66;
  f. SEQ ID NO: 70, 71 and 72;
  g. SEQ ID NO: 76, 77 and 78;
  h. SEQ ID NO: 82, 83 and 84;
  i. SEQ ID NO: 88, 89 and 90;
  j. SEQ ID NO: 94, 95 and 96;
  k. SEQ ID NO: 100, 101 and 102;
  l. SEQ ID NO: 106, 107 and 108;
  or any of said sequences with 1, 2 or 3 amino acid substitutions, deletions or insertions.
45. An antibody binding liraglutide fibrils, wherein said antibody comprises a variable region of the heavy chain as defined in any one of the preceding embodiments and a variable region of the light chain as defined in any one of the preceding embodiments.
46. An antibody binding liraglutide fibrils, wherein said antibody comprises a sequence selected from the group consisting of SEQ ID NO: 1, 2, 3, 4, 5, 6, 7, 8, 9, 10, 11 and 12; or any of said sequences with up to 20, such as up to 15 or up to 10, amino acid substitutions, deletions or insertions.

47. An antibody binding liraglutide fibrils, wherein said antibody has at least 80%, such as at least 90% or at least 95%, sequence identity to a sequence selected from the group consisting of SEQ ID NO: 1, 2, 3, 4, 5, 6, 7, 8, 9, 10, 11 and 12.

48. The antibody according to any one of the preceding embodiments, wherein said antibody is an isolated antibody.

49. The antibody according to any one of the preceding embodiments, wherein said antibody is single chain Fv fragment.

50. The antibody according to any one of the preceding embodiments, wherein said antibody comprises an Fc domain.

51. The antibody according to any one of the preceding embodiments, wherein said antibody is single chain Fv fragment further comprising an Fc domain.

52. The antibody according to any one of the preceding embodiments, wherein said antibody specifically binds said liraglutide fibrils and/or semaglutide fibrils.

53. The antibody according to any one of the preceding embodiments, wherein said antibody specifically binds said liraglutide fibrils.

54. The antibody according to any one of the preceding embodiments, wherein said antibody specifically binds said semaglutide fibrils.

55. Use of an antibody as defined in any one of the preceding embodiments for identification of liraglutide fibrils or semaglutide fibrils.

56. Use of an antibody as defined in any one of the preceding embodiments as an affinity ligand to remove fibrils from a mixture comprising (i) liraglutide fibrils and soluble liraglutide or (ii) semaglutide fibrils and soluble semaglutide.

57. Method for identifying liraglutide fibrils or semaglutide fibrils, said method comprising the step of a) binding the antibody as defined in any one of the preceding embodiments to liraglutide fibrils or semaglutide fibrils.

58. Method for quantifying liraglutide fibrils or semaglutide fibrils, said method comprising the step of a) binding the antibody as defined in any one of the preceding embodiments to liraglutide fibrils or semaglutide fibrils.

59. The method according to any one of the preceding embodiments further comprising a step of b) detecting antibody bound to liraglutide fibrils or semaglutide fibrils.

60. The method according to any one of the preceding embodiments further comprising a step of c) quantifying antibody bound to liraglutide fibrils or semaglutide fibrils, optionally by use of a standard of said fibril.

61. The method according to any one of the preceding embodiments, wherein said fibrils are in a solution.

62. The method according to any one of the preceding embodiments, wherein said fibrils are in a solution further comprising soluble liraglutide.

63. The method according to any one of the preceding embodiments, wherein said fibrils are in a solution further comprising no other peptide or protein other than liraglutide fibrils, and optionally soluble liraglutide.

64. An antibody binding liraglutide fibrils, wherein the variable region of the heavy chain of said antibody comprises a CDR1, a CDR2, and/or a CDR3 sequence selected from the group consisting of:
    m. SEQ ID NO: 115, 116 and 117;
    n. SEQ ID NO: 121, 122, 123;
    or any of said sequences with 1, 2 or 3 amino acid substitutions, deletions or insertions.

65. An antibody binding liraglutide fibrils, wherein the variable region of the light chain of said antibody comprises a CDR1, a CDR2, and/or a CDR3 sequence selected from the group consisting of:
    aa. SEQ ID NO: 118, 119 and 120;
    bb. SEQ ID NO: 124, 125 and 126;
    or any of said sequences with 1, 2 or 3 amino acid substitutions, deletions or insertions.

66. An antibody binding liraglutide fibrils, wherein said antibody comprises a variable region of the heavy chain as defined in any one of the preceding embodiments and a variable region of the light chain as defined in any one of the preceding embodiments.

67. An antibody binding liraglutide fibrils, wherein said antibody comprises a sequence selected from the group consisting of SEQ ID NO: 109 and 110; or any of said sequences with up to 20, such as up to 15 or up to 10, amino acid substitutions, deletions or insertions.

68. An antibody binding liraglutide fibrils, wherein said antibody has at least 80%, such as at least 90% or at least 95%, sequence identity to a sequence selected from the group consisting of SEQ ID NO: 109 and 110.

69. The antibody according to any one of embodiments 37-68, wherein said antibody comprises a variable light chain (VL) sequence selected from the group consisting of SEQ ID NO: 13, 15, 17, 19, 21, 23, 25, 27, 29, 31, 33, 35, 111 and 113; or any of said sequences with up to 20, such as up to 15 or up to 10, amino acid substitutions, deletions or insertions.

70. The antibody according to any one of embodiments 37-69, wherein said antibody comprises a variable heavy chain (VH) sequence selected from the group consisting of SEQ ID NO: 14, 16, 18, 20, 22, 24, 26, 28, 30, 32, 34, 36, 112 and 114; or any of said sequences with up to 20, such as up to 15 or up to 10, amino acid substitutions, deletions or insertions.

71. The antibody according to any one of embodiments 37-70, wherein said antibody is an isolated antibody.

72. The antibody according to any one of embodiments 37-71, wherein said antibody is single chain Fv fragment.

73. The antibody according to any one of embodiments 37-72, wherein said antibody comprises an Fc domain.

74. The antibody according to any one of embodiments 37-73, wherein said antibody is single chain Fv fragment further comprising an Fc domain.

75. The antibody according to any one of embodiments 37-74, wherein said antibody specifically binds said liraglutide fibrils and/or semaglutide fibrils.

76. The antibody according to any one of embodiments 37-75, wherein said antibody specifically binds said liraglutide fibrils.

77. The antibody according to any one of embodiments 37-76, wherein said antibody specifically binds said semaglutide fibrils.

78. The antibody according to any one of embodiments 37-77, wherein said fibrils are optionally prepared according to Assay (I) herein and said antibody has
    a. a level of binding to liraglutide fibrils which is at least 10 times higher than the level of binding of said antibody to soluble liraglutide, wherein said level of binding is determined according to Assay (Ill) at a liraglutide fibril concentration of at least 25 µM; and/or
    b. a detection limit for liraglutide fibrils at a concentration at least 10 times lower than the detection limit for liraglutide fibrils in a ThT assay, wherein said detection limit is determined according to Assay (VI) herein at a liraglutide fibril concentration of at least 1 µM; and/or c. a level of binding to liraglutide fibrils which is at least 5 times higher than the level of binding of said antibody to soluble liraglutide, wherein said antibody has a purity of above 95% monomer and wherein said level of binding is determined according to Assay (III-B) herein at a liraglutide fibril concentration of at least 30 µM; and/or d. a detection limit for liraglutide fibrils at a concentration at least 10 times lower than the detection limit for liraglutide fibrils in a ThT assay, wherein said antibody has a purity of above 95% monomer and wherein said detection limit is determined according to Assay (VI-B) herein at a liraglutide fibril concentration of at least 0.025 µM.

79. The antibody according to any one of embodiments 37-78, wherein said antibody can detect liraglutide fibrils at concentrations of 1-1000 ppm fibrils in solution, such as 1-10 ppm fibrils, alternatively 10-100 ppm fibrils, alternatively 100-1000 ppm fibrils.

80. The antibody according to any one of embodiments 37-79, wherein said antibody has a purity of above 70%, alternatively above 75%, alternatively above 80%, alternatively above 85%, alternatively above 90%, alternatively above 95% monomer.

81. The antibody according to any one of embodiments 37-80, wherein said antibody has a purity of above 95% monomer.

82. Use of an antibody as defined in any one of embodiments 37-81 for identification of liraglutide fibrils or semaglutide fibrils.

83. Use of an antibody as defined in any one of embodiments 37-81 as an affinity ligand to remove fibrils from a mixture comprising (i) liraglutide fibrils and soluble liraglutide or (ii) semaglutide fibrils and soluble semaglutide.

84. Method for identifying liraglutide fibrils or semaglutide fibrils, said method comprising the step of a) binding the antibody as defined in any one of embodiments 37-81 to liraglutide fibrils or semaglutide fibrils.

85. Method for quantifying liraglutide fibrils or semaglutide fibrils, said method comprising the step of a) binding the antibody as defined in any one of embodiments 37-81 to liraglutide fibrils or semaglutide fibrils.

86. The method according to any one of embodiments 84-85 further comprising a step of b) detecting antibody bound to liraglutide fibrils or semaglutide fibrils.

87. The method according to any one of embodiments 84-86 further comprising a step of c) quantifying antibody bound to liraglutide fibrils or semaglutide fibrils, optionally by use of a standard of said fibril.

88. The method according to any one of embodiments 84-87, wherein said fibrils are in a solution.

89. The method according to any one of embodiments 84-88, wherein said fibrils are in a solution further comprising soluble liraglutide.

90. The method according to any one of embodiments 84-89, wherein said fibrils are in a solution further comprising no other peptide or protein other than liraglutide fibrils, and optionally soluble liraglutide.

91. An assay for selectively detecting liraglutide fibrils over soluble and/or monomeric liraglutide comprising an antibody as defined in any one of embodiments 37-81, wherein said antibody can detect liraglutide fibrils at concentrations of 1-1000 ppm fibrils in solution, such as 1-10 ppm fibrils, alternatively 10-100 ppm fibrils, alternatively 100-1000 ppm fibrils.

EXAMPLES

List of Abbreviations

PBS: Phosphate buffered saline (aqueous solution of 137 mM NaCl, 2.7 mM KCl, 10 mM $Na_2HPO_4$, 1.8 mM $KH_2PO_4$ adjusted to pH 7.4)
PES: Polyethersulfone
scFv-Fc: Single chain variable fragment linked to Fc domain
ThT: Thioflavin T Materials and Methods Antibody Library Preparation, Sorting and Cloning of Selected Antibody Variants The antibodies were isolated through two stages of library sorting. In the first stage of sorting, a single-chain variable fragment (scFv) yeast surface display library was generated by diversification of heavy chain CDR3 (HCDR3) of the 4D5 scFv (Julian et al., 2019; Stimple et al., 2019; Tiller et al., 2017). The scFv's were genetically fused to the C-terminus of the yeast Aga2 protein through a flexible linker, enabling antibody display on the cell surface. Yeast-displayed antibody libraries were sorted for binding to liraglutide fibrils (and soluble liraglutide as a control) immobilized on magnetic beads (Dynabeads M-280 Tosylactivated, 14203, Invitrogen). To prepare the beads, $8 \times 10^7$ beads were first washed (2×) with 1 mL of sterile PBS. Soluble liraglutide (100 µg, from 6 mg/mL stock in drug composition buffer) was diluted into PBS containing the magnetic beads (final volume of 800 µL) and coupled to the beads overnight (4° C. without agitation). For beads coated with fibrillar liraglutide, 100 µg of liraglutide fibrils was coupled to the beads in 800 µL of PBS overnight at room temperature with end-over-end mixing. The following day, the beads were washed (2×) with 1 mL PBS supplemented with 10 mM glycine in order to quench unreacted toluenesulfonyl groups on the beads, and then washed (2×) using 1 mL PBS supplemented with 1 g/L BSA (PBS-B) before incubation with yeast. Eight rounds of positive selections were performed against beads coated with liraglutide fibrils in PBS-B supplemented with 1 milk. In order to isolate yeast harboring conformationally-specific antibodies against liraglutide fibrils, the final three rounds of sorting incorporated negative selections performed against beads coated with soluble liraglutide in PBS-B prior to the positive selection against liraglutide fibrils.

In the second stage of library sorting (affinity maturation), a sub-library was designed for one of the best clones from the first stage of sorting. The second-generation library diversified sites in LCDR1, LCDR3 and HCDR2. This library was subjected to four rounds of selection against liraglutide fibrils. The first two rounds of sorting incorporated two sequential negative selections against soluble liraglutide (immobilized on magnetic beads) prior to a positive selection against immobilized liraglutide fibrils. Negative selections were performed in PBS-B, while positive selections were conducted in PBS-B supplemented with 1% milk. We also performed three sequential negative selections in rounds 3 and 4 against beads coated with glucagon fibrils. The beads coated with glucagon fibrils were prepared as previously described (Stimple et al., 2019).

Selected antibodies were cloned into the mammalian expression vector anti-Notch1_6-pBIOCAM5, as described previously (Stimple et al., 2019). Briefly, the insert and the backbone plasmids were digested with NcoI and NotI, purified and ligated. The insertion of the scFv coding fragments was confirmed by Sanger sequencing. These plasmids express a bivalent scFv-human Fc fusion protein with 6×His and 3×FLAG tags on the C-terminal of the antibodies.

Antibody Expression and Purification

Proteins were expressed with the Expi293F Expression System (Catalog Number A14635). Expi293F cells were subcultured and expanded until the cells reached a density of approximately 3-5 million viable cells per mL. Plasmids (30 µg) were transfected into 25 mL of Expi293 cells. Complexes of ExpiFectamine 293 and plasmid DNA were prepared as described in the manufacturer's guidance. Briefly, plasmid DNA and ExpiFectamine reagent were diluted with Opti-MEM medium and mixed via gentle pipetting. After 5 min of incubation, the diluted transfection reagent was mixed with the diluted DNA. The complexes of transfection reagent and DNA were incubated at room temperature for 20 min and added to the Expi293 cells. Cells were incubated at 37° C. and 5% $CO_2$ with shaking. Per the manufacturer's instructions, enhancer 1 and 2 solutions were added to the cells after 20 h (post transfection). After 3 d, the media containing secreted antibody was harvested and centrifuged at 3400×g for 45 min to remove the cells and associated debris.

Antibodies were purified using Protein A chromatography. Protein A beads (20334, Thermo Fisher Scientific) were washed with PBS and incubated with glycine buffer (pH 2.5) for 20 mins. Next, the beads were washed with PBS and then 0.5 mL of beads were added to 30 mL of clarified media and incubated overnight at 4° C. On the following day, media with Protein A beads was added to a 10 mL purification column (89898, Thermo Fisher Scientific). The beads were collected through vacuum filtration and washed with PBS (100 mL) thoroughly. The Protein A beads were then incubated with 2 mL of 0.1 M glycine buffer (pH 3.0) for 15 min and the buffer (with eluted protein) was collected by centrifugation.

The eluted antibodies were then buffer exchanged into PBS using Zeba Spin Desalting Columns (89891, Thermo Fisher Scientific). Protein concentrations were assayed via absorbance measurements at 280 nm (extinction coefficients of 168,460-205,360 $M^{-1}$ $cm^{-1}$).

Size-Exclusion Chromatography

Analytical and preparative size-exclusion chromatography (SEC) experiments were performed using a Shimadzu Prominence HPLC System. The running buffer was 137 mM sodium chloride, 2.7 mM sodium-potassium, 10 mM disodium hydrogen phosphate, 1.8 mM potassium dihydrogen phosphate and 200 mM arginine. The column flow rate was 0.75 mL/min. The antibody samples (0.1 mg/mL) were injected (100 µL) into the column (GE 28990944, Superdex 200 Increase 10/300 GL column, 10 mm inner diameter, 300 mm length), and absorbance signals were monitored at 220 and 280 nm. For preparative SEC, the monomeric fraction was isolated using an FRC-10A fraction collector.

Assay (I): Preparation of Liraglutide Fibrils

Test solution of 6 mg/mL liraglutide was prepared in drug composition buffer (14.0 mg/mL propylene glycol, 5.5 mg/mL phenol, 1.42 mg/mL disodium hydrogen phosphate dihydrate) and final pH adjusted to 8.15 using NaOH and/or HCl if needed, followed by syringe-filtering (0.22 µm PES filter). Aliquots of 1 mL liraglutide solution were distributed into microcentrifuge tubes, a single 3 mm glass bead (Sigma Z265926) added to each tube, and the tubes incubated in a thermomixer at 37° C., orbital shaking at 300 rpm for 15-20 days.

Positive ThT signal was used to monitor fibril formation by removal a small sample of test solution from the tubes (~75 pµL) which was analyzed according to the Assay (V) (ThT Assay) described herein. When the sample showed at least 5-fold higher fluorescence than freshly prepared test solution in the Assay (V) (ThT Assay) herein, then fibrils were sedimented at 221,000×g (1 hour, 4° C.). Fibrils, e.g. gel-like fibrils, were observed at the bottom of the tube. The supernatant was removed from the tube (keeping the supernatant for analysis by Assay (VII) (BCA Assay) herein). The pellet was gently washed with drug composition buffer at pH 8.15 once (without disturbing the pellet) and then resuspended in the original volume of drug composition buffer at pH 8.15 (taking into account any volume removed for ThT analysis) and stored at 4° C. Concentration of fibrils was determined according to Assay (VII) herein; it is important to resuspend the fibril pellets in the exact same total volume after centrifugation for this calculation to be accurate.

Assay (II): Preparation of Semaglutide Fibrils

Test solution of 6 mg/mL semaglutide, optionally with 50 mM NaCl, and drug composition buffer (14.0 mg/mL propylene glycol, 5.5 mg/mL phenol, 1.42 mg/mL disodium hydrogen phosphate dihydrate) adjusted to pH 6.9 (using NaOH and/or HCl if needed) was placed in aliquots of 1 mL in microcentrifuge tubes, a single 3 mm glass bead (Sigma Z265926) added to each tube, and the tubes incubated in a thermomixer at 37° C., orbital shaking at 300 rpm for 15-20 days.

Positive ThT signal was used to monitor fibril formation by removal a small sample of test solution from the tubes (~75 µL) which was analyzed according to the Assay (V) (ThT Assay) described herein. When the sample showed at least 5-fold higher fluorescence than freshly prepared semaglutide in drug composition buffer at pH 6.9 in the Assay (V) (ThT Assay), then fibrils were sedimented at 221,000×g (1 hour, 4° C.). Fibrils, e.g. gel-like fibrils, were observed at the bottom of the tube. The supernatant was removed from the tube (keeping the supernatant for analysis by Assay (VII) (BCA Assay)). The pellet was gently washed with drug composition buffer at pH 6.9 once (without disturbing the pellet) and then resuspended in the original volume of drug composition buffer at pH 6.9 (taking into account any volume removed for ThT analysis) and stored at 4° C. Concentration of fibrils was determined according to Assay (VII) herein; it is important to resuspend the fibril pellets in the exact same total volume after centrifugation for this calculation to be accurate.

Assay (III): Antibody Specificity Ratio (Method 1)

Antibody specificity ratio was determined as follows:
1. ELISA plate preparation (3 plates):
   a. For fibril-coated ELISA plate: Liraglutide fibrils prepared according to Assay (I) herein were resuspended in drug composition buffer (with fibril concentration determined by Assay (VII) (BCA assay) herein), approx. 300 µL of sample sonicated on ice in a microcentrifuge tube (3 cycles of 10 s on/30 s off at 100% amplitude; FB-120 Sonic Dismembrator, Thermo Fisher Scientific). The solution was diluted to 25 µM liraglutide fibrils in PBS and 100 µL sample was distributed into each well of a 96-well Nunc MaxiSorp ELISA plate (Product number: 439454).
  b. For soluble liraglutide-coated plate: 6 mg/mL liraglutide was solubilized in drug composition buffer (14 mg/mL Propylene Glycol, 5.5 mg/mL Phenol, 1.42 mg/mL disodium phosphate dihydrate), pH adjusted to 8.15 using NaOH and/or HCl if needed, and the solution was filtered through a 0.22 µm PES filter. The solution was diluted to 25 µM liraglutide in PBS and 100 µL sample was distributed into each well of a 96-well Nunc MaxiSorp ELISA plate (Product number: 439454).
    i. For "background" plate: 100 µL PBS was distributed into each well of a 96-well Nunc MaxiSorp ELISA plate (Product number: 439454).
2. The plates were covered with adhesive film, wrapped in aluminum foil, and incubated at 4° C. overnight.
3. The next day, plates were washed three times by addition of 300 µL PBS to each well.
4. The plates were blocked by addition of 300 µL PBS supplemented with 0.1% Tween20 and 10 g/L BSA to each well. The plates were then covered with adhesive film, wrapped in aluminum foil, and incubated at room temperature for 3 hours.
5. While the plates were being blocked, the antibody samples were spinned in a centrifuge for 5 minutes at 21,000×g, and concentration of the supernatant measured by absorbance at 280 nm. Each antibody was serially diluted to 5 nM in PBS supplemented with 0.1% Tween20 and 1 g/L BSA.
6. The plates were washed three times by addition of 300 µL PBS to each well
7. 100 µL of antibody solution was distributed into each well. Each antibody was tested in duplicate (i.e. 2 wells for each antibody per plate). The plates were then covered with adhesive film, wrapped in aluminum foil, and incubated for 1 hour at room temperature.
8. The secondary antibody solution was prepared by diluting the secondary antibody (goat anti-human IgG-Fc HRP-conjugate, Invitrogen A18817, stock concentration: 0.5 mg/mL in 50% glycerol) 1:1000 into PBS supplemented with 0.1% Tween20 and 10 g/L BSA.
9. The plates were washed three times by addition of 300 µL PBS to each well.
10. 100 µL of secondary antibody solution was distributed into each well. The plates were then covered with adhesive film, wrapped in aluminum foil, and incubated for 1 hour at room temperature. During the secondary antibody incubation, 1-Step Ultra-TMB ELISA substrate (Thermo Fisher Scientific, 34208) was removed from the refrigerator to equilibrate the solution to room temperature and 2 M (4 N) H2SO4 was prepared.
11. The plates were washed three times by addition of 300 µL PBS to each well.
12. 100 µL Ultra-TMB was added into each well and incubated until yellow product was formed (5-10 minutes).
13. Reaction was quenched by addition of 100 µL 2 M $H_2SO_4$.
14. Absorbance of each well was read at 450 nm in microplate reader (BioTek Synergy Neo).
  Calculations: The ratio of the ELISA signal (absorbance at 450 nm) was calculated for each antibody against fibril-coated plates to its signal against soluble liraglutide-coated plates and to the background plate. These ratios are the fibril/soluble ratio and fibril/background ratios reported herein. For instance: if an antibody gave signals of 1.5 for liraglutide fibrils, 0.05 for soluble liraglutide, and 0.1 for the background plate then the fibril/soluble ratio would be 1.5/0.05=30 and the fibril/background ratio would be: 1.5/0.1=15.

Assay (III-B): Antibody Specificity Ratio (Method 1B)

1. On the night before the assay: BSA was solubilized at 1 mg/mL in PBS, then filter sterilized through a 0.22 µm PES filter with a 30 cc luer-lock syringe, and 150 µL of the solution distributed into each well of a Nunc MaxiSorp (Product number: 439454) 96-well ELISA plate. The plates were covered with adhesive film, wrapped in aluminium foil, and incubated at 4° C. overnight.
2. ELISA plates (coated with BSA) were removed from the refrigerator and wells washed 3 times with 300 µL PBS.
  a. For fibril-coated ELISA plate: Liraglutide fibrils prepared according to Assay (I) herein were resuspended in drug composition buffer (with fibril concentration determined by Assay (VII) (BCA assay) herein), approx. 300 µL of sample sonicated on ice in a microcentrifuge tube (3 cycles of 10 s on/30 s off at 100% amplitude; FB-120 Sonic Dismembrator, Thermo Fisher Scientific). The solution was diluted to 10 µM liraglutide fibrils in PBS and 100 µL sample was distributed into each well.
  b. For soluble liraglutide-coated plate: 6 mg/mL liraglutide was solubilized in drug composition buffer (14 mg/mL Propylene Glycol, 5.5 mg/mL Phenol, 1.42 mg/mL disodium phosphate dihydrate), pH adjusted to 8.15 using NaOH and/or HCl if needed, and the solution was filtered through a 0.22 µm PES filter. The solution was diluted to 10 µM liraglutide in PBS and 100 µL sample was distributed into each well
    i. For "background" plate: 100 µL PBS was distributed into each well of a 96-well Nunc MaxiSorp ELISA plate (Product number: 439454).
3. The plates were covered with adhesive film, wrapped in aluminum foil, and incubated without agitation for 3 hours at room temperature.
4. During this 3 hours, the antibody samples were spun in a centrifuge for 5 minutes at 21,000×g, and concentration of the supernatant measured by absorbance at 280 nm. Each antibody was serially diluted to 5 nM (unless the concentration is stated otherwise) in PBS supplemented with 0.1% Tween20 and 1 g/L BSA.
5. The plates were washed three times by addition of 300 µL PBS to each well.
6. 100 µL of antibody solution was distributed into each well. The plates were then covered with adhesive film, wrapped in aluminum foil, and incubated for 1 hour at room temperature.
7. The secondary antibody solution was prepared by diluting the secondary antibody (goat anti-human IgG-Fc HRP-conjugate, Invitrogen A18817, stock concentration: 0.5 mg/mL in 50% glycerol) 1:1000 into PBS supplemented with 0.1% Tween20 and 10 g/L BSA.
8. The plates were washed three times by addition of 300 µL PBST (PBS supplemented with 0.1% Tween20) to each well.
9. 100 µL of secondary antibody solution was distributed into each well. The plates were then covered with adhesive film, wrapped in aluminum foil, and incubated for 1 hour at room temperature. During the secondary antibody incubation, 1-Step Ultra-TMB ELISA substrate (Thermo Fisher Scientific, 34208) was removed from the refrigerator to equilibrate the solution to room temperature and 2 M (4 N) $H_2SO_4$ was prepared.
10. The plates were washed three times by addition of 300 µL PBST to each well.
11. 100 µL Ultra-TMB was added into each well and incubated until yellow product was formed (5-10 minutes).
12. Reaction was quenched by addition of 100 µL 2 M $H_2SO_4$.
13. Absorbance of each well was read at 450 nm in microplate reader (BioTek Synergy Neo). Calculations: The ratio of the ELISA signal (absorbance at 450 nm) was calculated for each antibody against fibril-coated plates to its signal against soluble liraglutide-coated plates and to the background plate. These ratios are the fibril/soluble ratio and fibril/background ratios reported herein. For instance: if an antibody gave signals of 1.5 for liraglutide fibrils, 0.05 for soluble liraglutide, and 0.1 for the background plate then the fibril/soluble ratio would be 1.5/0.05=30 and the fibril/background ratio would be: 1.5/0.1=15.

Assay (IV): Antibody Specificity Ratio (Method 2)

Antibody specificity ratio was determined as follows:
On the night before the assay: BSA was solubilized at 1 mg/mL in PBS, then filter sterilized through a 0.22 µm PES filter with a 30 cc luer-lock syringe, and 150 µL of the solution distributed into each well of a Nunc MaxiSorp (Product number: 439454) 96-well ELISA plate. The plates were covered with adhesive film, wrapped in aluminium foil, and incubated at 4° C. overnight.
On the day of the assay:
1. Liraglutide was solubilized at 60 mg/mL in the drug composition buffer (14 mg/mL Propylene Glycol, 5.5 mg/mL Phenol, 1.42 mg/mL disodium phosphate dihydrate), pH adjusted to 8.15 using NaOH and/or HCl if needed, and filtered through a 0.22 µm PES filter. The solution was dilute to 6 mg/mL (1600 µM) liraglutide in PBS. This solution is referred to as "solution of soluble liraglutide".
2. Liraglutide fibrils (hereafter: fibrils), obtained according to Assay (I) herein, resuspended in drug composition buffer at pH 8.15 (with concentration of fibrils determined by Assay (VII) (BCA assay) herein) in a sample of approx. 300 µL were sonicated on ice in a microcentrifuge tube (3 cycles of 10 s on/30 s off at 100% amplitude; FB-120 Sonic Dismembrator, Thermo Fisher Scientific). This solution is referred to as "solution of fibrils".
3. The sonicated solution of fibrils was diluted into the solution of soluble liraglutide, such that the final concentration of fibril was 100 µM. The solution was then further serially diluted into solution of soluble liraglutide to resulting samples of 0.1 µM fibril. Two controls were used: i) PBS (no peptide), and ii) no fibril (only solution of soluble liraglutide).
4. ELISA plates (coated with BSA) were removed from the refrigerator and wells washed 3 times with 300 µL PBS.
5. 100 µL of each sample or control from (3) above was distributed into the wells of the freshly-washed plate, and the plate was covered with adhesive film, wrapped in aluminum foil, and incubated at without agitation for 3 hours at room temperature.
6. During the above 3 hour incubation, ~75 µL of antibody to be tested (e.g. scFv-Fc fusion protein) was spun at 21,000×g for 5 minutes to sediment any particulates. The supernatant was removed and A280 nm of this supernatant was determined in order to calculate the concentration of antibody. The antibody was serially diluted to 5 nM in PBS+0.1% Tween20+1 g/L BSA and kept on ice until use.
7. At end of the 3 hour incubation, the well of the plates were washed 3 times with 300 µL PBS.
8. 100 µL of 5 nM antibody was added into each well. The plate was covered with adhesive film, wrapped in aluminum foil, and incubated at room temperature for 1 hour.
9. During the above 1 hour incubation, the secondary antibody (goat anti-human IgG-Fc HRP-conjugate, Invitrogen A18817, stock concentration: 0.5 mg/mL in 50% glycerol) was diluted 1:1000 into PBS+0.1% Tween20+ 10 g/L BSA.
10. At end of the 1 hour incubation, the wells were washed 3 times with 300 µL PBS.
11. 100 µL of secondary antibody solution was added to each well. The plate was covered with adhesive film, wrapped in aluminum foil, and incubated at room temperature for 1 hour.
12. During the secondary antibody incubation, 1-Step Ultra-TMB ELISA substrate (Thermo Fisher Scientific, 34208) was removed from the refrigerator to equilibrate the solution to room temperature. 2 M (4 N) $H_2SO_4$ was prepared.
13. At end of the 1 hour incubation, the wells were washed 3 times with 300 µL PBS.
14. 100 µL Ultra-TMB was added into each well and incubated for 10 minutes.
15. Reaction was quenched by addition of 100 µL 2 M $H_2SO_4$.
16. Absorbance at 450 nm was read in a microplate reader (BioTek Synergy Neo).

Calculations: ELISA signal for each antibody in wells comprising fibrils was divided by the ELISA signal for that same antibody in the control wells with soluble liraglutide and no fibrils. This ratio is the mixture/soluble specificity ratio. For instance: if a given antibody gave a signal of 1.5 for 0.1 µM liraglutide fibrils in mixture with soluble liraglutide, and a signal of 0.05 for soluble liraglutide (lacking fibrils): The mixture/soluble specificity ratio would be 1.5/0.05=30.

Assay (V): ThT Assay

Test solution of peptide was analysed for presence of fibrils immediately after fibril formation. Peptide concentration prior to fibril formation was 6 mg/ml. The peptide may be liraglutide or semaglutide. Liraglutide fibrils may be prepared according to Assay (I) herein. Semaglutide fibrils may be prepared according to Assay (II) herein. A 75 µL sample of the test solution was mixed with 1.36 µL of ThT stock solution (stock concentration: 2200 µM ThT) to achieve a final ThT concentration of 40 µM in the peptide/ThT mixture. For liraglutide, the final concentration in this mixture was 1571 µM liraglutide (calculated prior to fibrillation). A 50 µL sample of the peptide/ThT mixture was added to the wells of black 384-well plates (Fisherbrand 384 Well Polystyrene Plates, 12566624, Thermo Fisher Scientific), and after 5-10 minutes ThT fluorescence ($\lambda$ex=444 nm, $\lambda$em=482 nm) values were measured using a Biotek Synergy Neo microplate reader.

Assay (VI): ThT Assay Compared to Antibody Assay

Detection of liraglutide fibrils in mixtures with soluble liraglutide was determined with ThT detection methods compared to antibody assay.

1. Liraglutide was solubilized at 60 mg/mL in the drug composition buffer (14 mg/mL Propylene Glycol, 5.5 mg/mL Phenol, 1.42 mg/mL disodium phosphate dihydrate), pH adjusted to 8.15 using NaOH and/or HCl if needed, and filtered through a 0.22 μm PES filter. The solution was diluted to 6 mg/mL (1600 μM) liraglutide in PBS. This solution is referred to as "solution of soluble liraglutide".
2. Liraglutide fibrils (hereafter: fibrils), obtained according to Assay (I) herein, resuspended in drug composition buffer at pH 8.15 (with concentration of fibrils determined by Assay (VII) (BCA assay) herein) in a sample of approx. 300 μL were sonicated on ice in a microcentrifuge tube (3 cycles of 10 s on/30 s off at 100% amplitude, FB-120 Sonic Dismembrator, Thermo Fisher Scientific). This solution is referred to as "solution of fibrils".
3. The sonicated solution of fibrils was diluted into the solution of soluble liraglutide, such that the final concentration of fibril was 100 μM. The solution was then further serially diluted into solution of soluble liraglutide to resulting samples of 0.001, 0.0025, 0.01, 0.025, 0.1, 0.25, 1, 2.5, 10, and 25 μM fibril. Two controls were used: i) PBS (no peptide), and ii) no fibril (only solution of soluble liraglutide)
   a. At this point, the solutions obtained by diluting the solution of fibrils into the solution of soluble liraglutide (from step 3) were added (100 μL) to wells of ovalbumin-coated ELISA plates and incubated for 2 hours at room temperature before ELISA detection with antibodies of the invention. The remaining ELISA protocol was performed as described in Assay (IV) (step 7 onwards).
4. The residual samples (mixtures of fibrils and soluble liraglutide, as well as the PBS control and soluble liraglutide control from step 3) were incubated in microcentrifuge tubes at room temperature for 2.5 hours.
5. A Thioflavin T (ThT) stock solution was prepared at a concentration of 2200 μM. ThT was added to the samples (initially at total peptide concentration of 1600 μM) to a final concentration of 40 μM, and a 50 μL sample of the peptide/ThT mixtures was added to the wells of black 384-well plates (Fisherbrand 384 Well Polystyrene Plates, 12566624, Thermo Fisher Scientific). ThT fluorescence (λex=444 nm, λem=482 nm) values were measured for each sample using a Biotek Synergy Neo microplate reader. The final (total) peptide concentration in the peptide/ThT mixture was 1571 μM (calculated prior to fibrillation).
6. The fluorescence measurements for the solutions comprising fibrils were divided by the fluorescence measurement for the solution of soluble liraglutide (no fibril control), and the ratio was reported as mixture/soluble ratio.

Assay (VI-B): ThT Assay Compared to Antibody Assay

Detection of liraglutide fibrils in mixtures with soluble liraglutide was determined with ThT detection methods compared to antibody assay.

1. On the night before the assay: BSA was solubilized at 1 mg/mL in PBS, then filter sterilized through a 0.22 μm PES filter with a 30 cc luer-lock syringe, and 150 μL of the solution distributed into each well of a Nunc MaxiSorp (Product number: 439454) 96-well ELISA plate. The plates were covered with adhesive film, wrapped in aluminum foil, and incubated at 4° C. overnight.
2. On the day of assay, liraglutide mixtures were immobilized to BSA coated plate.
   a. Liraglutide was solubilized at 60 mg/mL in the drug composition buffer (14 mg/mL Propylene Glycol, 5.5 mg/mL Phenol, 1.42 mg/mL disodium phosphate dihydrate), pH adjusted to 8.15 using NaOH and/or HCl if needed, and filtered through a 0.22 μm PES filter. The solution was diluted to 6 mg/mL (1600 μM) liraglutide in PBS. This solution is referred to as "solution of soluble liraglutide".
   b. Liraglutide fibrils (hereafter: fibrils), obtained according to Assay (I) herein, resuspended in drug composition buffer at pH 8.15 (with concentration of fibrils determined by Assay (VII) (BCA assay) herein) in a sample of approx. 300 μL were sonicated on ice in a microcentrifuge tube (3 cycles of 10 s on/30 s off at 100% amplitude, FB-120 Sonic Dismembrator, Thermo Fisher Scientific). This solution is referred to as "solution of fibrils".
   c. The sonicated solution of fibrils was diluted into the solution of soluble liraglutide, such that the final concentration of fibril was 100 μM. The solution was then further serially diluted into solution of soluble liraglutide to resulting samples of 0.001, 0.0025, 0.01, 0.025, 0.1, 0.25, 1, 2.5, 10, and 25 μM fibril. Two controls were used: i) PBS (no peptide), and ii) no fibril (only solution of soluble liraglutide)
   d. The solutions obtained by diluting the solution of fibrils into the solution of soluble liraglutide were added (100 μL) to wells of BSA-coated ELISA plates and incubated for 3 hours at room temperature.
3. The remaining ELISA protocol was performed as described for Assay (VI) with some modifications.
   a. During this 3 hours, the antibody samples were spun in a centrifuge for 5 minutes at 21,000×g, and concentration of the supernatant measured by absorbance at 280 nm. Each antibody was serially diluted to 50 nM in PBS supplemented with 0.1% Tween20 (PBST).
   b. The plates were washed three times by addition of 300 μL PBS to each well.
   c. 100 μL of antibody solution was distributed into each well. The plates were then covered with adhesive film, wrapped in aluminum foil, and incubated for 1 hour at room temperature.
   d. The secondary antibody solution was prepared by diluting the secondary antibody (goat anti-human IgG-Fc HRP-conjugate, Invitrogen A18817, stock concentration: 0.5 mg/mL in 50% glycerol) 1:1000 into PBS supplemented with 0.1% Tween20 and 10 g/L BSA.
   e. The plates were washed three times by addition of 300 μL PBST to each well.
   f. 100 μL of secondary antibody solution was distributed into each well. The plates were then covered with adhesive film, wrapped in aluminum foil, and incubated for 1 hour at room temperature. During the secondary antibody incubation, 1-Step Ultra-TMB ELISA substrate (Thermo Fisher Scientific, 34208) was removed from the refrigerator to equilibrate the solution to room temperature and 2 M (4 N) H2SO4 was prepared.

g. The plates were washed three times by addition of 300 μL PBST to each well.
h. 100 μL Ultra-TMB was added into each well and incubated until yellow product was formed (5-10 minutes).
i. Reaction was quenched by addition of 100 μL 2 M H2SO4.
j. Absorbance of each well was read at 450 nm in microplate reader (BioTek Synergy Neo).
4. The residual samples (mixtures of fibrils and soluble liraglutide, as well as the PBS control and soluble liraglutide control from step 3) were incubated in microcentrifuge tubes at room temperature for 2.5 hours.
5. A Thioflavin T (ThT) stock solution was prepared at a concentration of 2200 μM. ThT was added to the samples (initially at total peptide concentration of 1600 μM) to a final concentration of 0.4 μM, and a 50 μL sample of the peptide/ThT mixtures was added to the wells of black 384-well plates (Fisherbrand 384 Well Polystyrene Plates, 12566624, Thermo Fisher Scientific). ThT fluorescence ($\lambda ex$=444 nm, $\lambda em$=482 nm) values were measured for each sample using a Biotek Synergy Neo microplate reader. The final (total) peptide concentration in the peptide/ThT mixture was 1571 μM (calculated prior to fibrillation).
6. The fluorescence measurements for the solutions comprising fibrils were divided by the fluorescence measurement for the solution of soluble liraglutide (no fibril control), and the ratio was reported as mixture/soluble ratio.

Assay (VII): BCA Assay

Concentration of fibrils (e.g. liraglutide fibrils) was determined using the Pierce BCA Protein Assay Kit (Thermo Fisher Scientific, 23225) with liraglutide as the standard for liraglutide fibrils and semaglutide as the standard for semaglutide fibrils (and not BSA). Since phenol from the drug composition buffer reacts with the BCA reagent to varying degree depending on sample dilution then controls were run for quantitation in order to account for background signal arising from phenol. Concentration of fibrils in the resuspended fibril solution from Assay (I) or Assay (II) herein was determined by subtracting the peptide concentration in the supernatant (after ultracentrifugation) from the initial concentration during fibril assembly (6 mg/mL). The analysis of liraglutide fibrils was carried out as described in the following:
1. Liraglutide was dissolved at 6 mg/mL (6000 μg/mL) in drug composition buffer, pH 8.15. This is referred to as "solution of soluble liraglutide".
2. For standards, solution of soluble liraglutide was diluted from (1) into PBS at the concentrations 2000, 1500, 1000, 750, 500, 250, 125, 25, and 0 μg/mL, and "blanks" that contained the same amount of drug composition buffer, pH 8.15 diluted in PBS (but lacking peptide) were prepared. For instance, to make 600 μL of the 2000 μg/mL standard would require 200 μL of the solution from (1) and 400 μL PBS. To make the blank, 200 μL of drug composition buffer (no peptide) and 400 μL of PBS was combined.
3. The supernatant from the ultra-centrifuged fibrils (in drug composition buffer, pH 8.15) obtained from Assay (I) herein was diluted into PBS at the following dilutions: 1:2, 1:4, 1:8, 1:16, 1:32. "Blanks" were also prepared for these samples that contained drug composition buffer, pH 8.15 diluted into PBS at the same dilutions.
4. To each well of a clear (no-binding or low-binding) flat-bottom 96-well plate, 10 μL of standard (and separate well with corresponding blanks) and 10 μL of diluted sample (and separate wells with corresponding blanks) was added.
5. The BCA Working reagent was made up and 225 μL added into each well and the plate covered with adhesive film.
6. The plate was incubated at 37° C. until purple color formation was adequate (this generally happens relatively quickly, and some color is often visible in some samples almost immediately).
7. Absorbance was read in a plate-reader at 562 nm.
8. The "blank" absorbance values for the standards were subtracted from the values for the standards. A standard curve was fitted to the resulting (background-subtracted) absorbances by plotting peptide concentration vs absorbance and fitting a $2^{nd}$ order polynomial.
9. The "blank" absorbance values for the supernatant were subtracted from the values for the supernatant dilutions. Using the standard curve from (8), the peptide concentration of the supernatant samples was determined and multiplied by their dilution factor to calculate the liraglutide concentration in the undiluted supernatant. Samples with calculated concentrations in the range from ~250-1000 μg/mL are preferred (this is the middle of the accurate range for the BCA assay).
10. Since the fibrils were assembled at a concentration of 6 mg/mL (6000 μg/mL), the peptide concentration of the supernatant was subtracted from this to obtain the concentration of fibril in the resuspended sample. It is important to resuspend the fibril pellets in Assay (I) in the exact same total volume after centrifugation for this calculation to be accurate.

Similar procedure may be used for semaglutide fibrils, except references to Assay (I) herein should be replaced by Assay (II) herein.

Results

Example 1: Antibodies

Antibodies (scFv-Fc) with amino acid sequences as listed in Table 1 were prepared by recombinant expression and purified.

Table 1 lists the full sequence of each antibody; bold text shows CDR locations (shown in the order L-CDR1, L-CDR2, L-CDR3, H-CDR1, H-CDR2, and H-CDR3); CDRs were defined according to the Kabat antibody numbering scheme. Table 2 lists the amino acid sequence of the variable region of the light chain ($V_L$ Sequence), the variable region of the heavy chain ($V_H$ Sequence) of the antibodies in Table 1. Table 3 lists the CDRs of the antibodies in Table 1.

TABLE 1

Antibody full sequence information

| Antibody | Full Sequence |
|---|---|
| A | DIQMTQSPSSLSASVGDRVTITCRASQGVSDAVSWYQQKPGKAPKLLIYSASFLYSGVPSRFSG SRSGTDFTLTISSLQPEDFATYYCQQHDTTPPTFGQGTKVEIKRTSPNSASHSGSAPQTSSAPG SQEVQLVESGGGLVQPGGSLRLSCAASGFNIKDTYIHWVRQAPGKGLEWVARISPTGGYTRYAA SVKGRFTISADTSKNTAYLQMNSLRAEDTAVYYCARDWFDAASFAWFDFYDYSDYWGQGTLVTV SSAAAHKTHTCPPCPAPELLGGPSVFLFPPKPKDTLMISRTPEVTCVVVDVSHEDPEVKFNWYV DGVEVHNAKTKPREEQYNSTYRVVSVLTVLHQDWLNGKEYKCKVSNKALPAPIEKTISKAKGQP REPQVYTLPPSRDELTKNQVSLTCLVKGFYPSDIAVEWESNGQPENNYKTTPPVLDSDGSFFLY SKLTVDKSRWQQGNVFSCSVMHEALHNHYTQKSLSLSPGKGSHHHHHHKLDYKDHDGDYKDHDI DYKDDDDK (SEQ ID NO: 1) |
| B | DIQMTQSPSSLSASVGDRVTITCRASQDVDSAVNWYQQKPGKAPKLLIYSASFLYSGVPSRFSG SRSGTDFTLTISSLQPEDFATYYCQQHCTYPPTFGQGTKVEIKRTSPNSASHSGSAPQTSSAPG SQEVQLVESGGGLVQPGGSLRLSCAASGFNIKDTYIHWVRQAPGKGLEWVARISPYDGNTRYAA SVKGRFTISADTSKNTAYLQMNSLRAEDTAVYYCARDWFDAASFAWFDFYDYSDYWGQGTLVTV SSAAAHKTHTCPPCPAPELLGGPSVFLFPPKPKDTLMISRTPEVTCVVVDVSHEDPEVKFNWYV DGVEVHNAKTKPREEQYNSTYRVVSVLTVLHQDWLNGKEYKCKVSNKALPAPIEKTISKAKGQP REPQVYTLPPSRDELTKNQVSLTCLVKGFYPSDIAVEWESNGQPENNYKTTPPVLDSDGSFFLY SKLTVDKSRWQQGNVFSCSVMHEALHNHYTQKSLSLSPGKGSHHHHHHKLDYKDHDGDYKDHDI DYKDDDDK (SEQ ID NO: 2) |
| C | DIQMTQSPSSLSASVGDRVTITCRASQDVSTAVTWYQQKPGKAPKLLIYSASFLYSGVPSRFSG SRSGTDFTLTISSLQPEDFATYYCQQHSTYPPTFGQGTKVEIKRTSPNSASHSGSAPQTSSAPG SQEVQLVESGGGLVQPGGSLRLSCAASGFNIKDTYIHWVRQAPGKGLEWVARISPAGGTTRYAA SVKGRFTISADTSKNTAYLQMNSLRAEDTAVYYCARDWFDAASFAWFDFYDYSDYWGQGTLVTV SSAAAHKTHTCPPCPAPELLGGPSVFLFPPKPKDTLMISRTPEVTCVVVDVSHEDPEVKFNWYV DGVEVHNAKTKPREEQYNSTYRVVSVLTVLHQDWLNGKEYKCKVSNKALPAPIEKTISKAKGQP REPQVYTLPPSRDELTKNQVSLTCLVKGFYPSDIAVEWESNGQPENNYKTTPPVLDSDGSFFLY SKLTVDKSRWQQGNVFSCSVMHEALHNHYTQKSLSLSPGKGSHHHHHHKLDYKDHDGDYKDHDI DYKDDDDK (SEQ ID NO: 3) |
| D | DIQMTQSPSSLSASVGDRVTITCRASQIVSNAVTWYQQKPGKAPKLLIYSASFLYSGVPSRFSG SRSGTDFTLTISSLQPEDFATYYCQQHCTTPPTFGQGTKVEIKRTSPNSASHSGSAPQTSSAPG SQEVQLVESGGGLVQPGGSLRLSCAASGFNIKDTYIHWVRQAPGKGLEWVARIYPDGGNTRYAG SVKGRFTISADTSKNTAYLQMNSLRAEDTAVYYCVRDWFDAASFANFDFYDYSDYWGQGTLVTV SSAAAHKTHTCPPCPAPELLGGPSVFLFPPKPKDTLMISRTPEVTCVVVDVSHEDPEVKFNWYV DGVEVHNAKTKPREEQYNSTYRVVSVLTVLHQDWLNGKEYKCKVSNKALPAPIEKTISKAKGQP REPQVYTLPPSRDELTKNQVSLTCLVKGFYPSDIAVEWESNGQPENNYKTTPPVLDSDGSFFLY SKLTVDKSRWQQGNVFSCSVMHEALHNHYTQKSLSLSPGKGSHHHHHHKLDYKDHDGDYKDHDI DYKDDDDK (SEQ ID NO: 4) |
| E | DIQMTQSPSSLSASVGDRVTITCRASQNVSDAVNWYQQKPGKAPKLLIYSASFLYSGVPSRFSG SRSGTDFTLTISSLQPEDFATYYCQQHYTNPPTFGQGTKVEIKRTSPNSASHSGSAPQTSSAPG SQEVQLVESGGGLVQPGGSLRLSCAASGFNIKDTYIHWVRQAPGKGLEWVARITPTDGTTRYAV SVKGRFTISADTSKNTAYLQMNSLRAEDTAVYYCAREWYEASYYDWFDYFDFSDYWGQGTLVTV SSAAAHKTHTCPPCPAPELLGGPSVFLFPPKPKDTLMISRTPEVTCVVVDVSHEDPEVKFNWYV DGVEVHNAKTKPREEQYNSTYRVVSVLTVLHQDWLNGKEYKCKVSNKALPAPIEKTISKAKGQP REPQVYTLPPSRDELTKNQVSLTCLVKGFYPSDIAVEWESNGQPENNYKTTPPVLDSDGSFFLY SKLTVDKSRWQQGNVFSCSVMHEALHNHYTQKSLSLSPGKGSHHHHHHKLDYKDHDGDYKDHDI DYKDDDDK (SEQ ID NO: 5) |
| F | DIQMTQSPSSLSASVGDRVTITCRASQIVNYAVYWYQQKPGKAPKLLIYSASFLYSGVPSRFSG SRSGTDFTLTISSLQPEDFVTYYCQQHYTTPPTFGQGTKVEIKRTSPNSASHSGSAPQTSSAPG SQEVQLVESGGGLVQPGGSLRLSCAASGENIKDTYIHWVRQAPGKGLEWVARIAPTNGTTRYAD SVKGRFTISADTSKNTAYLQMNSLRAEDTAVYYCAREWYEASYYDWFDYFDFSDYWGQGTLVTV SSAAAHKTHTCPPCPAPELLGGPSVFLFPPKPKDTLMISRTPEVTCVVVDVSHEDPEVKFNWYV DGVEVHNAKTKPREEQYNSTYRVVSVLTVLHQDWLNGKEYKCKVSNKALPAPIEKTISKAKGQP REPQVYTLPPSRDELTKNQVSLTCLVKGFYPSDIAVEWESNGQPENNYKTTPPVLDSDGSFFLY SKLTVDKSRWQQGNVFSCSVMHEALHNHYTQKSLSLSPGKGSHHHHHHKLDYKDHDGDYKDHDI DYKDDDDK (SEQ ID NO: 6) |
| G | DIQMTQSPSSLSASVGDRVTITCRASQGVTAAVAWYQQKPGKAPKLLIYSASFLYSGVPSRFSG SRSGTDFTLTISSLQPEDFATYYCQQHNTYPPTFGQGTKVEIKRTSPNSASHSGSAPQTSSAPG SQEVQLVESGGGLVQPGGSLRLSCAASGFNIKDTYIHWVRQAPGKGLEWVARIAPTSGYTRYAV SVKGRFTISADTSKNTAYLQMNSLRAEDTAVYYCAREWYEASYYDWFDYFDFSDYWGQGTLVTV SSAAAHKTHTCPPCPAPELLGGPSVFLFPPKPKDTLMISRTPEVTCVVVDVSHEDPEVKFNWYV DGVEVHNAKTKPREEQYNSTYRVVSVLTVLHQDWLNGKEYKCKVSNKALPAPIEKTISKAKGQP REPQVYTLPPSRDELTKNQVSLTCLVKGFYPSDIAVEWESNGQPENNYKTTPPVLDSDGSFFLY SKLTVDKSRWQQGNVFSCSVMHEALHNHYTQKSLSLSPGKGSHHHHHHKLDYKDHDGDYKDHDI DYKDDDDK (SEQ ID NO: 7) |
| H | DIQMTQSPSSLSASVGDRVTITCRASQDVNTAVAWYQQKPGKAPKLLIYSASFLYSGVPSRFSG SRSGTDFTLTISSLQPEDFATYYCQQHYTTPPTFGQGTKVEIKRTSPNSASHSGSAPQTSSAPG SQEVQLVESGGGLVQPGGSLRLSCAASGFNIKDTYIHWVRQAPGKGLEWVARIYPTNGYTRYAD SVKGRFTISADTSKNTAYLQMNSLRAEDTAVYYCAREVDTSYFFWFDYYDYDYWGQGTLVTV SSAAAHKTHTCPPCPAPELLGGPSVFLFPPKPKDTLMISRTPEVTCVVVDVSHEDPEVKFNWYV |

TABLE 1-continued

Antibody full sequence information

| Antibody | Full Sequence |
|---|---|
| | DGVEVHNAKTKPREEQYNSTYRVVSVLTVLHQDWLNGKEYKCKVSNKALPAPIEKTISKAKGQP<br>REPQVYTLPPSRDELTKNQVSLTCLVKGFYPSDIAVEWESNGQPENNYKTTPPVLDSDGSFFLY<br>SKLTVDKSRWQQGNVFSCSVMHEALHNHYTQKSLSLSPGKGSHHHHHHKLDYKDHDGDYKDHDI<br>DYKDDDDK (SEQ ID NO: 8) |
| I | DIQMTQSPSSLSASVGDRVTITCRASQDVNTAVAWYQQKPGKAPKLLIYSASFLYSGVPSRFSG<br>SRSGTDFTLTISSLQPEDFATYYCQQHYTTPPTFGQGTKVEIKRTSPNSASHSGSAPQTSSAPG<br>SQEVQLVESGGGLVQPGGSLRLSCAASGFNIKDTYIHWVRQAPGKGLEWVARIYPTNGYTRYAD<br>SVKGRFTISADTSKNTAYLQMNSLRAEDTAVYYCARDWFDAASFAWFDFYDYSDYWGQGTLVTV<br>SSAAAHKTHTCPPCPAPELLGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKALPAPIEKTISKAKGQP<br>REPQVYTLPPSRDELTKNQVSLTCLVKGFYPSDIAVEWESNGQPENNYKTTPPVLDSDGSFFLY<br>SKLTVDKSRWQQGNVFSCSVMHEALHNHYTQKSLSLSPGKGSHHHHHHKLDYKDHDGDYKDHDI<br>DYKDDDDK (SEQ ID NO: 9) |
| J | DIQMTQSPSSLSASVGDRVTITCRASQDVNTAVAWYQQKPGKAPKLLIYSASFLYSGVPSRFSG<br>SRSGTDFTLTISSLQPEDFATYYCQQHYTTPPTFGQGTKVEIKRTSPNSASHSGSAPQTSSAPG<br>SQEVQLVESGGGLVQPGGSLRLSCAASGFNIKDTYIHWVRQAPGKGLEWVARIYPTNGYTRYAD<br>SVKGRFTISADTSKNTAYLQMNSLRAEDTAVYYCAREWYEASYYDWFDYFDFSDYWGQGTLVTV<br>SSAAAHKTHTCPPCPAPELLGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKALPAPIEKTISKAKGQP<br>REPQVYTLPPSRDELTKNQVSLTCLVKGFYPSDIAVEWESNGQPENNYKTTPPVLDSDGSFFLY<br>SKLTVDKSRWQQGNVESCSVMHEALHNHYTQKSLSLSPGKGSHHHHHHKLDYKDHDGDYKDHDI<br>DYKDDDDK (SEQ ID NO: 10) |
| K | DIQMTQSPSSLSASVGDRVTITCRASQDVNTAVAWYQQKPGKAPKLLIYSASFLYSGVPSRFSG<br>SRSGTDFTLTISSLQPEDFATYYCQQHYTTPPTFGQGTKVEIKRTSPNSASHSGSAPQTSSAPG<br>SQEVQLVESGGGLVQPGGSLRLSCAASGFNIKDTYIHWVRQAPGKGLEWVARIYPTNGYTRYAD<br>SVKGRFTISADTSKNTAYLQMNSLRAEDTAVYYCAREWSDATYFYWFDFYDSDYWGQGTLVTV<br>SSAAAHKTHTCPPCPAPELLGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKALPAPIEKTISKAKGQP<br>REPQVYTLPPSRDELTKNQVSLTCLVKGFYPSDIAVEWESNGQPENNYKTTPPVLDSDGSFFLY<br>SKLTVDKSRWQQGNVESCSVMHEALHNHYTQKSLSLSPGKGSHHHHHHKLDYKDHDGDYKDHDI<br>DYKDDDDK (SEQ ID NO: 11) |
| L | DIQMTQSPSSLSASVGDRVTITCRASQDVNTAVAWYQQKPGKAPKLLIYSASFLYSGVPSRFSG<br>SRSGTDFTLTISSLQPEDFATYYCQQHYTTPPTFGQGTKVEIKRTSPNSASHSGSAPQTSSAPG<br>SQEVQLVESGGGLVQPGGSLRLSCAASGENIKDTYIHWVRQAPGKGLEWVARIYPTNGYTRYAD<br>SVKGRFTISADTSKNTAYLQMNSLRAEDTAVYYCARELFDSSYFSWFDFYYDYDYWGQGTLVTV<br>SSAAAHKTHTCPPCPAPELLGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKALPAPIEKTISKAKGQP<br>REPQVYTLPPSRDELTKNQVSLTCLVKGFYPSDIAVEWESNGQPENNYKTTPPVLDSDGSFFLY<br>SKLTVDKSRWQQGNVESCSVMHEALHNHYTQKSLSLSPGKGSHHHHHHKLDYKDHDGDYKDHDI<br>DYKDDDDK (SEQ ID NO: 12) |
| M | DIQMTQSPSSLSASVGDRVTITCRASQSVAAAVAWYQQKPDKAPKLLIYSASFLYSGVPSRFSG<br>SRSGTDFTLTISSLQPEDFATYYCQQHNTYPPTFGQGTKVEIKRTSPNSASHSGSAPQTSSAPG<br>SQEVQLVESGGGLVQPGGSLRLSCAASGFNIKDTYIHWVRQAPGKGLEWVARISPSSGSTRYAG<br>SVKGRFTISADTSKNTAYLQMNSLRAEDTAVYYCAREWYEASYYDWFDYFDFSDYWGQGTLVTV<br>SSAAAHKTHTCPPCPAPELLGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKALPAPIEKTISKAKGQP<br>REPQVYTLPPSRDELTKNQVSLTCLVKGFYPSDIAVEWESNGQPENNYKTTPPVLDSDGSFFLY<br>SKLTVDKSRWQQGNVFSCSVMHEALHNHYTQKSLSLSPGKGSHHHHHHKLDYKDHDGDYKDHDI<br>DYKDDDDK (SEQ ID NO: 109) |
| N | DIQMTQSPSSLSASVGDRVTITCRASQSVDYAVSWYQQKPGKAPKLLIYSASFLYSGVPSRFSG<br>SRSGTDFTLTISSLQPEDFATYYCQQHNTTPPTFGQGTKVEIKRTSPNSASHSGSAPQTSSAPG<br>SQEVQLVESGGGLVQPGGSLRLSCAASGFNIKDTYIHWVRQAPGKGLEWVARIAPDNGTTRYAV<br>SVKGRFTISADTSKNTAYLQMNSLRAEDTAVYYCAREWYEASYYDWFDYFDFSDYWGQGTLVTV<br>SSAAAHKTHTCPPCPAPELLGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKALPAPIEKTISKAKGQP<br>REPQVYTLPPSRDELTKNQVSLTCLVKGFYPSDIAVEWESNGQPENNYKTTPPVLDSDGSFFLY<br>SKLTVDKSRWQQGNVFSCSVMHEALHNHYTQKSLSLSPGKGSHHHHHHKLDYKDHDGDYKDHDI<br>DYKDDDDK (SEQ ID NO: 110) |

TABLE 2

Antibody variable light chain (V_L) and variable heavy chain (V_H) amino acid sequence

| Antibody | V_L Sequence | V_H Sequence |
|---|---|---|
| A | DIQMTQSPSSLSASVGDRVTITCRASQGVSDAVSWYQQKPGKAPKLLIYSASFLYSGVPSRFSGSRSGTDFTLTISSLQPEDFATYYCQQHDTTPPTFGQGTKVEIK (SEQ ID NO: 13) | EVQLVESGGGLVQPGGSLRLSCAASGFNIKDTYIHWVRQAPGKGLEWVARISPTGYTRYAASVKGRFTISADTSKNTAYLQMNSLRAEDTAVYYCARDWFDAASFAWFDFYDYSDYWGQGTLVTVSS (SEQ ID NO: 14) |
| B | DIQMTQSPSSLSASVGDRVTITCRASQDVDSAVNWYQQKPGKAPKLLIYSASFLYSGVPSRFSGSRSGTDFTLTISSLQPEDFATYYCQQHCTYPPTFGQGTKVEIK (SEQ ID NO: 15) | EVQLVESGGGLVQPGGSLRLSCAASGFNIKDTYIHWVRQAPGKGLEWVARISPYDGNTRYAASVKGRFTISADTSKNTAYLQMNSLRAEDTAVYYCARDWFDAASFAWFDFYDYSDYWGQGTLVTVSS (SEQ ID NO: 16) |
| C | DIQMTQSPSSLSASVGDRVTITCRASQDVSTAVTWYQQKPGKAPKLLIYSASFLYSGVPSRFSGSRSGTDFTLTISSLQPEDFATYYCQQHSTYPPTFGQGTKVEIK (SEQ ID NO: 17) | EVQLVESGGGLVQPGGSLRLSCAASGFNIKDTYIHWVRQAPGKGLEWVARISPAGGTTRYAASVKGRFTISADTSKNTAYLQMNSLRAEDTAVYYCARDWFDAASFAWFDFYDYSDYWGQGTLVTVSS (SEQ ID NO: 18) |
| D | DIQMTQSPSSLSASVGDRVTITCRASQIVSNAVTWYQQKPGKAPKLLIYSASFLYSGVPSRFSGSRSGTDFTLTISSLQPEDFATYYCQQHCTTPPTFGQGTKVEIK (SEQ ID NO: 19) | EVQLVESGGGLVQPGGSLRLSCAASGFNIKDTYIHWVRQAPGKGLEWVARIYPDGGNTRYAGSVKGRFTISADTSKNTAYLQMNSLRAEDTAVYYCVRDWFDAASFAWFDFYDYSDYWGQGTLVTVSS (SEQ ID NO: 20) |
| E | DIQMTQSPSSLSASVGDRVTITCRASQNVSDAVNWYQQKPGKAPKLLIYSASFLYSGVPSRFSGSRSGTDFTLTISSLQPEDFATYYCQQHYTNPPTFGQGTKVEIK (SEQ ID NO: 21) | EVQLVESGGGLVQPGGSLRLSCAASGFNIKDTYIHWVRQAPGKGLEWVARITPTDGTTRYAVSVKGRFTISADTSKNTAYLQMNSLRAEDTAVYYCAREWYEASYYDWFDYFDFSDYWGQGTLVTVSS (SEQ ID NO: 22) |
| F | DIQMTQSPSSLSASVGDRVTITCRASQIVNYAVYWYQQKPGKAPKLLIYSASFLYSGVPSRFSGSRSGTDFTLTISSLQPEDFVTYYCQQHYTTPPTFGQGTKVEIK (SEQ ID NO: 23) | EVQLVESGGGLVQPGGSLRLSCAASGFNIKDTYIHWVRQAPGKGLEWVARIAPTNGTTRYADSVKGRFTISADTSKNTAYLQMNSLRAEDTAVYYCAREWYEASYYDWFDYFDFSDYWGQGTLVTVSS (SEQ ID NO: 24) |
| G | DIQMTQSPSSLSASVGDRVTITCRASQGVTAAVAWYQQKPGKAPKLLIYSASFLYSGVPSRFSGSRSGTDFTLTISSLQPEDFATYYCQQHNTYPPTFGQGTKVEIK (SEQ ID NO: 25) | EVQLVESGGGLVQPGGSLRLSCAASGFNIKDTYIHWVRQAPGKGLEWVARIAPTSGYTRYAVSVKGRFTISADTSKNTAYLQMNSLRAEDTAVYYCAREWYEASYYDWFDYFDFSDYWGQGTLVTVSS (SEQ ID NO: 26) |
| H | DIQMTQSPSSLSASVGDRVTITCRASQDVNTAVAWYQQKPGKAPKLLIYSASFLYSGVPSRFSGSRSGTDFTLTISSLQPEDFATYYCQQHYTTPPTFGQGTKVEIK (SEQ ID NO: 27) | EVQLVESGGGLVQPGGSLRLSCAASGFNIKDTYIHWVRQAPGKGLEWVARIYPTNGYTRYADSVKGRFTISADTSKNTAYLQMNSLRAEDTAVYYCAREVYDTSYFFWFDYYDYDYWGQGTLVTVSS (SEQ ID NO: 28) |
| I | DIQMTQSPSSLSASVGDRVTITCRASQDVNTAVAWYQQKPGKAPKLLIYSASFLYSGVPSRFSGSRSGTDFTLTISSLQPEDFATYYCQQHYTTPPTFGQGTKVEIK (SEQ ID NO: 29) | EVQLVESGGGLVQPGGSLRLSCAASGFNIKDTYIHWVRQAPGKGLEWVARIYPTNGYTRYADSVKGRFTISADTSKNTAYLQMNSLRAEDTAVYYCARDWFDAASFAWFDFYDYSDYWGQGTLVTVSS (SEQ ID NO: 30) |
| J | DIQMTQSPSSLSASVGDRVTITCRASQDVNTAVAWYQQKPGKAPKLLIYSASFLYSGVPSRFSGSRSGTDFTLTISSLQPEDFATYYCQQHYTTPPTFGQGTKVEIK (SEQ ID NO: 31) | EVQLVESGGGLVQPGGSLRLSCAASGFNIKDTYIHWVRQAPGKGLEWVARIYPTNGYTRYADSVKGRFTISADTSKNTAYLQMNSLRAEDTAVYYCAREWYEASYYDWFDYFDFSDYWGQGTLVTVSS (SEQ ID NO: 32) |
| K | DIQMTQSPSSLSASVGDRVTITCRASQDVNTAVAWYQQKPGKAPKLLIYSASFLYSGVPSRFSGSRSGTDFTLTISSLQPEDFATYYCQQHYTTPPTFGQGTKVEIK (SEQ ID NO: 33) | EVQLVESGGGLVQPGGSLRLSCAASGFNIKDTYIHWVRQAPGKGLEWVARIYPTNGYTRYADSVKGRFTISADTSKNTAYLQMNSLRAEDTAVYYCAREWSDATYFYWFDFYDYSDYWGQGTLVTVSS (SEQ ID NO: 34) |
| L | DIQMTQSPSSLSASVGDRVTITCRASQDVNTAVAWYQQKPGKAPKLLIYSASFLYSGVPSRFSGSRSGTDFTLTISSLQPEDFATYYCQQHYTTPPTFGQGTKVEIK (SEQ ID NO: 35) | EVQLVESGGGLVQPGGSLRLSCAASGFNIKDTYIHWVRQAPGKGLEWVARIYPTNGYTRYADSVKGRFTISADTSKNTAYLQMNSLRAEDTAVYYCARELFDSSYFSWFDFYDYYDYWGQGTLVTVSS (SEQ ID NO: 36) |
| M | DIQMTQSPSSLSASVGDRVTITCRASQSVAAAVAWYQQKPDKAPKLLIYSASFLYSGVPSRF | EVQLVESGGGLVQPGGSLRLSCAASGFNIKDTYIHWVRQAPGKGLEWVARISPSSGSTRYAG |

TABLE 2-continued

Antibody variable light chain (V_L) and variable heavy chain (V_H) amino acid sequence

| Antibody | V_L Sequence | V_H Sequence |
|---|---|---|
|  | SGSRSGTDFTLTISSLQPEDFATYYCQQHNT YPPTFGQGTKVEIK (SEQ ID NO: 111) | SVKGRFTISADTSKNTAYLQMNSLRAEDTAV YYCAREWYEASYYDWFDYFDFSDYWGQGTLV TVSS (SEQ ID NO: 112) |
| N | DIQMTQSPSSLSASVGDRVTITCRASQSVDY AVSWYQQKPGKAPKLLIYSASFLYSGVPSRF SGSRSGTDFTLTISSLQPEDFATYYCQQHNT TPPTFGQGTKVEIK (SEQ ID NO: 113) | EVQLVESGGGLVQPGGSLRLSCAASGFNIKD TYIHWVRQAPGKGLEWVARIAPDNGTTRYAV SVKGRFTISADTSKNTAYLQMNSLRAEDTAV YYCAREWYEASYYDWFDYFDFSDYWGQGTLV TVSS (SEQ ID NO: 114) |

TABLE 3

Antibody CDR sequences

| Antibody | H-CDR3 | H-CDR2 | H-CDR1 | L-CDR3 | L-CDR2 | L-CDR1 |
|---|---|---|---|---|---|---|
| A | DWFDAASFAW FDFYDYSDY (SEQ ID NO: 37) | RISPTGGYTR YAASVKG (SEQ ID NO: 38) | DTYIH (SEQ ID NO: 39) | QQHDTTPPT (SEQ ID NO: 40) | SASFLYS (SEQ ID NO: 41) | RASQGVSDAV S (SEQ ID NO: 42) |
| B | DWFDAASFAW FDFYDYSDY (SEQ ID NO: 43) | RISPYDGNTR YAASVKG (SEQ ID NO: 44) | DTYIH (SEQ ID NO: 45) | QQHCTYPPT (SEQ ID NO: 46) | SASFLYS (SEQ ID NO: 47) | RASQDVDSAV N (SEQ ID NO: 48) |
| C | DWFDAASFAW FDFYDYSDY (SEQ ID NO: 49) | RISPAGGTTR YAASVKG (SEQ ID NO: 50) | DTYIH (SEQ ID NO: 51) | QQHSTYPPT (SEQ ID NO: 52) | SASFLYS (SEQ ID NO: 53) | RASQDVSTAV T (SEQ ID NO: 54) |
| D | DWFDAASFAW FDFYDYSDY (SEQ ID NO: 55) | RIYPDGGNTR YAGSVKG (SEQ ID NO: 56) | DTYIH (SEQ ID NO: 57) | QQHCTTPPT (SEQ ID NO: 58) | SASFLYS (SEQ ID NO: 59) | RASQIVSNAV T (SEQ ID NO: 60) |
| E | EWYEASYYDW FDYFDFSDY (SEQ ID NO: 61) | RITPTDGTTR YAVSVKG (SEQ ID NO: 62) | DTYIH (SEQ ID NO: 63) | QQHYTNPPT (SEQ ID NO: 64) | SASFLYS (SEQ ID NO: 65) | RASQNVSDAV N (SEQ ID NO: 66) |
| F | EWYEASYYDW FDYFDFSDY (SEQ ID NO: 67) | RIAPTNGTTR YADSVKG (SEQ ID NO: 68) | DTYIH (SEQ ID NO: 69) | QQHYTTPPT (SEQ ID NO: 70) | SASFLYS (SEQ ID NO: 71) | RASQIVNYAV Y (SEQ ID NO: 72) |
| G | EWYEASYYDW FDYFDFSDY (SEQ ID NO: 73) | RIAPTSGYTR YAVSVKG (SEQ ID NO: 74) | DTYIH (SEQ ID NO: 75) | QQHNTYPPT (SEQ ID NO: 76) | SASFLYS (SEQ ID NO: 77) | RASQGVTAAV A (SEQ ID NO: 78) |
| H | EVYDTSYFFW FDYYDYYDY (SEQ ID NO: 79) | RIYPTNGYTR YADSVK (SEQ ID NO: 80) | DTYIH (SEQ ID NO: 81) | QQHYTTPPT (SEQ ID NO: 82) | SASFLYS (SEQ ID NO: 83) | RASQDVNTAV A (SEQ ID NO: 84) |
| I | DWFDAASFAW FDFYDYSDY (SEQ ID NO: 85) | RIYPTNGYTR YADSVKG (SEQ ID NO: 86) | DTYIH (SEQ ID NO: 87) | QQHYTTPPT (SEQ ID NO: 88) | SASFLYS (SEQ ID NO: 89) | RASQDVNTAV A (SEQ ID NO: 90) |
| J | EWYEASYYDW FDYFDFSDY (SEQ ID NO: 91) | RIYPTNGYTR YADSVKG (SEQ ID NO: 92) | DTYIH (SEQ ID NO: 93) | QQHYTTPPT (SEQ ID NO: 94) | SASFLYS (SEQ ID NO: 95) | RASQDVNTAV A (SEQ ID NO: 96) |
| K | EWSDATYFYW FDFYDYSDY (SEQ ID NO: 97) | RIYPTNGYTR YADSVKG (SEQ ID NO: 98) | DTYIH (SEQ ID NO: 99) | QQHYTTPPT (SEQ ID NO: 100) | SASFLYS (SEQ ID NO: 101) | RASQDVNTAV A (SEQ ID NO: 102) |

TABLE 3-continued

Antibody CDR sequences

| Antibody | H-CDR3 | H-CDR2 | H-CDR1 | L-CDR3 | L-CDR2 | L-CDR1 |
|---|---|---|---|---|---|---|
| L | ELFDSSYFSW FDFYDYYDY (SEQ ID NO: 103) | RIYPTNGYTR YADSVKG (SEQ ID NO: 104) | DTYIH (SEQ ID NO: 105) | QQHYTTPPT (SEQ ID NO: 106) | SASFLYS (SEQ ID NO: 107) | RASQDVNTAV A (SEQ ID NO: 108) |
| M | EWYEASYYDW FDYFDFSDY (SEQ ID NO: 115) | RISPSSGSTR YAGSVKG (SEQ ID NO: 116) | DTYIH (SEQ ID NO: 117) | QQHNTYPPT (SEQ ID NO: 118) | SASFLYS (SEQ ID NO: 119) | RASQSVAAAV A (SEQ ID NO: 120) |
| N | EWYEASYYDW FDYFDFSDY (SEQ ID NO: 121) | RIAPDNGTTR YAVSVKG (SEQ ID NO: 122) | DTYIH (SEQ ID NO: 123) | QQHNTTPPT (SEQ ID NO: 124) | SASFLYS (SEQ ID NO: 125) | RASQSVDYAV S (SEQ ID NO: 126) |

Example 2: Liraglutide Fibril Specificity of Antibodies

Antibodies of Example 1 were individually tested for their ability to bind to liraglutide fibrils compared to background and/or soluble liraglutide. Test were carried out according to Assay (III) or Assay (IV) as defined herein. The results are shown in Tables 4 and 5.

TABLE 4

Liraglutide fibril specificity of antibodies determined according to Assay (III) described herein using 25 µM liraglutide fibril concentration

| Antibody | Antibody Specificity Ratio | |
|---|---|---|
| | Liraglutide fibril/ Background | Liraglutide fibril/ Soluble liraglutide |
| H | 25.3 | 31.7 |
| I | 23.6 | 26.8 |
| J | 17.1 | 22.8 |
| K | 16.1 | 24.0 |
| L | 16.6 | 25.2 |

TABLE 5

Liraglutide fibril specificity of antibodies determined in a mixture with soluble liraglutide according to Assay (IV) described herein using 0.1 µM liraglutide fibril concentration

| Antibody | Antibody Specificity Ratio (Liraglutide fibril in mixture/Soluble liraglutide) |
|---|---|
| A | 8.44 |
| B | 21.5 |
| C | 24.3 |
| D | 30.7 |
| E | 37.1 |
| F | 40.4 |
| G | 35.8 |
| I | 4.03 |
| J | 2.77 |

Results in Table 4 and 5 show that the antibodies tested bind liraglutide fibrils significantly more than soluble liraglutide. Results in Table 4 also shows that the antibodies tested bind liraglutide fibrils significantly more than background. Results in Table 5 shows that the antibodies tested are also able to bind liraglutide fibrils significantly more when tested in a mixture of high concentrations of soluble liraglutide.

Example 3: Sensitivity for Detection of Liraglutide Fibrils—Antibodies Compared to ThT Assay The ThT assay was tested for its ability to bind to liraglutide fibrils in a mixture with excess of soluble liraglutide in order to allow a comparison of sensitivity with the antibodies of the invention. The experiment was carried out according to Assay (VI) herein. Results are shown in Table 6.

TABLE 6

Sensitivity for detection of liraglutide fibrils; results reported as Specificity Ratio (liraglutide fibril in mixture/soluble liraglutide).

| Liraglutide fibril concentration (µM) | Detection method | | |
|---|---|---|---|
| | ThT | Antibody I | Antibody J |
| 0.001 | 1.03 | 1.03 | 1.08 |
| 0.0025 | 1.02 | 1.29 | 1.41 |
| 0.01 | 0.992 | 1.47 | 2.52 |
| 0.025 | 0.996 | 2.80 | 3.08 |
| 0.1 | 1.02 | 5.36 | 4.94 |
| 0.25 | 1.07 | 9.15 | 7.64 |
| 1 | 1.19 | 13.5 | 11.1 |
| 2.5 | 1.44 | 15.9 | 13.3 |
| 10 | 2.55 | 24.6 | >40 |
| 25 | 4.96 | >40 | >40 |

">40" indicates that the result was higher than what could be quantified

Example 4: Concentration-Dependent Binding Analysis of Liraglutide Antibodies

Antibodies were prepared as described in section "Antibody expression and purification". Antibodies E, M and N were two-step purified at yields >20 mg/L. The purified antibodies were predominantly monomeric, as demonstrated by analytical size-exclusion chromatography (>95% monomer for E, M and N; FIG. 1). The sensitivity of the assay using the two-step purified antibodies (>95% monomer) was also enhanced by removal of BSA during the primary antibody incubation. These changes resulted in improved Assay (III-B).

Antibodies E, M and N of Example 1 were two-step purified (>95% monomer) and individually tested for their ability to bind to liraglutide fibrils compared to background and/or soluble liraglutide. Test were carried out according to Assay (III-B) herein. The results are shown in Table 7 (raw (non-background subtracted) antibody binding signals for aggregated and soluble liraglutide) and Table 8 (Liraglutide fibril specificity of antibodies (Liraglutide fibril/Monomer liraglutide)). Three independent experiments were performed, and the reported values are averages.

TABLE 7

Antibody binding signals for aggregated and soluble liraglutide for two-step purified antibodies.

| Liraglutide fibril concentration (µM) | Antibody (Monomer or fibril) | | | | | |
| --- | --- | --- | --- | --- | --- | --- |
| | E (monomer) | M (monomer) | N (monomer) | E (fibril) | M (fibril) | N (fibril) |
| 0.01 | 0.05 | 0.05 | 0.05 | 0.06 | 0.06 | 0.06 |
| 0.03 | 0.05 | 0.04 | 0.05 | 0.07 | 0.07 | 0.06 |
| 0.10 | 0.05 | 0.04 | 0.05 | 0.07 | 0.07 | 0.06 |
| 0.30 | 0.05 | 0.05 | 0.05 | 0.07 | 0.09 | 0.07 |
| 1 | 0.05 | 0.05 | 0.05 | 0.10 | 0.15 | 0.08 |
| 3 | 0.05 | 0.05 | 0.05 | 0.16 | 0.30 | 0.09 |
| 10 | 0.08 | 0.06 | 0.05 | 0.34 | 0.73 | 0.15 |
| 30 | 0.15 | 0.10 | 0.05 | 0.84 | 1.69 | 0.29 |
| 100 | 0.32 | 0.21 | 0.06 | 2.08 | 2.78 | 0.63 |
| 300 | 0.51 | 0.46 | 0.09 | 3.05 | 3.15 | 1.87 |

TABLE 8

Liraglutide fibril specificity of antibodies (Liraglutide fibril/Liraglutide monomer) for two-step purified antibodies.

| Liraglutide fibril concentration (µM) | Antibody | | |
| --- | --- | --- | --- |
| | E | M | N |
| 0.01 | 1.30 | 1.39 | 1.41 |
| 0.03 | 1.40 | 1.58 | 1.32 |
| 0.1 | 1.51 | 1.61 | 1.31 |
| 0.3 | 1.62 | 1.90 | 1.47 |
| 1 | 2.01 | 3.21 | 1.62 |
| 3 | 3.04 | 5.90 | 1.86 |
| 10 | 4.35 | 11.69 | 3.01 |
| 30 | 5.59 | 16.34 | 5.57 |
| 100 | 6.60 | 13.05 | 10.04 |
| 300 | 5.93 | 6.81 | 21.09 |

Results in Table 7 and 8 show that the antibodies tested bind liraglutide fibrils significantly more than soluble liraglutide.

It was also observed that using highly purified antibodies (>95% monomer) in the assay has the advantage of making Assay (III-B) more reproducible than previous Assay (III) that used one-step purified antibody (>5% antibody aggregate) because it is easier to control the amount of antibody aggregate in different batches of two-step purified antibody (>95% monomer). The removal of antibody aggregates using size-exclusion chromatography reduced the antibody sensitivity at low antibody concentrations because antibody aggregates contributed to binding to liraglutide fibrils. However, the increased antibody purity enabled the use of higher antibody concentrations due to lower background signal, which enabled improved assay sensitivity.

Example 5: Sensitivity for Detection of Liraglutide Fibrils—Antibodies Compared to ThT Assay Antibodies were prepared as described in section "Antibody expression and purification". Antibodies E, M and N were two-step purified at yields >20 mg/L. The purified antibodies were predominantly monomeric, as demonstrated by analytical size-exclusion chromatography (>95% monomer for E, M and N; FIG. 1). The sensitivity of the assay using the two-step purified antibodies (>95% monomer) was also enhanced by removal of BSA during the primary antibody incubation and increase of the antibody concentration (from 5 to 50 nM), resulting in improved Assay (VI-B).

The ThT assay was tested for its ability to bind to liraglutide fibrils in a mixture with excess of soluble liraglutide in order to allow a comparison of sensitivity with the antibody M of the invention. The experiment was carried out according to Assay (VI-B) herein. Results are shown in Table 9.

TABLE 9

Sensitivity for detection of liraglutide fibrils for two-step purified antibody M (>95% monomer) using Assay (VI-B); results reported as Specificity Ratio (liraglutide fibril in mixture/soluble liraglutide), ThT concentration = 0.4 µM.

| Liraglutide fibril concentration (µM) | Detection method | |
| --- | --- | --- |
| | ThT | Antibody M |
| 0.001 | 1.08 | 1.43 |
| 0.0025 | 1.07 | 2.45 |
| 0.010 | 1.14 | 6.81 |
| 0.025 | 1.26 | 14.39 |
| 0.100 | 2.00 | 32.07 |
| 0.250 | 3.54 | 40.76 |
| 1.000 | 11.9 | 46.62 |
| 2.500 | 27.7 | 48.28 |

Results in Table 9 show that sensitivity of antibodies of the invention for detecting liraglutide fibrils are several magnitudes greater than the ThT Assay. In addition, it was also found that antibodies of the invention detected liraglutide fibrils at concentrations of the fibrils where no signal was registered in the ThT Assay.

It was also observed that using highly purified antibodies (>95% monomer) in the assay has the advantage of making Assay (VI-B) more reproducible than previous Assay (VI) that used one-step purified antibody (>5% antibody aggregate) because it is easier to control the amount of antibody aggregate in different batches of two-step purified antibody (>95% monomer). The removal of antibody aggregates using size-exclusion chromatography reduced the antibody sensitivity at low antibody concentrations (e.g., 5 nM) because antibody aggregates contributed to binding to liraglutide fibrils. However, the increased antibody purity enabled the use of higher antibody concentrations (50 nM instead of 5 nM) due to lower background signal, which enabled improved assay sensitivity.

Example 6: Reproducibility for Antibodies Having Purity of >95% Monomer

Antibody M of Example 1 were two-step purified (>95% monomer) and tested for its ability to bind to liraglutide fibrils in the presence of excess soluble liraglutide compared to soluble liraglutide. Tests were carried out according to Assay (VI-B) herein. Two different batches of antibody were tested and a total of four independent experiments were performed. The results are shown in Table 10.

TABLE 10

Sensitivity for detection of liraglutide fibrils for double-sorted antibody M using Assay (VI-B); results reported as Specificity Ratio (liraglutide fibril in mixture/soluble liraglutide), ThT concentration = 0.4 μM.

| Liraglutide fibril concentration (μM) | M, 1st batch, 1st exp | M, 1st batch, 2nd exp | M, 1st batch, 3rd exp | M, 2nd batch, 4th exp | Average |
|---|---|---|---|---|---|
| 0.001 | 1.75 | 1.26 | 1.40 | 1.33 | 1.43 |
| 0.0025 | 3.53 | 1.66 | 2.16 | 2.45 | 2.45 |
| 0.01 | 9.61 | 5.23 | 5.74 | 6.65 | 6.81 |
| 0.025 | 18.23 | 13.70 | 12.83 | 12.79 | 14.39 |
| 0.1 | 34.82 | 31.40 | 31.61 | 30.46 | 32.07 |
| 0.25 | 44.77 | 39.44 | 39.51 | 39.33 | 40.76 |
| 1 | 47.72 | 47.99 | 45.49 | 45.26 | 46.62 |
| 2.5 | 50.37 | 50.36 | 46.59 | 45.79 | 48.28 |
| 10 | 50.82 | 53.28 | 46.53 | 44.13 | 48.69 |
| 25 | 47.45 | 52.52 | 44.45 | 42.12 | 46.64 |

Results in Table 10 show that using highly purified antibodies (>95% monomer) in the assay leads to very reproducible results.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. An antibody of SEQ ID NO: 5, or an antigen-binding fragment thereof, comprising:
a heavy chain variable region comprising a CDR1, a CDR2, and a CDR3 sequence (H-CDR1, H-CDR2 and H-CDR3) and a light chain variable region of said antibody comprises a CDR1, a CDR2, and a CDR3 sequence (L-CDR1, L-CDR2 and L-CDR3) that is:
SEQ ID NO: 63, 62, and 61 (H-CDR1, H-CDR2, and H-CDR3) and SEQ ID NO: 66, 65, and 64 (L-CDR1, L-CDR2, and L-CDR3);
m. and
wherein the antibody binds liraglutide fibrils.

2. An antibody, or an antigen-binding fragment thereof, wherein said antibody comprises a sequence of SEQ ID NO: 110, wherein the variable region of the heavy chain of said antibody comprises a CDR1, a CDR2, and a CDR3 sequence consisting of: SEQ ID NO: 123, 122, and 121 (H-CDR1, H-CDR2, and H-CDR3) and the variable region of the light chain of said antibody comprises a CDR1, a CDR2, and a CDR3 sequence consisting of: SEQ ID NO: 126, 125, and 124 (L-CDR1, L-CDR2, and L-CDR3), wherein the antibody binds liraglutide fibrils.

3. An assay for selectively detecting liraglutide fibrils over soluble and/or monomeric liraglutide comprising an antibody, or an antigen-binding fragment thereof, as defined in claim 1, wherein said assay can sensitively detect liraglutide aggregates at low concentrations such as 1-10 ppm fibrils, alternatively 10-100 ppm fibrils, alternatively 100-1000 ppm fibrils.

4. An assay for selectively detecting liraglutide fibrils over soluble and/or monomeric liraglutide comprising an antibody, or an antigen-binding fragment thereof, as defined in claim 2, wherein said assay can sensitively detect liraglutide aggregates at low concentrations such as 1-10 ppm fibrils, alternatively 10-100 ppm fibrils, alternatively 100-1000 ppm fibrils.

5. The antibody, or an antigen-binding fragment thereof, according to claim 1, wherein said antibody comprises a sequence of SEQ ID NO: 5 having about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity.

6. The antibody, or an antigen-binding fragment thereof, according to claim 2, wherein said antibody comprises a sequence of SEQ ID NO: 110 having about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity.

7. Method for identifying and/or quantifying liraglutide fibrils, said method comprising the steps of
   a) binding the antibody, or an antigen-binding fragment thereof, as defined in claim 1 to liraglutide;
   b) optionally detecting antibody bound to liraglutide fibrils;
   c) optionally quantifying antibody bound to liraglutide fibrils, optionally by use of a standard of said fibril.

8. Method for identifying and/or quantifying liraglutide fibrils, said method comprising the steps of
   a) binding the antibody, or an antigen-binding fragment thereof, as defined in claim 2 to liraglutide;
   b) optionally detecting antibody bound to liraglutide fibrils;
   c) optionally quantifying antibody bound to liraglutide fibrils, optionally by use of a standard of said fibril.

\* \* \* \* \*